(12) United States Patent
Snyder et al.

(10) Patent No.: US 11,291,666 B2
(45) Date of Patent: Apr. 5, 2022

(54) USES

(71) Applicant: INTRA-CELLULAR THERAPIES, INC., New York, NY (US)

(72) Inventors: Gretchen Snyder, New York, NY (US); Lawrence P. Wennogle, Hillsborough, NJ (US); Jennifer O'Brien, New York, NY (US); Joseph Hendrick, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 399 days.

(21) Appl. No.: 16/332,750

(22) PCT Filed: Sep. 12, 2017

(86) PCT No.: PCT/US2017/051220
§ 371 (c)(1),
(2) Date: Mar. 12, 2019

(87) PCT Pub. No.: WO2018/049417
PCT Pub. Date: Mar. 15, 2018

(65) Prior Publication Data
US 2021/0213018 A1    Jul. 15, 2021

Related U.S. Application Data

(60) Provisional application No. 62/467,218, filed on Mar. 5, 2017, provisional application No. 62/412,739, filed on Oct. 25, 2016, provisional application No. 62/393,386, filed on Sep. 12, 2016.

(51) Int. Cl.
| | |
|---|---|
| A61K 31/517 | (2006.01) |
| A61K 31/519 | (2006.01) |
| A61P 27/02 | (2006.01) |
| A61P 25/28 | (2006.01) |
| A61P 37/06 | (2006.01) |
| A61K 31/4015 | (2006.01) |
| A61K 45/06 | (2006.01) |

(52) U.S. Cl.
CPC ........ *A61K 31/519* (2013.01); *A61K 31/4015* (2013.01); *A61K 45/06* (2013.01); *A61P 25/28* (2018.01); *A61P 27/02* (2018.01); *A61P 37/06* (2018.01)

(58) Field of Classification Search
CPC ................................................... A61K 31/517
USPC ............................................. 514/262.1, 267
See application file for complete search history.

(56) References Cited

U.S. PATENT DOCUMENTS

| | | |
|---|---|---|
| 4,690,935 A | 9/1987 | Taylor et al. |
| 5,202,328 A | 4/1993 | Laszlo et al. |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshlan et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance et al. |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 7,528,148 B2 | 5/2009 | Allen et al. |
| 7,579,324 B2 | 8/2009 | Burnet et al. |
| 8,273,750 B2 | 9/2012 | Li et al. |
| 8,273,751 B2 | 9/2012 | Li et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 | 9/2014 | Li et al. |
| 8,846,693 B2 | 9/2014 | Li et al. |
| 8,858,911 B2 | 10/2014 | Li et al. |
| 8,859,564 B2 | 10/2014 | Li et al. |

(Continued)

FOREIGN PATENT DOCUMENTS

| | | |
|---|---|---|
| DE | 19931206 | 1/2001 |
| EP | 0063381 | 10/1982 |

(Continued)

OTHER PUBLICATIONS

Abdel-Wahab et al., "Adverse Events Associated with Immune Checkpoint Blockade in Patients with Cancer: A Systematic Review of Case Reports," PLOS One, vol. 11(7), 15 pages (2016).

(Continued)

*Primary Examiner* — Raymond J Henley, III
(74) *Attorney, Agent, or Firm* — Hoxie & Associates LLC

(57) ABSTRACT

The disclosure provides the administration of inhibitors of phosphodiesterase 1 (PDE1) for the treatment and prophylaxis of diseases or disorders characterized by inflammation, e.g., neuroinflammation, including methods of treatment and pharmaceutical compositions for use therein.

11 Claims, 15 Drawing Sheets

(56) References Cited

U.S. PATENT DOCUMENTS

| | | | |
|---|---|---|---|
| 8,927,556 | B2 | 1/2015 | Li et al. |
| 9,000,001 | B2 | 4/2015 | Li et al. |
| 9,006,258 | B2 | 4/2015 | Fienberg et al. |
| 9,073,936 | B2 | 7/2015 | Li et al. |
| 9,157,906 | B2 | 10/2015 | Greengard et al. |
| 9,198,924 | B2 | 12/2015 | Mates et al. |
| 9,255,099 | B2 | 2/2016 | Li et al. |
| 9,403,836 | B2 | 8/2016 | Li et al. |
| 9,468,637 | B2 | 10/2016 | Fienberg et al. |
| 9,469,647 | B2 | 10/2016 | Li et al. |
| 9,545,406 | B2 | 1/2017 | Wennogle et al. |
| 9,556,186 | B2 | 1/2017 | Li et al. |
| 9,598,426 | B2 | 3/2017 | Li et al. |
| 9,624,230 | B2 | 4/2017 | Li et al. |
| 9,884,872 | B2 | 2/2018 | Li et al. |
| 10,183,023 | B2 | 1/2019 | Wennogle et al. |
| 2003/0069246 | A1 | 4/2003 | Darrow et al. |
| 2003/0092908 | A1 | 5/2003 | Pitts et al. |
| 2003/0162782 | A1 | 8/2003 | Grossman et al. |
| 2005/0075795 | A1 | 4/2005 | Pandit et al. |
| 2005/0113379 | A1 | 5/2005 | Ge et al. |
| 2008/0176961 | A1 | 7/2008 | Greengard et al. |
| 2008/0193964 | A1 | 8/2008 | Greengard et al. |
| 2008/0194592 | A1 | 8/2008 | Mates et al. |
| 2011/0015193 | A1 | 1/2011 | Eickmeier et al. |
| 2011/0312978 | A1 | 12/2011 | Davis et al. |
| 2012/0053190 | A1 | 3/2012 | Fienberg et al. |
| 2013/0085123 | A1 | 4/2013 | Li et al. |
| 2013/0324565 | A1 | 12/2013 | Li et al. |
| 2013/0331363 | A1 | 12/2013 | Li et al. |
| 2013/0338124 | A1 | 12/2013 | Li et al. |
| 2014/0005155 | A1 | 1/2014 | Li et al. |
| 2014/0011783 | A1 | 1/2014 | Li et al. |
| 2014/0148421 | A1 | 5/2014 | Li et al. |
| 2014/0194396 | A1 | 7/2014 | Li et al. |
| 2014/0235556 | A1 | 8/2014 | Halse et al. |
| 2014/0315868 | A1 | 10/2014 | Li et al. |
| 2014/0357606 | A1 | 12/2014 | Li et al. |
| 2015/0038474 | A1 | 2/2015 | Li et al. |
| 2015/0072965 | A1 | 3/2015 | Li et al. |
| 2015/0080357 | A1 | 3/2015 | Li et al. |
| 2015/0197528 | A1 | 7/2015 | Li et al. |
| 2016/0045507 | A1 | 2/2016 | Wennogle et al. |
| 2016/0083390 | A1 | 3/2016 | Li et al. |
| 2016/0324860 | A1 | 11/2016 | Hendrick et al. |
| 2016/0362489 | A1 | 12/2016 | Yang |
| 2017/0128453 | A1 | 5/2017 | Wennogle et al. |

FOREIGN PATENT DOCUMENTS

| | | |
|---|---|---|
| EP | 0095289 | 11/1983 |
| EP | 0201188 | 12/1986 |
| EP | 0636626 | 2/1995 |
| EP | 0911333 | 4/2002 |
| JP | 53031694 | 3/1978 |
| JP | 2006006333 | 1/2006 |
| JP | 2016-512842 A | 5/2016 |
| KR | 10-1991-0006866 | 9/1991 |
| WO | WO 1991/019717 | 12/1991 |
| WO | WO 1994/019351 | 9/1994 |
| WO | WO 1998/046606 | 10/1998 |
| WO | WO 1998/052568 | 11/1998 |
| WO | WO 2001/027113 | 4/2001 |
| WO | WO 2002/074312 | 9/2002 |
| WO | WO 2003/002567 | 1/2003 |
| WO | WO 2003/020702 | 3/2003 |
| WO | WO 2003/020724 | 3/2003 |
| WO | WO 2003/042216 | 5/2003 |
| WO | WO 2004/028468 | 4/2004 |
| WO | WO 2004/031375 | 4/2004 |
| WO | WO 2004/081563 | 9/2004 |
| WO | WO 2006/029257 | 3/2006 |
| WO | WO 2006/133261 | 12/2006 |
| WO | WO 2007/143568 | 12/2007 |
| WO | WO 2007/143705 | 12/2007 |
| WO | WO 2008/063505 | 5/2008 |
| WO | WO 2008/070095 | 6/2008 |
| WO | WO 2009/073210 | 6/2009 |
| WO | WO 2009/075784 | 6/2009 |
| WO | WO 2010/065148 | 6/2010 |
| WO | WO 2010/065149 | 6/2010 |
| WO | WO 2010/065151 | 6/2010 |
| WO | WO 2010/098839 | 9/2010 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |
| WO | WO 2013/024164 | 2/2013 |
| WO | WO 2013/192556 | 12/2013 |
| WO | WO 2014/145617 | 9/2014 |
| WO | WO 2014/151409 A1 | 9/2014 |
| WO | WO 2016/090380 | 6/2016 |
| WO | WO 2018/093591 A1 | 5/2018 |
| WO | WO 2019/046778 A1 | 3/2019 |
| WO | WO 2020/146384 A1 | 7/2020 |

OTHER PUBLICATIONS

"Anxiety," [retrieved on May 14, 2008], Retrieved online via Internet, URL: http://www.nim.nih.gov/medlineplus/anxiety.html, 5 pages.

"Autism," [retrieved on May 14, 2008], Retrieved online via Internet, URL: http://www.nim.nih.gov/medlineplus/autism.html, 6 pages.

Ahn et al., "Potent Tetracyclic Guanine Inhibitors of PDE1 and PDE5 Cyclic Guanosine Monophosphate Phosphodiesterases with Oral Antihypertensive Activity," J. Med. Chem., vol. 40(14), p. 2196-2210, (1997).

AL-Faleq et al., "Heterocyclic o-Aminonitriles: Preparation of Pyrazolo [3,4-d]-pyrimidines with Modification of the substituents at the 1-position," Molecules, vol. 6, p. 621-638, (2001).

Aswar et al., "Anti-Cataleptic Activity of Various Extracts of *Ocimum Sanctum*," International Journal of Pharma. Research and Development, vol. 2(6), p. 1-7, (2010).

Banker et al., Modern Pharmaceutics, Marcel Dekker, New York, 3 pages (1996).

Bastia et al., "Effect of $A_1$ and $A_{2A}$ Adenosine Receptor Ligands in Mouse Acute Models of Pain," Neuroscience letters, vol. 328, p. 241-244, (2002).

Bender et al., "Cyclic Nucleotide Phosphodiesterases: Molecular Regulation to Clinical Use," PharmcoL Rev., vol. 58(3), p. 488-520, (2006).

Blokland et al., "PDE Inhibition and Cognition Enhancement," vol. 22(4), p. 349-354, (2012) (Abstract Only) 1 page.

Boyd et al., "Dopamine Receptor Signaling and Current and Future Antipsychotic Drags," Handb Exp Pharmacol., vol. 212, p. 53-86, (2012) doi: 10.1007/978-3-642-25761-2_3.

Burnouf et al., "Synthesis, Structure-Activity Relationships, and Pharmacological Profile of 9-Amino-4-0xo-1-Phenyl-3,4,5,6, 7-Tetrahydrol[I,4]Diazepino[6, 7, 1-hi]Indoles: Discovery of Potent, Selective Phosphodiesterase Type 4 Inhibitors," J. Med. Chem., vol. 43, p. 4850-4867, (2000).

Chalimoniuk et al., "Upregulation of guanylyl cyclase expression and activity in striatum of MPTP-induced parkinsonism in mice," Biochem Biophys Res Commun., vol. 324(1), p. 118-126, (2004).

Chebib et al., "1-Phenylpyrazolo [3,4-d]pyrimidines; Structure-Activity Relationships for C6 Substituents at A1 and A2A Adenosine Receptors," Bioorganic & Medicinal Chemistry, vol. 8, p. 2581-2590, (2000).

Chen et al., "Effects of Bimatoprost 0.03% on Ocular Hemodynamics in Normal Tension Glaucoma," Journal of Ocular Pharmacology and Therpaeutics, vol. 22(3), p. 188-193, (2006).

Chen et al., "Broad Spectrum neuroprotection profile of phosphodiesterase inhibitos as related to modulation of cell-cucle elements and caspase—3 activation," Neuroscience Letters, vol. 418, p. 165-169, (2007).

(56) References Cited

OTHER PUBLICATIONS

Chermat et al., "Adaptation of the Tail Suspension Test to the Rat," Journal Pharmacology, vol. 17, p. 348-350, (1986).
Daviglus et al., "National Institutes of Health State-of-the-Science Conference Statement: Preventing Alzheimer Disease and Cognitive Decline," Annals of Internal Medicine, vol. 153(3), p. 176-185, (2010).
Deshmukh et al., "Amelioration of intracerebroventricular streptozotocin induced cognitive dysfunction and oxidative stress by vinpocetine—a PDE1 inhibitor" European Journal of Pharmacology, 620(1-3), p. 49-56, (2009).
Dewald et al., Synthesis and Potential Antipsychotic Activity of 1 H-1midazo[1.2-c]pyrazolo[3,4-e]pyrimidines, J. Med. Chem., vol. 31, p. 454-461, (1988).
Ehrman et al., "Phosphodiesterase 1B differentially modulates the effects of methamphetamine on locomotor activity and spatial learning through DARPP32-dependent pathways: evidence from PDE1B-DARPP32 double-knockout mice," Genes Brain Behav., vol. 5, p. 540-551, (2006).
Ennaceur et al., "A new one-trial test for neurobiological studies of memory in rats. 1: Behavioral data," Behavioral Brain Research, vol. 31, p. 47-59 (1988).
Fienberg et al., "DARPP-32: Regulator of the Efficacy of Dopaminergic Neurotransmission," Science, vol. 281, p. 838-842, (1998).
Filgueiras et al., "Phosphodiesterase type 1 inhibition improves learning in rats exposed to alcohol during the third trimester equivalent of human gestation," Neuroscience Letters, vol. 473(3), p. 202-207, (2010).
Gelbin et al., "Ketene-S, N-acetals as synthons for heterocycles new synthesis of pyrimidinones," Journal Fuer Praktische Chemie, vol. 329(5), p. 753-766, (1987).
Ghorab et al., "Synthesis, Anticancer and Radioprotective Activities of Some New Pyrazolo[3,4-d]pyrimidines Containing Amino Acid Moieties," Arzneimittelforschung, vol. 59(2), p. 96-103 (2009).
Goodman & Gilman, The Pharmacological Basis of Therapeutics, McGraw-Hill Interamericana, p. 892, (2007).
Greengard et al., "Beyond the Dopamine Receptor: the DARPP-321Protein Phosphatase-1 Cascade," Neuron, vol. 23, p. 435,447, (1999).
Han et al., "The Calcium/Calmodulin-dependent Phosphodiesterase PDE1C Downregulates Glucose-induced Insulin Secretion," J. Bio. Chem., vol. 274(32), p. 22337-22344, (1999).
Hulley et al., "Cyclic AMP promotes the survival of dopaminergic neurons in vitro and protects them from the toxic effects of MPP+," J Neural Transm Suppl., vol. 46, p. 217-228, (1995).
International Search Report of International Application No. PCT/US2006/022066, dated Apr. 3, 2007, 1 page.
International Search Report of International Application No. PCT/US2008/013411, dated Mar. 19, 2009, 2 pages.
International Search Report of International Application No. PCT/US2014/025666, dated Jul. 7, 2014, 3 pages.
International Search Report of International Application No. PCT/US2014/030412, dated Nov. 6, 2014, 3 pages.
International Search Report of International Application No. PCT/US2017/051220, dated Nov. 22, 2017, 3 pages.
Jiang et al., "Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol," J. Org. Chem., vol. 70, p. 2824-2827 (2004).
Ji H -M et al., "Efficacy of vinpocetine on neuropathy in patients with type 2 diabetes mellitus," Chinese Journal of New Drugs 20090815 Chinese Journal of New Drugs Co. Ltd. Chn, (Aug. 15, 2009), vol. 18, No. 15, ISSN 1003-3734, pp. 1415-1418.
Kakkar et al. "Amantadine: an antiparkinsonian agent inhibits bovine brain 60 kDa calmodulin-dependent cyclic nucleotide phosphodiesterase isozyme," Brain Res., vol. 749(2), p. 290-294, (1997).
Kakkar et al. "Calmodulin-dependent cyclic nucleotide phosphodiesterase (PDE1)" Cell Mol Life Sci., vol. 55(8-9), p. 1164-1186, (1999).
Kakkar et al., "Inhibition of Bovine Brain Calmodulin-Dependent Cyclic Nucleotide Phosphodiesterase Isozymes by Deprenyl," Life Sciences, vol. 59(21), p. 337-341, (1996).
Klaissle et al., "Physical activity and environmental enrichment regulate the generation of neural precursors in the adult mouse substantia nigra in a dopamine-dependent manner," BMC Neurosci., vol. 13:132, p. 1-15, (2012); doi: 10.1186/1471-2202-13-132.
Kleppisch et al., "Phosphodiesterases in the central nervous system," Handb Exp Pharmacol. 2009;(191):71-92. doi: 10.1007/978-3-540-68964-5_5.
Koelzer et al., "Systemic inflammation in a melanoma patient treated with immune checkpoint inhibitors—an autopsy study," Journal for ImmunoTherapy of Cancer, vol. 4(13), p. 1-8, (2016).
Laddha et al., "A new therapeutic approach in Parkinson's disease: Some novel quinazoline derivatives as dual selective phosphodiesterase 1 inhibitors and anti-inflammatory agents," Bioorganic & Medicinal Chemistry, vol. 17(19), p. 6796-6802, (2009).
Lundqvist et al., Exploitation of Structural and Regulatory Diversity in Glutamate Racemases Nature, vol. 447, p. 817-822, (2007).
Mani et al., "Requirement for DARPP-32 in Progesterone-Facilitated Sexual Receptivity in Female Rats and Mice," Science, vol. 287, p. 1053-1056, (2000).
Medina et al., "Therapeutic Utility of Phosphodiesterase Type 1 Inhibitors in Neurological Conditions," Front. Neurosci., vol. 5: 21, 6 pages, (2011).
Murray et al., "Expression and activity of cAMP phosphodiesterase isoforms in pulmonary artery smooth muscle cells from patients with pulmonary hypertension: role for PDE1," Am. J, Physiol. Luunr:1 Cell Mol. Physiol., vol. 292, p. L294-L303, (2007).
Murray et al., LY503430, a Novel_-Amlno-3-hydroxy-5-methylisoxazole-4-proplonlc Acid Receptor Potentiator with Functional, Neuroprotective and Neurotrophic Effects In Rodent Models of Parkinson's Disease, J. Pharmacol & Experim. Thera., vol. 306(2), p. 752-762, (2003).
Nishi et al., "Advanced Research on Dopamine Signaling to Develop Drugs for the Treatment of Mental Disorders: Biochemical and Behavioral Profiles of Phosphodiesterase Inhibition in Dopaminergic Neurotransmission," J. Pharmacol. Sci., vol. 114, p. 6-16, (2010).
Noguchi et al., "A Facile Preparation of 7-(substituted amino-)-6H-pyrrolo[3,4-d]-pyrimidine Derivatives"; Bulletin Chem. Soc. of Japan, vol. 62(9), p. 3043-3045; (1989).
Pardo et al., "Synthesis of 1-(p-nitrobenzyl)azoles and 1—(p. nitrobenzyl)benzazoles," Opp Briefs, vol. 32(4), p. 385-390, (2000).
Park et al., "Traumatic Brain Injury: Can the consequences be stopped?" CMAJ, vol. 178(9), p. 1163-1170, (2008).
Patani et al., "Bioisosterism: A Rational Approach in Drug Design," Chemical Reviews, vol. 96(8), p. 3147-3716 (1996).
Polli et al., "Expression of a Calmodulin-Dependent Phosphodiesterase Isoform (PDE1 B1) Correlates With Brain Regions Having Extensive Dopaminergic Innervation," The Journal of Neuroscience, vol. 14(3), p. 1251-1261, (1994).
Porsolt et al., Nature, vol. 266, p. 730-732, (1977).
Poulsen et al., "High-Pressure Synthesis of Enantiomerlcally Pure C-6 Substituted Pyrazolo[3,4-d]pyrimidines," Bioorganic & Medicinal Chemistry letter, vol. 11, p. 191-193, (2001).
Prickaerts et al., "Possible role of nitric oxide-cyclic GMP pathway in object recognition memory: Effects of 7-nitroindazole and zaprinast," European Journal of Pharmacology, vol. 337, p. 125-136 (1997).
Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning," The Joumal of Neuroscience, vol. 22(12), p. 5188-5197, (2002).
Rybalkin et al., "Cyclic GMP Phosphodiesterases and Regulation of Smooth Muscle Function," Circ. Res., vol. 93, p. 280-291, (2003).
Schmidt et al., "Phosphodiesterase inhibitors as potential cognition enhancing agents," Current Topics in Medicinal Chemistry, vol. 10(2), p. 222-230, (2010).

(56) References Cited

OTHER PUBLICATIONS

Sharma et al., "Regulation of Calmodulin-Stimulated Cyclic Nucleotide Phosphodiesterase (PDE1): Review," International Journal of Molecular Medicine, vol. 18, p. 95-105 (2006).
Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium," Cancer Research, vol. 64, p. 2568-2571, (2004).
Shook, et al. "Design and Characterization of Optimized Adenosine $A_{2A}/A_1$ Receptor Antagonists for the Treatment of Parkinson's Disease," J. Med. Chem., p. 1-47 (2012).
Silva et al., "Advances in Prodrug Design," Mini-Reviews in Medicinal Chemistry, vol. 5, p. 893-914, (2005).
Takahashi et al., "Measurement of Intracellular Calcium," Physiological Reviews, vol. 79(4), p. 1089-1125, (1999).
Takimoto et al., "Controlling Myocyte cGMP, Phosphodiesterase 1 Joins the Fray," Circulation Research, vol. 105, p. 931-933 (2009).
Turko et al., Inhibition of Cyclic GMP-Binding Cyclic GMP-Specific Phosphodiesterase (Type 5) by Sildenafil and Related Compounds, Molecular Pharmacology, vol. 56, p. 124-130, (1999).
Ungerstedt et al., "Stereotaxic Mapping of the Monoamine Pathways in the Rat Brain," Acta Physiology Second Suppl., vol. 367, p. 1-48, (1971).
Ungerstedt et al., "Quantitative Recording of Rotational Behavior in Rtas After 6-Hydroxy-Dopamine Lesions of the Nigrostriatal Dopamine System," Brain Research, vol. 24, p. 485-493, (1970).
Vatter et al., "Differential Phosphodiesterase Expression and Cytosolic $Ca^{2+}$ in Human CNS Tumour Cells and in Non-Malignant and Malignant Cells of Rat Origin," J. of Neurochemistry, vol. 93, p. 321-329 (2005).
Wolff et al., Burger's Medicinal Chemistry and Drug Discovery, Fifth Ed., vol. 1: Principles and Practice, John Wiley & Sons, p. 975, (1995).
Xia et al., Synthesis and Evaluation of Polycyclic Pyrazolo[3,4-d]pyrimidines as PDE1 and PDE5 cGMP Phosphodiesterase Inhibitors, J. Med. Chem., vol. 40, p. 4372-4377, (1997).
Youdim, "The Path from Anti Parkinson Drug Selegiline and Rasagiline to Multi-functional Neuroprotective Anti Alzheimer Drugs Ladostigil and M30," Current Alzheimer Research, vol. 3, p. 541-550 (2006).
Hebb et al., "Role of Phosphodiesterases in Neurological and Psychiatric Disease," *Current Opinion in Pharmacology*, vol. 7, pp. 86-92, (2007).
Kraft et al., "The Phosphodiesterass-4 Inhibitor Rolipram Protects from Ischemic Stroke in Mice by Reducing Blood-Brain Barrier Damage, Inflammation and Thrombosis," *Experimental Neurology*, vol. 247, pp. 80-90, (2013).
Li et al., "Discovery of Potent and Selective Inhibitors of Phosphodiesterase 1 for the Treatment of Cognitive Impairment Associated with Neurodegenerative and Neuropsychiatric Diseases," *J. Med. Chem.*, vol. 59, pp. 1149-1165, (2016).
Na et al., "The Role of Pro-Inflammatory Cytokines in the Neuroinflammation and Neurogenesis of Schizophrenia," *Progress in Neuro-Psychopharmacology & Biological Psychiatry*, vol. 48, pp. 277-286, (2014).
Snyder et al., "Preclinical Profile of ITI-214, an Inhibitor of Phosphodiesterase 1, for Enhancement of Memory Performance in Rats," *Psychopharmacology*, vol. 213, pp. 3113-3124, (2016).
Abusnina et al., "Anti-Proliferative Effect of Curcumin on Melanoma Cells is Mediated by PDE1A Inhibition that Regulates the Epigenetic Integrator UHRF1," *Mol. Nutr. Food Res.*, vol. 55, pp. 1677-1689, (2011).
Ahlström et al., "Cyclic Nucleotide Phosphodiesterases (PDEs) in Human Osteoblastic Cells; The Effect of PDE Inhibition on cAMP Accumulation," *Cell Mol Biol Lett*, vol. 10, No. 10, pp. 305-319, (2005).
Ahmad et al., "Cyclic Nucleotide Phosphodiesterases: Important Signaling Modulators and Therapeutic Targets," *Oral Diseases*, vol. 21, pp. e25-e50, (2015).
Almahariq et al., "Pharmacological Inhibition and Genetic Knockdown of Exchange Protein Directly Activated by cAMP 1 Reduce Pancreatic Cancer Metastasis In Vivo," *Molecular Pharmacology*, vol. 87, No. 2, pp. 142-149, (2015).
Argyle et al., "Targeting Macrophage-Recruiting Chemokines as a Novel Therapeutic Strategy to Prevent the Progression of Solid Tumors," *Frontiers in Immunology*, vol. 9, No. 2629, 15 pages, (2018).
Boyd et al., "cAMP-Phosphodiesterase PDE4D as a Target for Colon Cancer Therapy," *The FASEB Journal*, vol. 31, No. 1, 2 pages (2017).
Brodbelt et al., "Glioblastoma in England: 2007-2011," *Eur J Cancer*, vol. 51, pp. 533-542, (2015).
Chen et al., "cAMP Inhibits Cell Migration by Interfering with Rac-induced Lamellipodium Formation," *Journal of Biological Chemistry*, vol. 283, No. 20, p. 13799-13805, (2008).
Coussens et al., "Inflammation and Cancer," *Nature*, vol. 420, No. 6917, pp. 860-867, (2002).
Daniel et al., "Sensitivity of GBM Cells to cAMP Agonist-mediated Apoptosis Correlates with CD44 Expression and Agonist Resistance with MAPK Signaling," *Cell Death and Disease*, vol. 7, No. e2494, 11 pages, (2016).
Insel et al., "Cyclic AMP is Both a Pro-apoptotic and Anti-apoptotic Second Messenger," *Acta Physio (Oxf)*, vol. 204, No. 2, pp. 277-287, (2012).
Jang et al., "Adaptation of cAMP Signaling System in SH-SY5Y Neuroblastoma Cells Following Expression of a Constitutively Active Stimulatory G Protein Alpha, Q227L Gsα," *Exp Mol Med*, vol. 33, No. 1, pp. 37-45, (2001).
Jiang et al., "Expression and Regulation of mRNA for Distinct Isoforms of cAMP-Specific PDE-4 in Mitogen-Stimulated and Leukemic Human Lymphocytes," *Cell Biochem Biophys*, vol. 28, pp. 135-160, (1998).
Kim et al., "Antiinflammatory cAMP Signaling and Cell Migration Genes Co-opted by the Anthrax Bacillus," *PNAS*, vol. 105, No. 16, pp. 6150-6155, (2008).
Marko et al., "Cyclic 3',5'-nucleotide Phosphodiesterases: Potential Targets for Anticancer Therapy," *Chem Res Toxicol*, vol. 13, pp. 944-948, (2000).
Pantziarka et al., "Repurposing Drugs in Oncology (ReDO)—Selective PDE5 Inhibitors as Anti-Cancer Agents," *ecancer*, vol. 12, No. 824, 22 pages, (2018).
Peng et al., "Inhibitors of Phosphodiesterase as Cancer Therapeutics," *European Journal of Medicinal Chemistry*, vol. 150, pp. 742-756, (2018).
Rowther et al., "Cyclic Nucleotide Phosphodiesterase-1C (PDE1C) Drives Cell Proliferation Migration and Invasion in Glioblastoma Multiforme Cells In Vitro," *Molecular Carcinogenesis*, vol. 55, pp. 268-279, (2016).
Rybalkin et al., "Calmodulin-stimulated Cyclic Nucleotide Phosphodiesterase (PDE1C) is Induced in Human Arterial Smooth Muscle Cells of the Synthetic, Proliferative Phenotype," *J Clin Invest*, vol. 100, No. 10, pp. 2611-2621, (1997).
Savai et al., "Targeting Cancer with Phosphodiesterase Inhibitors," *Expert Opin. Investig. Drugs*, vol. 19, No. 1, pp. 117-131, (2010).
Shimizu et al., "Characterization of Phosphodiesterase 1 in Human Malignant Melanoma Cell Lines," *AntiCancer Research*, vol. 29, pp. 1119-1122, (2009).
Sh1ri et al., "Dendrosomal Curcumin Suppresses Metastatic Breast Cancer in Mice by Changing M1/M2 Macrophage Balance in the Tumor Microenvironment," *Asian Pacific Journal of Cancer Prevention*, vol. 16, 7 pages, (2015).
Soon, L., "A Discourse on Cancer Cell Chemotaxis: Where to From Here?", *IUBMB Life*, vol. 59, No. 2, pp. 60-67, (2007).
Stupp et al., "Radiotherapy Plus Concomitant and Adjuvant Temozolomide for Glioblastoma", *N Engl J Med*, vol. 352, No. 10, pp. 987-996, (2005).
Touat et al., "Glioblastoma Targeted Therapy: Updated Approaches from Recent Biological Insights," *Ann. Oncol.*, vol. 28, No. 7, pp. 1457-1472, (2017).
Vitale et al., "A New Therapeutic Strategy Against Cancer: cAMP Elevating Drugs and Leptin," *Cancer Biology & Therapy*, vol. 8, No. 12, pp. 1191-1193, (2009).

(56) References Cited

OTHER PUBLICATIONS

Watanabe et al., "Phosphodiesterase 4 Regulates the Migration of B16-F10 Melanoma Cells," *Exp Ther Med*, vol. 4, pp. 205-210, (2012).

"Gene expression," Wikipedia, 17 pages, (2017); accessed on Jul. 18, 2019 at https://en.wikipedia.org/w/index.php?title=Gene_expression&oldid=803718522.

Zong et al., "The Cellular Origin for Malignant Glioma and Prospects for Clinical Advancements," *Expert Rev Mol Diagn.*, vol. 12, No. 4, pp. 383-394, (2012).

USES

CROSS REFERENCE TO RELATED APPLICATIONS

This application is a United States Application under 35 U.S.C. § 371 claiming benefit of PCT Application No. PCT/US2017/051220, filed on Sep. 12, 2017, which claims the benefit and priority to U.S. Provisional Application 62/393,386, filed Sep. 12, 2016, as well as U.S. Provisional Application 62/412,739, filed Oct. 25, 2016, as well as U.S. Provisional Application 62/467,218, filed Mar. 5, 2017, the contents of each of which are incorporated herein by reference in their entireties.

FIELD OF THE INVENTION

The field relates to the administration of inhibitors of phosphodiesterase 1 (PDE1) inhibitors for the treatment and prophylaxis of inflammation and/or diseases or disorders related to inflammation, e.g., neuroinflammation.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), are activated by the $Ca^{2+}$-calmodulin and have been shown to mediate the calcium and cyclic nucleotide (e.g. cAMP and cGMP) signaling pathways. These PDEs are therefore active in stimulated conditions when intra-cellular calcium levels rise, leading to increased hydrolysis of cyclic nucleotides. The three known CaM-PDE genes, PDE1A, PDE1B, and PDE1C, are all expressed in central nervous system tissue. In the brain, the predominant expression of PDE1A is in the cortex and neostriatum, PDE1B is expressed in the neostriatum, prefrontal cortex, hippocampus, and olfactory tubercle, and PDE1C is more ubiquitously expressed.

PDE4 is the major cAMP-metabolizing enzyme found in inflammatory and immune cells, and PDE4 inhibitors are of interest as anti-inflammatory drugs. PDE1, however, has not been thought to play a major role in the inflammatory response, although PDE-1 is induced in monocyte-to-macrophage differentiation mediated by the cytokine granulocyte-macrophage colony-stimulating factor (GM-CSF). The PDE1 inhibitor vinpocetine has been shown to be anti-inflammatory, but the anti-inflammatory action of vinpocetine is believed to be caused by a direct inhibition of the IκB kinase complex (IKK) rather than PDE blockade.

Microglia have a central role in maintaining homeostasis and mediating inflammation in the brain. Microglia communicate with complex signaling to neurons and astrocytes, determining how many brains cells are needed and when to eliminate a synapse, e.g., destroying the defective or unused synapses. Microglia may exist in different states: a resting state, which is relatively inactive but may perform surveillance functions, or in one of two functionally distinct activation states, M1 and M2. The M1 state is induced by a signal such as IFN-γ or lipopolysaccharide (LPS), and responds by releasing inflammatory cytokines such as TNF-, IL-1β, and reactive oxygen species/reactive nitrogen species (ROS/NOS). The M2 state has an anti-inflammatory effect, blocking the release of pro-inflammatory cytokines, ingesting debris, promoting tissue repair and releasing neurotrophic factors. Activated microglia have been associated with a variety of neurodegenerative diseases including Alzheimer's disease (AD), Parkinson's disease (PD) and amyotrophic lateral sclerosis (ALS), and may contribute to the pathology of these diseases, although it is not conclusively determined whether inflammation is an underlying cause or an effect of these conditions.

It has not been previously shown that PDE1 has a significant role in mediating inflammatory cytokines, in the brain or elsewhere, or that it would have a significant effect on inflammatory diseases. Inflammatory processes in general, and diseases and disorders related to inflammation, are numerous, and the mechanisms and actions are still not well understood. Currently, there is a largely unmet need for an effective way of treating inflammation and inflammatory related diseases and disorders, especially with regard to inflammation occurring in the brain.

SUMMARY OF THE INVENTION

Figure 1:
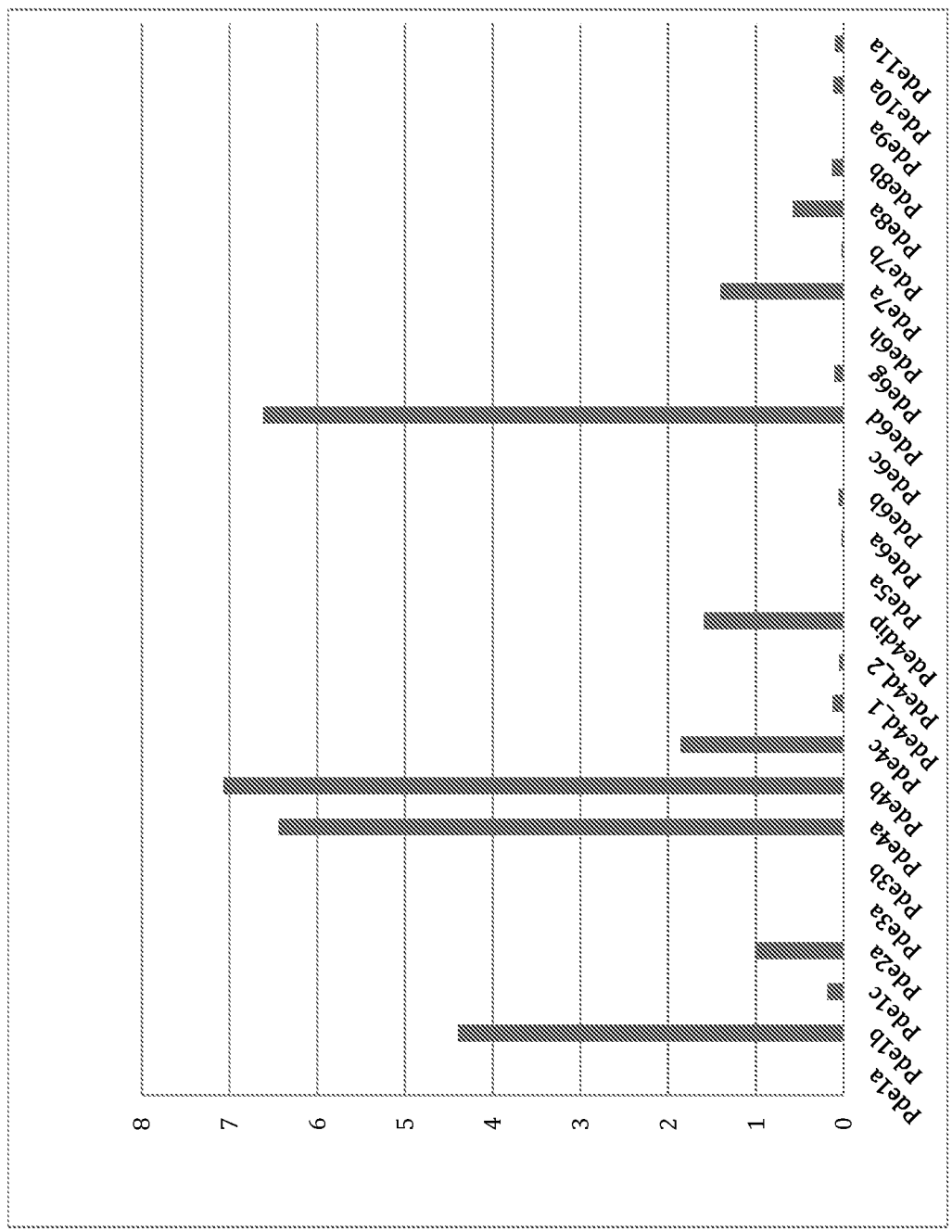
FIG. 1 depicts phosphodiesterase expression in BV2 cells treated with LPS-RNAseq analysis. FPKM refers to Fragment Reads per kilobase of exon per million reads mapped.

Surprisingly, we have discovered that PDE1 mediates the expression of certain pro-inflammatory cytokines and chemokines and that PDE1 inhibitors have specific anti-inflammatory effects, which are different from the anti-inflammatory effects of PDE4 inhibitors. In one aspect, inhibition of PDE1 regulates inflammatory activity in microglia, reducing expression of pro-inflammatory genes, with a profile different from PDE4 inhibition, thereby providing novel treatments for toxic neuroinflammation.

Negative regulation of inflammatory responses in microglia by elevated intracellular cyclic nucleotide levels provides a promising area for therapeutic intervention. Cyclic guanosine monophosphate (cGMP) in microglia is produced by activation of atrial natriuretic receptors or soluble guanylyl cyclase and is hydrolyzed by phosphodiesterases (PDEs). Increasing intracellular cGMP by either stimulating production or inhibiting hydrolysis has been shown to attenuate LPS-induced responses in microglia. Additionally, cGMP has been shown to play a role in LPS-induced motility of microglia. Cyclic adenosine monophosphate (cAMP) is also a key regulator of inflammatory responses. LPS and cytokine stimulation have been shown to increase expression of PDE4B and decrease cAMP. PDEs are proven drug-able targets. Enzymes of the PDE1 family, of which PDE1B is expressed in microglia, hydrolyze both cAMP and cGMP and are activated by calcium.

Among the roles played by the PDE1 enzyme targets of the compounds of the invention, the PDE1B isoform is found in high abundance in microglia, where it may play a role in controlling inflammatory responses, in particular under conditions of elevated intracellular calcium. This suggests that ITI-214 might prove beneficial in diseases associated with, for example, chronic neuroinflammation.

In one embodiment, therefore, the invention provides using various PDE1 inhibitory compounds to treat inflammation, and/or diseases or disorders related to inflammation. Inflammation can be neuroinflammation, and in one embodiment the PDE1 inhibitors can specifically modulate microglial activation in the brain. We have surprisingly discovered that the LPS-induced expression of certain inflammatory biomarkers (e.g., IL1β, TNF-α, and Ccl2) can be blunted or decreased with the administration of a PDE1 inhibitor as described herein. This discovery has wide-ranging applications for treating inflammatory diseases and disorders related or correlated to the expression of various inflammatory biomarkers.

Without being bound by theory, one possible mechanism for this activity is that inhibition of PDE1B may affect macrophage activation in the blood and/or microglial activation in the CNS, so as to reduce M1 activation and the release of pro-inflammatory cytokines, and to enhance the action of M2 microglia, through the up-regulation of anti-inflammatory cytokines such as IL-10. The role of neuroinflammation and microglial function in CNS pathologies is not fully understood, but we hypothesize that it is relevant to a variety of conditions, including:

a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;

b. repair of damage due to stroke, cardiac arrest, hypoxia, intracerebral hemorrhage or traumatic brain injury;

c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation;

d. chronic CNS infections, e.g., Lyme disease, syphilis, or CNS infection consequent to an immunosuppressive condition, e.g., HIV dementia;

e. neuroinflammation consequent to chemotherapy.

Targeted inhibition of PDE1 in the brain with a compound of the present invention is believed to affect microglial activation and reduce damaging pro-inflammatory cytokine signaling, and at the same time, increasing production of anti-inflammatory cytokines and factors involved in microglia motility and recruitment.

Accordingly, in one embodiment, the invention provides a new method of treatment or prophylaxis of inflammation or disease associated with inflammation that may be ameliorated by administration of a specific inhibitor of phosphodiesterase type I (e.g., PDE1 inhibitor, e.g., a PDE1B inhibitor) (e.g., a PDE1 inhibitor of Formula I, II, III, IV, V, VI, VII, VIII, IX, X, XI, and/or XII as herein described).

In one embodiment the invention provides a method of treating neuroinflammation and/or diseases or disorders associated with neuroinflammation and/or microglial function, e.g., selected from:

a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;

b. stroke, cardiac arrest, hypoxia, intracerebral hemorrhage or traumatic brain injury;

c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and d. chronic CNS infections, e.g., Lyme disease or CNS infection consequent to an immunosuppressive condition, e.g., HIV-dementia;

e. neuroinflammation consequent to chemotherapy;

comprising administering an effective amount of a PDE1 inhibitor of the current invention (e.g., a PDE1 inhibitor of Formula I, II, III, IV, V, VI, VII, VIII, IX, X, XI, and/or XII as herein described), e.g., an amount effective to (i) reduce or inhibit activation of M1 microglia, and/or (ii) and amount effective to reduce levels of one or more pro-inflammatory cytokines (e.g., IL1β, TNF-α, and Ccl2, or combination thereof); to a patient in need thereof.

In one embodiment PDE1 inhibitors of the current invention (e.g., a PDE1 inhibitor of Formula I, II, III, IV, V, VI, VII, VIII, IX, X, XI, and/or XII as herein described) are administered to a patient with increased levels of one or more pro-inflammatory cytokines (e.g., IL1β, TNF-α, and Ccl2, or combination thereof), e.g., to a patient suffering from neuroinflammation and/or diseases or disorders associated with neuroinflammation and/or microglial function, e.g., selected from:

a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;

b. stroke, cardiac arrest, hypoxia, intracerebral hemorrhage or traumatic brain injury;

c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and d. chronic CNS infections, e.g., Lyme disease or CNS infection consequent to an immunosuppressive condition, e.g., HIV-dementia;

e. neuroinflammation consequent to chemotherapy.

Further embodiments of the invention are set forth or evident from the detailed description below and the examples herein.

DETAILED DESCRIPTION OF THE INVENTION

Compounds for Use in the Methods of the Invention

In one embodiment, the PDE1 inhibitors for use in the methods of treatment and prophylaxis described herein are optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B: In one embodiment, the PDE1 inhibitors for use in the methods of treatment and prophylaxis described herein are optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B:

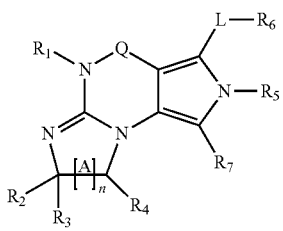

Formula II-A or

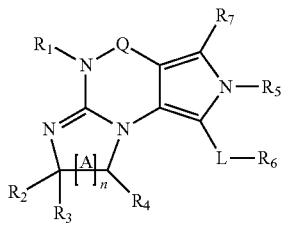

Formula II-B wherein
(i) Q is C(=O), C(=S), C(=N($R_{20}$)) or $CH_2$;
(ii) L is a single bond, —N(H)—, —$CH_2$—, —S—, —S(O)— or —S($O_2$)—;
(iii) $R_1$ is H or C1-4 alkyl (e.g., methyl);
(iv) $R_4$ is H or $C_{1-6}$ alkyl (e.g., methyl or isopropyl) and $R_2$ and $R_3$ are, independently,
H
$C_{1-6}$ alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl),
aryl,
heteroaryl,
(optionally hetero)arylalkoxy,
(optionally hetero)aryl$C_{1-6}$ alkyl; or
$R_2$ and $R_3$ together form a 3- to 6-membered ring;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
or
(v) $R_5$ is
a) -D-E-F, wherein:
D is $C_{1-4}$ alkylene (e.g., methylene, ethylene or prop-2-yn-1-ylene);
E is a single bond, $C_{2-4}$ alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
halo$C_{1-4}$ alkyl (e.g., trifluoromethyl),
—C(O)—$R_{15}$,
N($R_{16}$)($R_{17}$), or
$C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), $C_{1-4}$ alkyl (e.g., methyl), halo$C_{1-4}$ alkyl (e.g., trifluoromethyl), $C_{1-4}$ alkoxy (e.g., methoxy), hydroxy, $C_{1-4}$ carboxy, or an additional aryl or heteroaryl (e.g., biphenyl or pyridylphenyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$ alkyl (e.g., 5-trifluoromethylpyrid-2-yl) or C$_{1-4}$ alkyl (e.g., 5-methylpyrid-2-yl), or F is aryl, e.g., phenyl, substituted with one or more halo (e.g., 4-fluorophenyl) or F is a C$_{3-7}$heterocycloalkyl (e.g., pyrrolidinyl) optionally substituted with a C$_{1-6}$ alkyl (e.g., 1-methylpyrrolidin-3-yl); or b) a substituted heteroarylalkyl, e.g., substituted with haloC$_{1-4}$ alkyl;

c) attached to the nitrogen on the pyrrolo portion of Formula II-A or II-B and is a moiety of Formula A

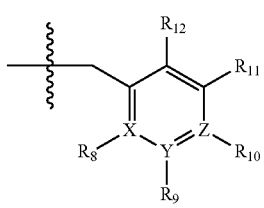

Formula A wherein X, Y and Z are, independently, N or C, and R$_8$, R$_9$, R$_{11}$ and R$_{12}$ are independently H or halogen (e.g., Cl or F), and R$_{10}$ is halogen,
C$_{1-4}$ alkyl,
haloC$_{1-4}$ alkyl (e.g., triflouromethyl)
C$_{1-4}$ alkoxy (e.g. methoxy),
C$_{3-7}$ cycloalkyl,
heteroC$_{3-7}$cycloalkyl (e.g., pyrrolidinyl or piperidinyl),
C$_{1-4}$ haloalkyl (e.g., trifluoromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently, optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, —SH or an additional aryl, heteroaryl (e.g., biphenyl or pyridylphenyl) or C$_{3-8}$ cycloalkyl,
preferably R$_{10}$ is phenyl, pyridyl, piperidinyl or pyrrolidinyl optionally substituted with the substituents previously defined, e.g. optionally substituted with halo or alkyl
provided that when X, Y, or Z is nitrogen, R$_8$, R$_9$, or R$_{10}$, respectively, is not present;

(vi) R$_6$ is
H,
C$_{1-4}$alkyl (e.g., methyl, ethyl, n-propyl, isobutyl),
C$_{3-7}$cycloalkyl (e.g., cyclopentyl or cyclohexyl),
heteroC$_{3-7}$cycloalkyl (e.g., pyrrolidinyl, piperidinyl, morpholinyl),
aryl (e.g., phenyl),
heteroaryl (e.g., pyrid-4-yl),
arylC$_{1-4}$alkyl (e.g., benzyl),
arylamino (e.g., phenylamino),
heteroarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$),
wherein the aryl and heteroaryl are optionally substituted with one or more C$_{1-4}$alkyl (e.g., methyl), halogen (e.g., chloro or fluoro), haloC$_{1-4}$alkyl (e.g., trifluoromethyl), hydroxy, C$_{1-4}$carboxy, or an additional aryl, heteroaryl (e.g., biphenyl or pyridylphenyl) or C$_{3-8}$cycloalkyl;

(vii) R$_7$ is H, C$_{1-6}$ alkyl (e.g., methyl or ethyl), halogen (e.g., Cl), —N(R$_{18}$)(R$_{19}$), hydroxy or C$_{1-6}$ alkoxy;

(viii) n=0 or 1;

(ix) when n=1, A is —C(R$_{13}$R$_{14}$)—, wherein R$_{13}$ and R$_{14}$, are, independently, H or C$_{1-4}$ alkyl, aryl, heteroaryl, (optionally hetero)arylC$_{1-4}$ alkoxy, (optionally hetero)arylC$_{1-4}$ alkyl or R$_{14}$ can form a bridge with R$_2$ or R$_4$;

(x) R$_{15}$ is C$_{1-4}$ alkyl, haloC$_{1-4}$ alkyl, —OH or —OC$_{1-4}$ alkyl (e.g., —OCH$_3$)

(xi) R$_{16}$ and R$_{17}$ are independently H or C$_{1-4}$ alkyl;

(xii) R$_{18}$ and R$_{19}$ are independently
H,
C$_{1-4}$alky (e.g., methyl, ethyl, n-propyl, isobutyl),
C$_{3-8}$ cycloalky (e.g., cyclohexyl or cyclopenyl),
heteroC$_{3-8}$ cycloalky (e.g., pyrrolidinyl, piperidinyl, morpholinyl),
aryl (e.g., phenyl) or
heteroaryl (e.g., pyridyl),
wherein said aryl and heteroaryl are optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
C$_{1-4}$alkyl (e.g., methyl),
haloC$_{1-4}$alkyl (e.g., trifluoromethyl),
C$_{1-4}$ carboxy, or
an additional aryl, heteroaryl (e.g., biphenyl or pyridylphenyl) or C$_{3-8}$ cycloalkyl, (xiii) R$_{20}$ is H, C$_{1-4}$ alkyl or C$_{3-7}$cycloalkyl;

in free or salt form.

In another embodiment, the PDE1 inhibitors for use in the methods of treatment and prophylaxis described herein are Compound of Formula I, e.g. Formula I-A and I-B:

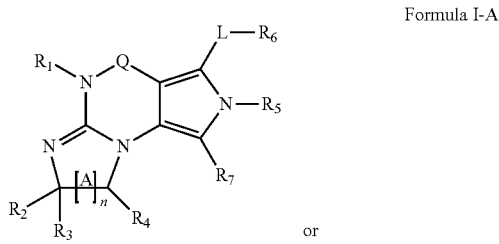

Formula I-A or

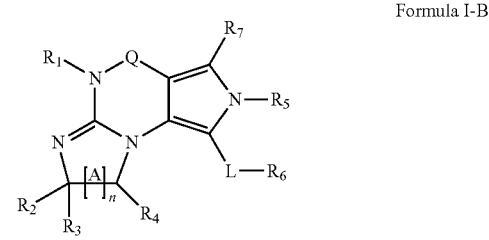

Formula I-B wherein
(i) Q is C(=O), C(=S), C(=N(R$_{20}$)) or CH$_2$;
(ii) L is a single bond, —N(H)—, —CH$_2$—, —S—, —S(O)— or —S(O$_2$)—;
(iii) R$_1$ is H or C$_{1-4}$ alkyl (e.g., methyl);
(iv) R$_4$ is H or C$_{1-6}$ alkyl (e.g., methyl or isopropyl) and R$_2$ and R$_3$ are,
independently,
H or C$_{1-6}$ alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy, or
(optionally hetero)arylC$_{1-6}$ alkyl;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
(v) R$_5$ is
a) -D-E-F, wherein:
D is C$_{1-4}$ alkylene (e.g., methylene, ethylene or prop-2-yn-1-ylene);
E is a single bond, C$_{2-4}$ alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
haloC$_{1-4}$ alkyl (e.g., trifluoromethyl),
—C(O)—R$_{15}$,
N(R$_{16}$)(R$_{17}$), or
C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), C$_{1-4}$ alkyl (e.g., methyl), haloC$_{1-4}$ alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$ alkyl (e.g., 5-trifluoromethylpyrid-2-yl) or C$_{1-4}$ alkyl (e.g., 5-methylpyrid-2-yl), or F is aryl, e.g., phenyl, substituted with one or more halo (e.g., 4-fluorophenyl) or F is a C$_{3-7}$heterocycloalkyl (e.g., pyrrolidinyl) optionally substituted with a C$_{1-6}$alkyl (e.g., 1-methylpyrrolidin-3-yl); or
b) a substituted heteroarylalkyl, e.g., substituted with haloalkyl;
c) attached to the nitrogen on the pyrrolo portion of Formula I-A or I-B and is a moiety of Formula A

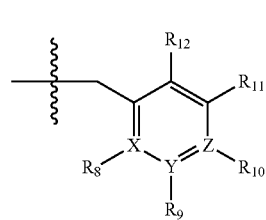

Formula A wherein X, Y and Z are, independently, N or C, and R$_8$, R$_9$, R$_{11}$ and R$_{12}$ are independently H or halogen (e.g., Cl or F), and R$_{10}$ is
halogen,
C$_{1-4}$alkyl,
C$_{3-7}$ cycloalkyl,
C$_{1-4}$ haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, R$_8$, R$_9$, or R$_{10}$, respectively, is not present;
(vi) R$_6$ is
H,
C$_{1-4}$ alkyl,
C$_{3-7}$cycloalkyl (e.g., cyclopentyl),
aryl (e.g., phenyl),
heteroaryl (e.g., pyrid-4-yl),
arylC$_{1-4}$alkyl (e.g., benzyl),
arylamino (e.g., phenylamino),
heteroarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$);
wherein the aryl or heteroaryl is optionally substituted with one or more halo (e.g., F, Cl), hydroxy or C$_{1-6}$ alkoxy;
(vii) R$_7$ is H, C$_{1-6}$ alkyl, halogen (e.g., Cl), —N(R$_{18}$)(R$_{19}$);
(viii) n=0 or 1;
(ix) when n=1, A is —C(R$_{13}$R$_{14}$)—, wherein R$_{13}$ and R$_{14}$, are, independently, H or C$_{1-4}$ alkyl, aryl, heteroaryl, (optionally hetero)arylC$_{1-4}$ alkoxy or (optionally hetero)arylC$_{1-4}$alkyl;
(x) R$_{15}$ is C$_{1-4}$ alkyl, haloC$_{1-4}$ alkyl, —OH or —OC$_{1-4}$ alkyl (e.g., —OCH$_3$)
(xi) R$_{16}$ and R$_{17}$ are independently H or C$_{1-4}$ alkyl;
(xii) R$_{18}$ and R$_{19}$ are independently H, C$_{1-4}$ alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xiii) R$_{20}$ is H, C$_{1-4}$ alkyl or C$_{3-7}$cycloalkyl;
in free or salt form.
1.1 any of the preceding formulae wherein the compounds inhibit phosphodiesterase-mediated (e.g., PDE1-mediated, especially PDE1B-mediated) hydrolysis of cGMP, e.g., with an IC$_{50}$ of less than 1 μM, preferably less than 750 nM, more preferably less than 500 nM, more preferably less than 50 nM in an immobilized-metal affinity particle reagent PDE assay,
in free or salt form.

The invention further provides optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, in free or salt form, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., a Compound of Formula III:

Formula III wherein
(xiv) Q is C(=S), C(=N($R_{20}$)) or $CH_2$;
(xv) L is a single bond, —N(H)—, —$CH_2$—;
(xvi) $R_1$ is H or $C_{1-4}$ alkyl (e.g., methyl or ethyl);
(xvii) $R_4$ is H or $C_{1-6}$ alkyl (e.g., methyl, isopropyl) and $R_2$ and $R_3$ are,
independently:
H or $C_{1-6}$ alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
aryl,
heteroaryl,
(optionally hetero)arylalkoxy,
(optionally hetero)aryl$C_{1-6}$ alkyl, or
$R_2$ and $R_3$ together form a 3- to 6-membered ring;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(xviii) $R_5$ is
d) -D-E-F, wherein:
D is $C_{1-4}$ alkylene (e.g., methylene, ethylene or prop-2-yn-1-ylene);
E is a single bond, $C_{2-4}$ alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl), halo (e.g., F, Br, Cl),
halo$C_{1-4}$ alkyl (e.g., trifluoromethyl),
—C(O)—$R_{15}$,
—N($R_{16}$)($R_{17}$),
—S(O)$_2 R_{21}$ or
$C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more:
halo (e.g., F, Cl or Br),
$C_{1-4}$ alkyl (e.g., methyl),
halo$C_{1-4}$ alkyl (e.g., trifluoromethyl),
$C_{1-4}$ alkoxy or
$C_{1-4}$ alkyl (e.g., 5-methylpyrid-2-yl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl),
or F is aryl, e.g., phenyl, substituted with one or more halo (e.g., 4-fluorophenyl)
or F is a $C_{3-7}$heterocycloalkyl (e.g., pyrrolidinyl) optionally substituted with a $C_{1-6}$ alkyl (e.g., 1-methylpyrrolidin-3-yl);
or
e) a substituted heteroarylalkyl, e.g., substituted with haloalkyl;
f) attached to one of the nitrogens on the pyrazolo portion of Formula III and is a moiety of Formula A Formula A wherein X, Y and Z are, independently, N or C, and $R_8$, $R_9$, $R_{11}$
and $R_{12}$ are independently H or halogen (e.g., Cl or F), and $R_{10}$ is:
halogen,
$C_{1-4}$ alkyl,
$C_{3-7}$ cycloalkyl,
het$C_{3-7}$ cycloalkyl (e.g., pyrrolidinyl or piperidinyl),
$C_{1-4}$ haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently and optionally substituted with one or more halo (e.g., F or Cl), $C_{1-4}$alkyl, $C_{1-4}$alkoxy, $C_{1-4}$ haloalkyl (e.g., trifluoromethyl), —SH;
preferably $R_{10}$ is phenyl, pyridyl, piperidinyl or pyrrolidinyl optionally substituted with the substituents previously defined, e.g. optionally substituted with halo or alkyl provided that when X, Y, or Z is nitrogen, $R_8$, $R_9$, or $R_{10}$, respectively, is not present;

(xix) $R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy, $C_{1-6}$ alkyl, $C_{1-6}$ alkoxy, $C_{3-8}$cycloalkyl, for example, $R_6$ is 4-hydroxyphenyl or 4-fluorophenyl, (xx) n=0 or 1;

(xxi) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$ alkyl or $R_{13}$ or $R_{14}$ can form a bridge with $R_2$ or $R_4$;

(xxii) $R_{15}$ is $C_{1-4}$ alkyl, halo$C_{1-4}$ alkyl, —OH or —O$C_{1-4}$ alkyl (e.g., —OCH$_3$)

(xxiii) $R_{16}$ and $R_{17}$ are independently H or $C_{1-4}$ alkyl;

(xxiv) $R_{18}$ and $R_{19}$ are independently
H,
$C_{1-4}$ alky,
$C_{3-8}$ cycloalkyl,
hetero$C_{3-8}$ cycloalkyl,
aryl (e.g., phenyl), or
heteroaryl,
wherein said aryl or heteroaryl is optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$ alkyl,
halo$C_{1-6}$ alkyl,
$C_{1-6}$ alkoxy,
aryl,
heteroaryl, or
$C_{3-8}$ cycloalkyl;

(xxv) $R_{20}$ is H, $C_{1-4}$ alkyl (e.g., methyl) or $C_{3-7}$cycloalkyl, (xxvi) $R_{21}$ is $C_{1-6}$ alkyl;

in free or salt form.

In yet another embodiment, the invention also provides a Compound of Formula IV:

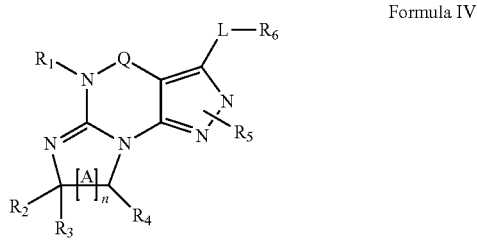

Formula IV wherein
Q is C(=S), C(=N($R_{20}$)) or CH$_2$;
L is a single bond, —N(H)—, —CH$_2$—;
$R_1$ is H or $C_{1-4}$ alkyl (e.g., methyl or ethyl);
$R_4$ is H or $C_{1-6}$ alkyl (e.g., methyl, isopropyl) and $R_2$ and $R_3$ are, independently, H or $C_{1-6}$ alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, or (optionally hetero)aryl$C_{1-6}$ alkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
$R_5$ is
a) -D-E-F, wherein:
D is $C_{1-4}$ alkylene (e.g., methylene, ethylene or prop-2-yn-1-ylene);
E is a single bond, $C_{2-4}$ alkynylene (e.g., —C≡C—), arylene (e.g., phenylene) or heteroarylene (e.g., pyridylene);
F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, CO, halo$C_{1-4}$ alkyl (e.g., trifluoromethyl), —C(O)—$R_{15}$, —N($R_{16}$)($R_{17}$), —S(O)$_2R_{21}$ or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more:
halo (e.g., F, Cl or Br),
$C_{1-4}$ alkyl (e.g., methyl),
halo$C_{1-4}$ alkyl (e.g., trifluoromethyl),
for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$ alkyl (e.g., 5-trifluoromethylpyrid-2-yl) or $C_{1-4}$ alkyl (e.g., 5-methylpyrid-2-yl),
or F is aryl, e.g., phenyl, substituted with one or more halo (e.g., 4-fluorophenyl)
or F is a $C_{3-7}$heterocycloalkyl (e.g., pyrrolidinyl) optionally substituted with a $C_{1-6}$ alkyl (e.g., 1-methylpyrrolidin-3-yl); or
b) a substituted heteroarylalkyl, e.g., substituted with haloalkyl;
c) attached to one of the nitrogens on the pyrazolo portion of Formula IV and is a moiety of Formula A

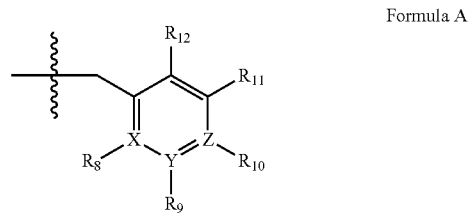

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
$C_{1-4}$alkyl, $C_{3-7}$ cycloalkyl,
$C_{1-4}$ haloalkyl (e.g., trifluoromethyl),
aryl (e.g., phenyl),
heteroaryl (e.g., pyridyl (for example pyrid-2-yl), or
thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, $R_8$, $R_9$, or $R_{10}$, respectively, is not present;

$R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$ alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1, 1'-biphen-4-ylmethyl)amino), or
—N($R_{18}$)($R_{19}$);
wherein the aryl or heteroaryl is optionally substituted with one or more halo (e.g., F, Cl), hydroxy or $C_{1-6}$ alkoxy, for example, $R_6$ is 4-hydroxyphenyl or 4-fluorophenyl, n=0 or 1;
when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$ alkoxy or (optionally hetero)aryl$C_{1-4}$alkyl;

$R_{15}$ is $C_{1-4}$ alkyl, halo$C_{1-4}$ alkyl, —OH or —O$C_{1-4}$ alkyl (e.g., —OCH$_3$)

$R_{16}$ and $R_{17}$ are independently H or $C_{1-4}$ alkyl;

$R_{18}$ and $R_{19}$ are independently H, $C_{1-4}$ alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)

$R_{20}$ is H, $C_{1-4}$ alkyl (e.g., methyl) or $C_{3-7}$cycloalkyl, $R_{21}$ is $C_{1-6}$ alkyl;

in free or salt form.

In still yet another embodiment, the invention provides that the PDE1 inhibitors for use in the methods of treatment and prophylaxis which are described herein are selected from any of the Applicant's own publications: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, and WO 2011/153138, the entire contents of each of which are incorporated herein by reference in their entireties.

In yet another embodiment the invention provides that the PDE1 inhibitors for use in the methods of treatment and prophylaxis described herein are compounds of Formula V:

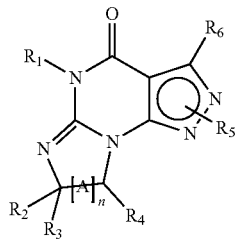

Formula V wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl or
$R_5$ is attached to one of the nitrogens on the pyrazolo portion of Formula V and is a moiety of Formula A

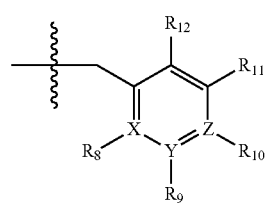

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1;

(vi) when n=1, A is —C($R_{13}R_{14}$)—
wherein Ria and $R_{10}$, are, independently, H or $C_{1-4}$ alkyl, aryl, heteroaryl, (optionally hetero)arylalkoxy or (optionally hetero)arylalkyl;

in free, salt or prodrug form, including its enantiomers, diastereoisomers and racemates.

In one embodiment the invention provides that the PDE1 inhibitors for use in the methods of treatment and prophylaxis described herein are compounds of Formula VI:

Formula VI

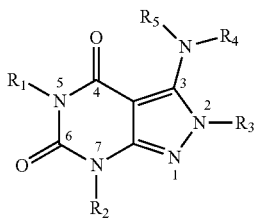

wherein:
(i) $R_1$ is H or alkyl;
(ii) $R_2$ is H, alkyl, cycloalkyl, haloalkyl, alkylaminoalkyl, hydroxyalkyl, arylalkyl, heteroarylalkyl, or alkoxyarylalkyl;
(iii) $R_3$ is heteroarylmethyl or formula A Formula A

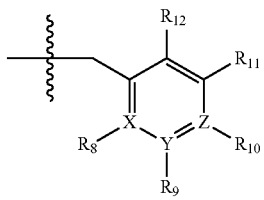

wherein X, Y and Z are, independently, N or C, and $R_8$, $R_9$, $R_{11}$ and $R_{12}$ are independently H or halogen; and $R_{10}$ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;
(iv) $R_4$ is aryl or heteroaryl; and
(v) $R_5$ is H, alkyl, cycloalkyl, heteroaryl, aryl, p-benzylaryl;
provided that when X, Y or X is nitrogen, $R_8$, $R_9$ or $R_{10}$, respectively, is not present; wherein "alk" or "alkyl" refers to $C_{1-6}$ alkyl and "cycloalkyl" refers to $C_{3-6}$ cycloalkyl, in free, salt or physiologically hydrolysable and acceptable ester prodrug form.

In one embodiment the invention provides that the PDE1 inhibitors for use in the methods of treatment and prophylaxis described herein are compounds of Formula VII:

Formula VII

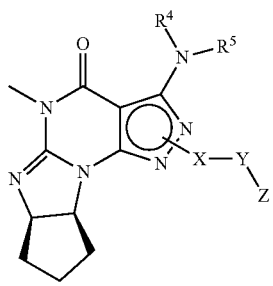

(i) X is $C_{1-6}$ alkylene (e.g., methylene, ethylene or prop-2-yn-1-ylene);
(ii) Y is a single bond, alkynylene (e.g., —C≡C—), arylene (e.g., phenylene) or heteroarylene (e.g., pyridylene);
(iii) Z is H, aryl (e.g., phenyl), heteroaryl (e.g., pyridyl, e.g., pyrid-2-yl), halo (e.g., F, Br, Cl), halo$C_{1-6}$ alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl);
(iv) $R^1$ is $C_{1-6}$ alkyl, halo$C_{1-6}$ alkyl, —OH or —O$C_{1-6}$ alkyl (e.g., —OCH$_3$);
(v) $R^2$ and $R^3$ are independently H or $C_{1-6}$ alkyl;
(vi) $R^4$ and $R^5$ are independently H, $C_{1-6}$ alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$ alkoxy;
(vii) wherein X, Y and Z are independently and optionally substituted with one or more halo (e.g., F, Cl or Br), $C_{1-6}$ alkyl (e.g., methyl), halo$C_{1-6}$ alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$ alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl),
in free, salt or prodrug form.

In one embodiment the invention provides that the PDE1 inhibitors for use in the methods of treatment and prophylaxis described herein are compounds of Formula VIII:

Formula VIII

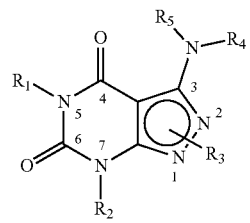

wherein
(i) $R_1$ is H or $C_{1-6}$ alkyl;
(ii) $R_2$ is
H,
$C_{1-6}$ alkyl,
$C_{3-8}$ cycloalkyl optionally substituted with one or more amino,
$C_{3-8}$ heterocycloalkyl optionally substituted with $C_{1-6}$ alkyl,
$C_{3-8}$ cycloalkyl-$C_{1-6}$ alkyl,
$C_{1-6}$ haloalkyl,
$C_{0-6}$alkylamino$C_{0-6}$ alkyl,
hydroxy$C_{1-6}$alkyl,
aryl$C_{0-6}$alkyl,
heteroarylalkyl,
$C_{1-6}$alkoxyaryl$C_{1-6}$alkyl, or
-G-J wherein:
G is a single bond or, alkylene;
J is cycloalkyl or heterocycloalkyl optionally substituted with alkyl;
(iii) $R_3$ is
a) -D-E-F wherein
1. D is single bond, $C_{1-6}$ alkylene or aryl$C_{1-6}$ alkylene;
2. E is a $C_{1-6}$ alkylene, arylene, $C_{1-6}$ alkylarylene, amino$C_{1-6}$alkylene- or amino; and
3. F is hetero$C_{3-8}$ cycloalkyl optionally substituted with $C_{1-6}$alkyl;

(iv) $R_4$ is aryl optionally substituted with one or more halo, hydroxy[[1]] or $C_{1-6}$alkoxy[H]; heteroaryl; or heteroC$_{3-6}$ cycloalkyl; and (v) $R_5$ is H, $C_{1-6}$ alkyl, $C_{3-8}$ cycloalkyl, heteroaryl, aryl or p-benzylaryl; wherein "alk", "alkyl", "haloalkyl" or "alkoxy" refers to $C_{1-6}$ alkyl and "cycloalkyl" refers to $C_{3-8}$ cycloalkyl;

in free or salt form.

In one embodiment the invention provides that the PDE1 inhibitors for use in the methods of treatment and prophylaxis described herein are compounds of Formula IX:

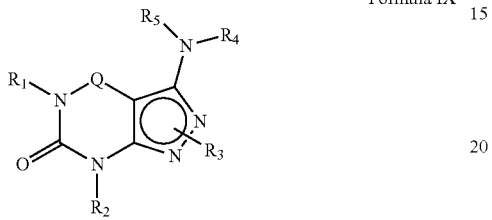

Formula IX wherein
(i) Q is —C(=S)—, —C(=N($R_6$))— or —C($R_{14}$)($R_{15}$)—;
(ii) $R_1$ is H or $C_{1-6}$ alkyl (e.g., methyl or ethyl);
(iii) $R_2$ is
H,
$C_{1-6}$ alkyl (e.g., isopropyl, isobutyl, 2-methylbutyl or 2,2-dimethylpropyl) wherein said alkyl group is optionally substituted with one or more halo (e.g., fluoro) or hydroxy (e.g., hydroxyC$_{1-6}$alkyl, for example 1-hydroxyprop-2-yl or 3-hydroxy-2-methylpropyl),
haloC$_{1-6}$ alkyl (e.g., trifluoromethyl or 2,2,2-trifluoroethyl),
N($R_{14}$)($R_{15}$)—$C_{1-6}$ alkyl (e.g., 2-(dimethylamino)ethyl or 2-aminopropyl),
arylC$_{0-6}$ alkyl (e.g., phenyl or benzyl), wherein said aryl is optionally substituted with one or more $C_{1-6}$ alkoxy, for example, $C_{1-6}$alkoxyarylC$_{0-6}$alkyl (e.g., 4-methoxybenzyl), heteroarylC$_{0-6}$alkyl (e.g., pyridinylmethyl), wherein said heteroaryl is optionally substituted with one or more $C_{1-6}$ alkoxy (e.g., $C_{1-6}$alkoxyheteroarylC$_{1-6}$ alkyl);
G-J wherein G is a single bond or $C_{1-6}$ alkylene (e.g., methylene) and J is $C_{3-8}$ cycloalkyl or heteroC$_{3-8}$ cycloalkyl (e.g., oxetan-2-yl, pyrrolidin-3-yl, pyrrolidin-2-yl) wherein the cycloalkyl and heterocycloalkyl group are optionally substituted with one or more $C_{1-6}$ alkyl or amino, for example,
—C$_{0-4}$ alkyl-$C_{3-8}$ cycloalkyl (e.g., —C$_{0-4}$ alkyl-cyclopentyl, —C$_{0-4}$alkyl-cyclohexyl or —C$_{0-4}$ alkyl-cyclopropyl), wherein said cycloalkyl is optionally substituted with one or more $C_{1-6}$ alkyl or amino (for example, 2-aminocyclopentyl or 2-aminocyclohexyl),
—C$_{0-4}$ alkyl-$C_{3-8}$ heterocycloalkyl (e.g., —C$_{0-4}$ alkyl-pyrrolidinyl, for example, —C$_{0-4}$ alkylpyrrolidin-3-yl) wherein said heterocycloalkyl is optionally substituted with $C_{1-6}$ alkyl (e.g., methyl), for example, 1-methylpyrrolidin-3-yl, 1-methyl-pyrrolidin-2-yl, 1-methyl-pyrrolindin-2-yl-methyl or 1-methyl-pyrrolindin-3-yl-methyl);

(iv) $R_3$ is
1) -D-E-F wherein:
D is a single bond, $C_{1-6}$ alkylene (e.g., methylene), or arylC$_{1-6}$alkylene (e.g., benzylene or —CH$_2$C$_6$H$_4$—);
E is
a single bond,
$C_{1-4}$alkylene (e.g., methylene, ethynylene, prop-2-yn-1-ylene),
$C_{0-4}$ alkylarylene (e.g., phenylene or —C$_6$H$_4$—, -benzylene- or —CH$_2$C$_6$H$_4$—), wherein the arylene group is optionally substituted with halo (e.g., Cl or F),
heteroarylene (e.g., pyridinylene or pyrimidinylene), aminoC$_{1-6}$alkylene (e.g., —CH$_2$N(H)—), amino (e.g., —N(H)—);
$C_{3-8}$ cycloalkylene optionally containing one or more heteroatom selected from N or O (e.g., piperidinylene),
F is
H,
halo (e.g., F, Br, Cl),
$C_{1-6}$ alkyl (e.g., isopropyl or isobutyl),
haloC$_{1-6}$alkyl (e.g., trifluoromethyl),
aryl (e.g., phenyl),
$C_{3-8}$ cycloalkyl optionally containing one or more atom selected from a group consisting of N, S or O (e.g., cyclopentyl, cyclohexyl, piperidinyl, pyrrolidinyl, tetrahydro-2H-pyran-4-yl, or morpholinyl), and optionally substituted with one or more $C_{1-6}$ alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
heteroaryl (e.g., pyridyl (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl)), triazolyl (e.g., 1,2,4-triazol-1-yl), tetrazolyl (e.g., tetrazol-5-yl), alkyloxadiazolyl (e.g., 5-methyl-1,2,4-oxadiazol), wherein said heteroaryl is optionally substituted with one or more $C_{1-6}$ alkyl, halo (e.g., fluoro) or halo $C_{1-6}$alkyl;
$C_{1-6}$ alkoxy,
—O-haloC$_{1-6}$ alkyl (e.g., —O—CF$_3$),
$C_{1-6}$ alkylsulfonyl (for example, methylsulfonyl or —S(O)$_2$CH$_3$),
—C(O)—$R_{13}$, wherein Ria is —N($R_{14}$)($R_{15}$), $C_{1-6}$ alkyl (e.g., methyl), —OC$_{1-6}$ alkyl (e.g., —OCH$_3$), haloC$_{1-6}$ alkyl (trifluoromethyl), aryl (e.g., phenyl), or heteroaryl;
N($R_{14}$)($R_{15}$);
or
2) a substituted heteroarylC$_{1-6}$ alkyl, e.g., substituted with haloC$_{1-6}$alkyl;
or
3) attached to one of the nitrogens on the pyrazolo portion of Formula I and is a moiety of Formula A

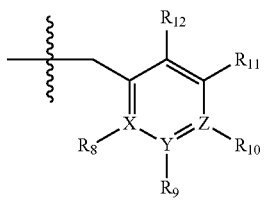

Formula A wherein:
X, Y and Z are, independently, N or C,
$R_8$, $R_9$, $R_{11}$ and $R_{12}$ are independently H or halogen (e.g., Cl or F); and
$R_{10}$ is
  halogen (e.g., fluoro or chloro),
  $C_{1-6}$ alkyl,
  $C_{3-8}$ cycloalkyl,
  heteroC$_{3-8}$ cycloalkyl (e.g., pyrrolidinyl or piperidinyl),
  haloC$_{1-6}$ alkyl (e.g., trifluoromethyl),
  aryl (e.g., phenyl) or heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkyloxadiazolyl (e.g., 5-methyl-1,2,4-oxadiazol), pyrazolyl (e.g., pyrazol-1-yl),
  wherein said aryl, heteroaryl, cycloalkyl or heterocycloalkyl is optionally substituted with one or more $C_{1-6}$alkyl (e.g., methyl), halogen (e.g., chloro or fluoro), haloC$_{1-6}$alkyl (e.g., trifluoromethyl), hydroxy, carboxy, —SH, or an additional aryl or heteroaryl (e.g., biphenyl or pyridylphenyl),
  $C_{1-6}$ alkyl sulfonyl (e.g., methyl sulfonyl), arylcarbonyl (e.g., benzoyl), heteroarylcarbonyl,
  $C_{1-6}$ alkoxycarbonyl, (e.g., methoxycarbonyl),
  Aminocarbonyl,
  —N($R_{14}$)($R_{15}$);
  preferably $R_{10}$ is phenyl, pyridyl, piperidinyl or pyrrolidinyl optionally substituted with the substituents previously defined, e.g. optionally substituted with halo or alkyl;
  provided that when X, Y or X is nitrogen, $R_8$, $R_9$ or $R_{10}$, respectively, is not present;
(v) $R_4$ and $R_5$ are independently:
  H,
  $C_{1-6}$ alkyl (e.g., methyl, isopropyl, isobutyl, n-propyl),
  $C_{3-8}$cycloalkyl (e.g., cyclopentyl or cyclohexyl),
  $C_{3-8}$ heterocycloalkyl (e.g., pyrrolidinyl (for example pyrrolidin-3-yl or pyrrolidin-1-yl), piperidinyl (for example, piperidin-1-yl), morpholinyl),
  —C$_{0-6}$ alkylaryl (e.g., phenyl or benzyl) or
  $C_{0-6}$ alkylheteroaryl (e.g., pyrid-4-yl, pyrid-2-yl or pyrazol-3-yl) wherein said aryl or heteroaryl is optionally substituted with one or more halo (e.g., 4-fluorophenyl), hydroxy (e.g., 4-hydroxyphenyl), $C_{1-6}$ alkyl, $C_{1-6}$ alkoxy or another aryl group (e.g., biphenyl-4-ylmethyl);
(vi) $R_6$ is H, $C_{1-6}$ alkyl (e.g., methyl or ethyl) or $C_{3-8}$ cycloalkyl;
(vii) $R_{14}$ and $R_{15}$ are independently H or $C_{1-6}$ alkyl,
in free or salt form.

In one embodiment the invention provides that the PDE1 inhibitors for use in the methods of treatment and prophylaxis described herein are Formula X, selected from Formula X-A or X-B:

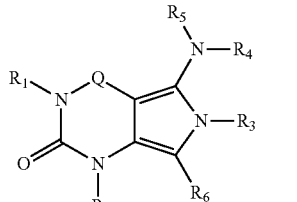

Formula X-A or

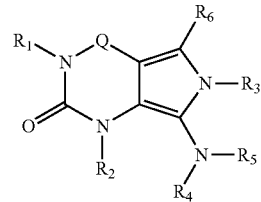

Formula X-B wherein
(i) Q is —C(=S)—, —C(=O)—, —C(=N($R_7$))— or —C($R_{14}$)($R_{15}$)—;
(ii) $R_1$ is H or $C_{1-6}$ alkyl (e.g., methyl or ethyl);
(iii) $R_2$ is H, $C_{1-6}$ alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, $R_2$ may be a trifluoromethyl or 2,2,2-trifluoroethyl, N($R_{14}$)($R_{15}$)— $C_{1-6}$ alkyl (e.g., 2-(dimethylamino)ethyl or 2-aminopropyl), arylC$_{1-6}$ alkyl (e.g., phenyl or benzyl), heteroaryl $C_{1-6}$ alkyl (e.g., pyridinylmethyl), $C_{1-6}$ alkoxyaryl-$C_{1-6}$ alkyl (e.g., 4-methoxybenzyl); -G-J wherein:
  G is a single bond or, alkylene (e.g., methylene); J is cycloalkyl or heterocycloalkyl (e.g., oxetan-2-yl, pyrolyin-3-yl, pyrolyin-2-yl) optionally substituted with one or more $C_{1-6}$ alkyl (e.g., (1-methylpyrolidin-2-yl)), amino (e.g., —NH$_2$), for example, -G-J may be —C$_{0-4}$ alkyl-C$_{3-8}$ cycloalkyl (e.g., cyclopentyl, cyclohexyl or cyclopropylmethyl) optionally substituted with one or more $C_{1-6}$alkyl, amino (e.g., —NH$_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);
(iv) $R_3$ is
  1) -D-E-F wherein:
  D is a single bond, $C_{1-6}$ alkylene (e.g., methylene), or arylalkylene
  (e.g., p-benzylene or —CH$_2$C$_6$H$_4$—);
  E is a single bond,
  $C_{1-6}$alkylene (e.g., methylene) $C_{2-6}$ alkynylene (e.g., ethynylene, prop-2-yn-1-ylene),ethynylene, prop-2-yn-1-ylene), —C$_{0-4}$ alkylarylene (e.g., phenylene or —C$_6$H$_4$—, -benzylene- or —CH$_2$C$_6$H$_4$—), wherein the arylene group is optionally substituted with halo (e.g., Cl or F), heteroarylene (e.g., pyridinylene or pyrimidinylene), aminoC$_{1-6}$ alkylene (e.g., —CH$_2$N(H)—), amino (e.g., —N(H)—);

C$_{3-8}$ cycloalkylene optionally containing one or more heteroatom selected from N or O (e.g., piperidinylene), F is

H, halo (e.g., F, Br, Cl), C$_{1-6}$ alkyl (e.g., isopropyl or isobutyl), haloC$_{1-6}$ alkyl (e.g., trifluoromethyl), aryl (e.g., phenyl), C$_{3-8}$ cycloalkyl optionally containing at least one atom selected from a group consisting of N or O (e.g., cyclopentyl, N cyclohexyl, piperidinyl, pyrrolidinyl, tetrahydro-2H-pyran-4-yl, or morpholinyl), said cycloalkyl is optionally substituted with C$_{1-6}$ alkyl (e.g., methyl or isopropyl), for example, 1-methylpyrrolidin-2-yl, pyrrolidin-1-yl, pyrrolidin-2-yl, piperidin-2-yl, 1-methyrpiperidin-2-yl, 1-ethylpiperidin-2-yl, heteroaryl optionally substituted with C$_{1-6}$ alkyl, (e.g., pyridyl, (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with halo (e.g., fluoro) or haloC$_{1-6}$ alkyl, for example, 6-fluoropyrid-2-yl; amino (e.g., —NH$_2$), C$_{1-6}$ alkoxy, —O-halo C$_{1-6}$alkyl (e.g., —O—CF$_3$), C$_{1-6}$ alkylsulfonyl (for example, methylsulfonyl or —S(O)$_2$CH$_3$), —C(O)—R$_{13}$, —N(R$_{14}$)(R$_{15}$); or 2) a substituted heteroarylalkyl, e.g., substituted with haloalkyl; or 3) attached to the nitrogen on the pyrrolo portion of Formula I and is a moiety of Formula A

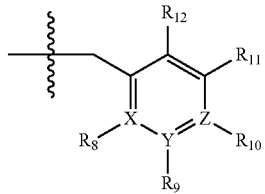

Formula A wherein X, Y and Z are, independently, N or C, and R$_8$, R$_9$, R$_{11}$ and R$_{12}$ are independently H or halogen (e.g., Cl or F); and R$_{10}$ is halogen, C$_{1-6}$ alkyl, C$_{1-6}$alkoxy (e.g., methoxy), C$_{3-8}$ cycloalkyl, heteroC$_{3-8}$ cycloalkyl (e.g., pyrrolidinyl) haloC$_{1-6}$ alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), C$_{1-6}$ alkyl sulfonyl (e.g., methyl sulfonyl), arylcarbonyl (e.g., benzoyl), heteroarylcarbonyl, alkoxycarbonyl, (e.g., methoxycarbonyl), aminocarbonyl; wherein the aryl, heteroaryl, cycloalkyl or heterocycloalkyl is optionally substituted with one or more C$_{1-6}$alkyl (e.g., methyl), halogen (e.g., chloro or fluoro), haloC$_{1-6}$ alkyl (e.g., trifluoromethyl), hydroxy, carboxy, —SH, or an additional aryl or heteroaryl (e.g., biphenyl or pyridylphenyl) preferably R$_{10}$ is phenyl or pyridyl, e.g., 2-pyridyl optionally substituted with the substituents previously defined;

provided that when X, Y or X is nitrogen, R$_8$, R$_9$ or R$_{10}$, respectively, is not present; (v) R$_4$ and R$_5$ are independently H, C$_{1-6}$ alkyl (e.g., methyl, isopropyl), C$_{3-8}$ cycloalkyl (e.g., cyclopentyl), C$_{3-8}$ heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), C$_{1-6}$alkyl, C$_{1-6}$ alkoxy or another aryl group (e.g., biphenyl-4-ylmethyl);

(vi) R$_6$ is H, C$_{1-6}$ alkyl (e.g., methyl), hydroxy, C$_{1-6}$ alkoxy, aryloxy, —N(R$_{16}$)(R$_{17}$), oxo (e.g., =O), or C$_{3-8}$Cycloalkyl;

(vii) R$_7$ is H, C$_{1-6}$ alkyl (e.g., methyl) or C$_{3-8}$ cycloalkyl wherein said cycloalkyl is optionally substituted with one or more oxo (e.g., 2,5-dioxopyrrolidin-1-yl);

(viii) R$_{13}$ is —N(R$_{14}$)(R$_{15}$), C$_{1-6}$ alkyl (e.g., methyl), —OC$_{1-6}$ alkyl (e.g., —OCH$_3$), haloC$_{1-6}$alkyl (trifluoromethyl), aryl (e.g., phenyl), or heteroaryl; and (ix) R$_{14}$ and R$_{15}$ are independently H or C$_{1-6}$ alkyl;

(x) R$_{16}$ and R$_{17}$ are independently H, C$_{1-6}$ alkyl, aryl (e.g., phenyl), heteroaryl, wherein said aryl or heteroaryl is optionally substituted with halo (e.g., fluoro), C$_{1-6}$ alkoxy (e.g., methoxy); in free or salt form.

In one embodiment the invention provides that the PDE1 inhibitors for use in the methods of treatment and prophylaxis described herein are Formula XI:

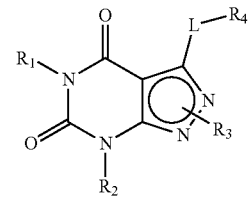

Formula XI wherein
(i) L is S, SO or SO$_2$;
(ii) R$_2$ is H or C$_{1-6}$ alkyl (e.g., methyl or ethyl);
(iii) R$_2$ is

H,

C$_{1-6}$ alkyl (e.g., isopropyl, isobutyl, neopentyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), —C$_{0-4}$alkyl-C$_{3-8}$cycloalkyl (e.g., cyclopentyl, cyclohexyl) optionally substituted with one or more amino (e.g., —NH$_2$), for example, 2-aminocyclopentyl or 2-aminocyclohexyl), wherein said cycloalkyl optionally contains one or more heteroatom selected from N and O and is optionally substituted with C$_{1-6}$ alkyl (e.g., 1-methyl-pyrrolindin-2-yl, 1-methyl-pyrrolindin-3-yl, 1-methyl-pyrrolindin-2-yl-methyl or 1-methyl-pyrrolindin-3-yl-methyl), C$_{3-8}$heterocycloalkyl (e.g., pyrrolidinyl, for example, pyrrolidin-3-yl) optionally substituted with C$_{1-6}$ alkyl (e.g., methyl), for example, 1-methylpyrrolidin-3-yl, C$_{3-8}$cycloalkyl-C$_{1-6}$alkyl (e.g., cyclopropylmethyl), haloC$_{1-6}$ alkyl (e.g., trifluoromethyl, 2,2,2-trifluoroethyl), —N(R$_{14}$)(R$_{15}$)—C$_{1-6}$alkyl (e.g., 2-(dimethylamino)ethyl, 2-aminopropyl), hydroxyC$_{1-6}$alkyl (e.g., (e.g., 3-hydroxy-2-methylpropyl, 1-hydroxyprop-2-yl), arylC$_{0-6}$alkyl (e.g., benzyl), heteroarylC$_{1-6}$alkyl (e.g., pyridinylmethyl), C$_{1-6}$alkoxyarylC$_{1-6}$alkyl (e.g., 4-methoxybenzyl); -G-J wherein: G is a single bond or, alkylene (e.g., methylene);

J is cycloalkyl or heterocycloalkyl (e.g., oxetan-2-yl, pyrolyin-3-yl, pyrolyin-2-yl) optionally substituted with C$_{1-6}$alkyl (e.g., (1-methylpyrolidin-2-yl));

(iv) R$_3$ is attached to one of the nitrogens on the pyrazolo portion of Formula I and is a moiety of Formula A

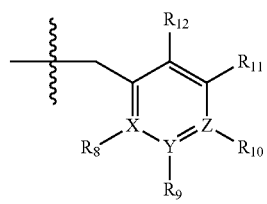

Formula A wherein X, Y and Z are, independently, N or C, and R$_8$, R$_9$, R$_{11}$ and R$_{12}$ are independently H or halogen (e.g., Cl or F); and R$_{10}$ is halogen, C$_{1-6}$ alkyl, C$_{3-8}$ cycloalkyl, heteroC$_{3-8}$ cycloalkyl (e.g., pyrrolidinyl or piperidinyl) haloC$_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-15 yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-i-yi), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl, pyridyl, e.g., 2-pyridyl, piperidinyl, or pyrrolidinyl; wherein the aryl, heteroaryl cycloalkyl or heterocycloalkyl is optionally substituted with one or more halo (e.g., F or Cl), C$_{1-6}$ alkyl, C$_{1-6}$ alkoxy, C$_{1-4}$haloalkyl (e.g., trifluoromethyl), and/or —SH, provided that when X, Y or X is nitrogen, R$_8$, R$_9$ or R$_{10}$, respectively, is not present;

(v) R$_4$ is

H, C$_{1-6}$ alkyl (e.g., methyl, isopropyl),

C$_{3-8}$ cycloalkyl (e.g., cyclopentyl), C$_{3-8}$ heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), C$_{1-6}$ alkyl, C$_{1-6}$ alkoxy or another aryl group (e.g., biphenyl-4-ylmethyl);

(vi) R$_{10}$ and R$_{15}$ are independently H or C$_{1-6}$ alkyl, in free or salt form.

In yet another embodiment the invention provides that the PDE1 inhibitors for use in the methods of treatment and prophylaxis described herein are Formula XII:

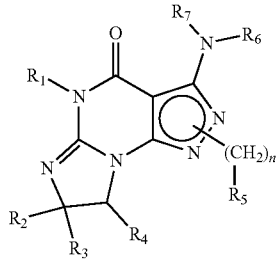

Formula XII wherein (i) R 1 is H or C 1-4 alkyl (e.g., methyl or ethyl);

(ii) R 2 and R 3 are independently H or C 1-6 alkyl (e.g., methyl or ethyl);

(iii) R 4 is H or C 1-4 alkyl (e.g., methyl or ethyl);

(iv) R 5 is aryl (e.g., phenyl) optionally substituted with one or more groups independently selected from —C(=O)— C 1-6 alkyl (e.g., —C(=O)— CH 3) and C 1-6-hydroxyalkyl (e.g., 1-hydroxyethyl);

(v) R 6 and R 7 are independently H or aryl (e.g., phenyl) optionally substituted with one or more groups independently selected from C 1-6 alkyl (e.g., methyl or ethyl) and halogen (e.g., F or Cl), for example unsubstituted phenyl or phenyl substituted with one or more halogen (e.g., F) or phenyl substituted with one or more C 1-6 alkyl and one or more halogen or phenyl substituted with one C 1-6 alkyl and one halogen, for example 4-fluorophenyl or 3,4-difluorophenyl or 4-fluoro-3-methylphenyl;

and (vi) n is 1, 2, 3, or 4, in free or salt form.

The invention further provides the use of PDE1 inhibitors of any of the preceding formulae (e.g., Formula I, II, III, IV, V, VI, VII, VIII, IX, X, XI, XII), wherein the compound is selected from any of the following:

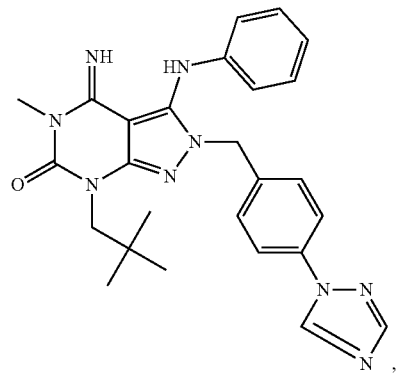

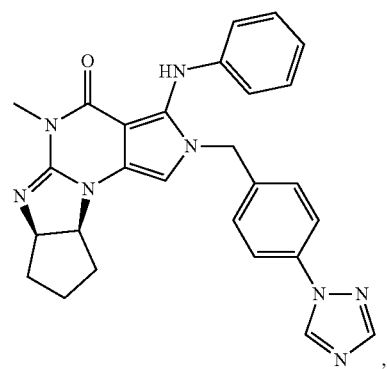
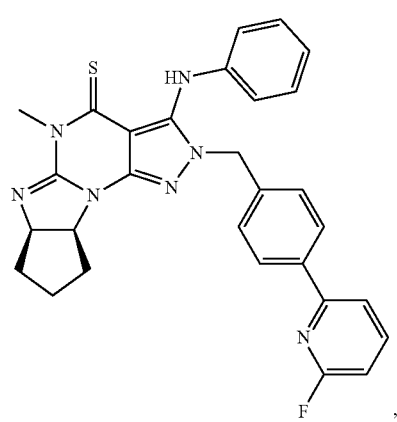
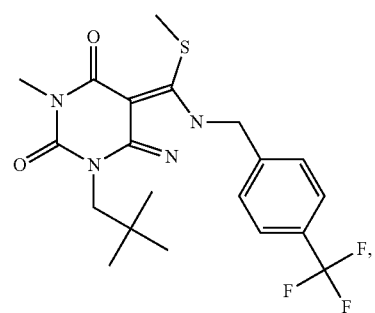
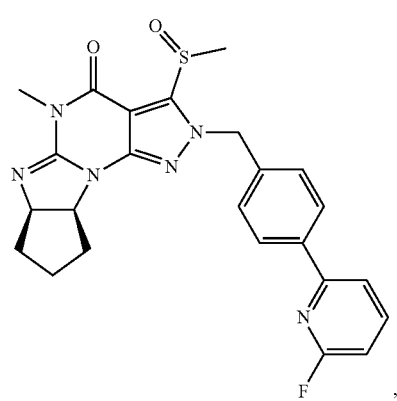
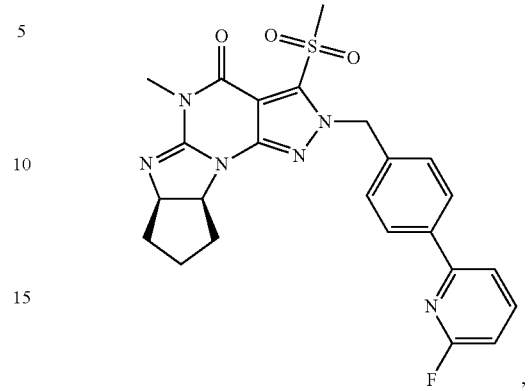
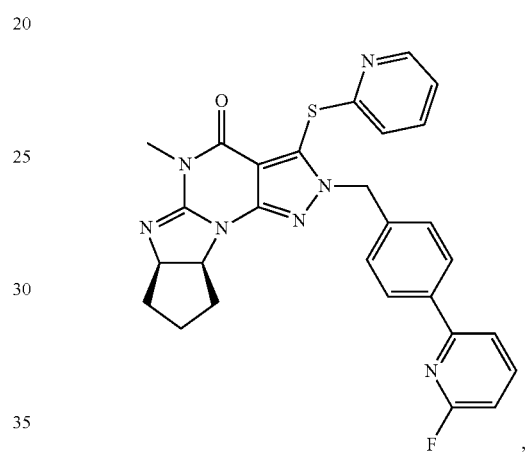
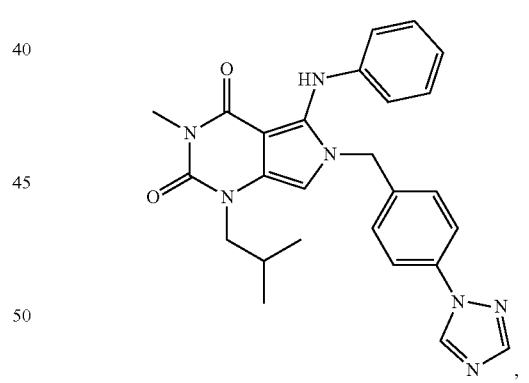
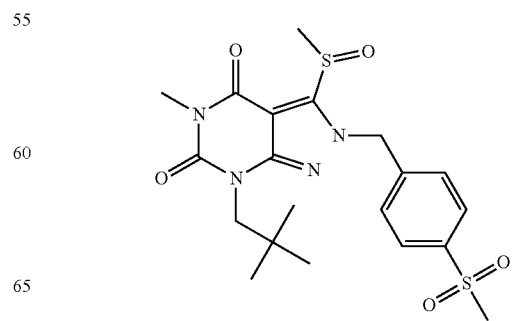

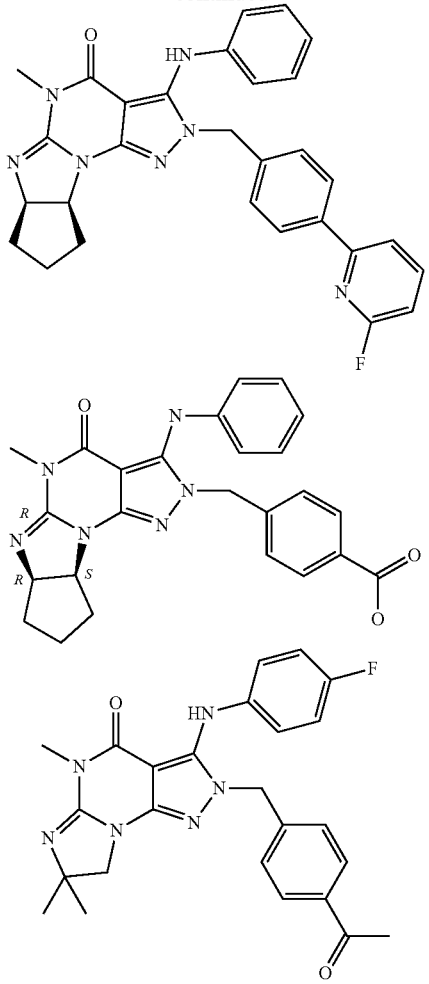

In one embodiment the invention provides administration of a PDE1 inhibitor for treatment or prophylaxis of inflammation or an inflammatory related disease or disorder, wherein the inhibitor is a compound according to the following:

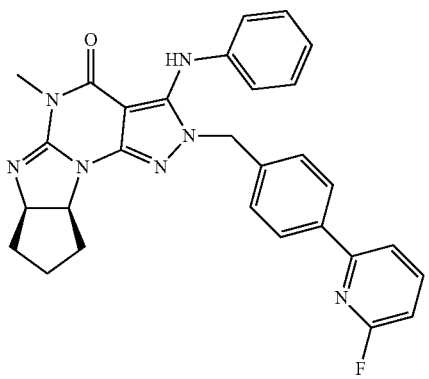 [SMILES: CN1C(=O)c2c(nn(Cc3ccc(-c4cccc(F)n4)cc3)c2Nc2ccccc2)N2C1=N[C@@H]1CCC[C@@H]12]

In still another embodiment, the invention provides administration of a PDE1 inhibitor for treatment or prophylaxis of inflammation or an inflammatory related disease or disorder, wherein the inhibitor is a compound according to the following:

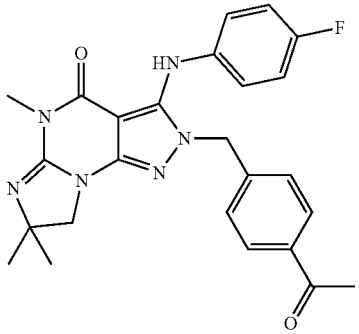 [SMILES: CC(=O)c1ccc(Cn2nc3c(c2Nc2ccc(F)cc2)C(=O)N(C)C2=NC(C)(C)CN23)cc1]

In one embodiment, selective PDE1 inhibitors of the any of the preceding formulae (e.g., Formula I, II, III, IV, V, VI, VII, VIII, IX, X, XI, XII) are compounds that inhibit phosphodiesterase-mediated (e.g., PDE1-mediated, especially PDE1B-mediated) hydrolysis of cGMP, e.g., the preferred compounds have an $IC_{50}$ of less than 1 µM, preferably less than 500 nM, preferably less than 50 nM, and preferably less than 5 nM in an immobilized-metal affinity particle reagent PDE assay, in free or salt form.

If not otherwise specified or clear from context, the following terms herein have the following meanings:

"Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

"Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

"Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

"Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

"Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

For ease of reference, the atoms on the pyrazolo-pyrimidine core of the Compounds of the Invention are numbered in accordance with the numbering depicted in below for Formula I, unless otherwise noted or evident from the context.

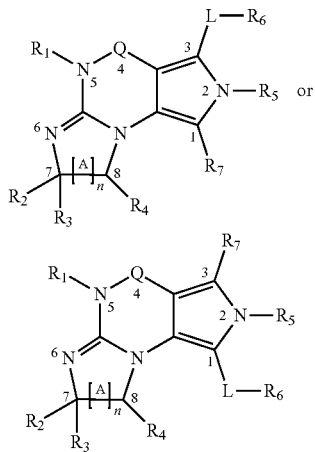

When E is phenylene, the numbering is as follows:

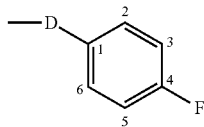

It is intended that wherein the substituents end in "ene", for example, alkylene, phenylene or arylalkylene, said substitutents are intended to bridge or be connected to two other substituents. Therefore, methylene is intended to be —CH$_2$— and phenylene intended to be —C$_6$H$_4$— and arylalkylene is intended to be —C$_6$H$_4$—CH$_2$— or —CH$_2$—C$_6$H$_4$—.

Compounds of the Invention, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula I (Formula I-A and I-B), or a Compound of Formula II (e.g., II-A or II-B), may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrimidine-4(5H)-thione compounds, e.g., Compounds of Formula III, or Compound of Formula IV as described herein, may exist in free or salt form, e.g., as acid addition salts.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—C$_{1-4}$alkyl, can hydrolyze in the body to form physiologically hydrolysable alcohol (Compound-OH) on the one hand and acid on the other (e.g., HOC(O)—C$_{1-4}$ alkyl). Alternatively, wherein the Compound of the Invention contains a carboxylic acid, for example, Compound-C(O)OH, the acid ester prodrug of such compound, Compound-C(O)O—C$_{1-4}$ alkyl can hydrolyze to form Compound-C(O)OH and HO—C$_{1-4}$ alkyl. As will be appreciated the term thus embraces conventional pharmaceutical prodrug forms.

In another embodiment, the invention further provides a pharmaceutical composition comprising a Compound of the Invention, in free or pharmaceutically acceptable salt form, in admixture with a pharmaceutically acceptable carrier, for use as an anti-inflammatory agent.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—C$_{1-4}$alkyl, can hydrolyze in the body to form physiologically hydrolysable alcohol (Compound-OH) on the one hand and acid on the other (e.g., HOC(O)—C$_{1-4}$ alkyl). Alternatively, wherein the Compound of the Invention contains a carboxylic acid, for example, Compound-C(O)OH, the acid ester prodrug of such compound, Compound-C(O)O—C$_{1-4}$ alkyl can hydrolyze to form Compound-C(O)OH and HO—C$_{1-4}$ alkyl. As will be appreciated the term thus embraces conventional pharmaceutical prodrug forms.

In another embodiment, the invention further provides a pharmaceutical composition comprising a Compound of the Invention, in free, pharmaceutically acceptable salt or prodrug form, in admixture with a pharmaceutically acceptable carrier, for use as an anti-inflammatory agent.

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, and U.S. Pat. No. 9,073,936, the contents of each of which herein are hereby incorporated by reference in their entireties.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

Terms and Abbreviations

BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid
THF=tetrahedrofuran.

Methods of Using Compounds of the Invention

The Compounds of the Invention are useful in the treatment of inflammatory diseases or conditions, particularly neuroinflammatory diseases or conditions. Therefore, administration or use of a preferred PDE1 inhibitor as described herein, e.g., a PDE1 inhibitor as hereinbefore described, e.g., a Compound of Formula Ia, Ib, IIa, IIb, III, IV, V, VI, VII, VIII, IX, X, XI, XII provides a means to regulate inflammation (e.g., prevent, reduce, and/or reverse neuroinflammation, and diseases or disorders related to neuroinflammation), and in certain embodiments provide a treatment for various inflammatory diseases and disorders.

For example, in one embodiment the invention provides a method (Method 1) of treatment or prophylaxis of inflammation or disease associated with inflammation comprising administering an effective amount of a specific inhibitor of phosphodiesterase type I (PDE1), to a patient in need thereof, for example:

1.1 Method 1 which is a method of treating neuroinflammation and/or diseases or disorders associated with neuroinflammation and/or microglial function.
1.2 Method 1 or 1.1 wherein the disease or condition to be treated is selected from:
   a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;
   b. stroke, cardiac arrest, hypoxia, intracerebral hemorrhage or traumatic brain injury;
   c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and d. chronic CNS infections, e.g., Lyme disease or CNS infection consequent to an immunosuppressive condition, e.g., HIV-dementia;
e. neuroinflammation consequent to chemotherapy; comprising administering an effective amount of a PDE1 inhibitor of the current invention (e.g., a PDE1 inhibitor of Formula I, II, III, IV, V, VI, VII, VIII, IX, X, XI, and/or XII as herein described), e.g., an amount effective to (i) reduce or inhibit activation of M1 microglia, and/or (ii) and amount effective to reduce levels of one or more pro-inflammatory cytokines (e.g., IL1β, TNF-α, and Ccl2, or combination thereof); to a patient in need thereof.

1.3. Any foregoing method wherein the disease or condition to be treated is a neurodegenerative conditions, e.g., selected from Alzheimer's disease (AD), Parkinson's disease (PD), amyotrophic lateral sclerosis (ALS), and demyelinating conditions, e.g., multiple sclerosis (MS), and prion diseases.

1.4. Any foregoing method wherein the disease or condition to be treated is selected from stroke, cardiac arrest, hypoxia, intracerebral hemorrhage and traumatic brain injury.

1.5. Any foregoing method wherein the disease or condition to be treated is a condition characterized by abnormal neurotransmitter production and/or response, e.g., selected from depression, schizophrenia, post-traumatic stress disorder, anxiety, attention deficit disorder, and bipolar disease; e.g., wherein any of the foregoing are associated with neuroinflammation.

1.6. Any foregoing method wherein the disease or condition to be treated is selected from chronic CNS infections, e.g., Lyme disease or CNS infection consequent to an immunosuppressive condition, e.g., HIV-dementia.

1.7. Any foregoing method wherein the disease or condition to be treated is neuroinflammation consequent to chemotherapy.

1.8. Any foregoing method comprising administering an effective amount of a PDE1 inhibitor of the current invention (e.g., a PDE1 inhibitor of Formula I, II, III, IV, V, VI, VII, VIII, IX, X, XI, and/or XII as herein described), e.g., an amount effective to (i) reduce or inhibit activation of M1 microglia, and/or (ii) and amount effective to reduce levels of one or more pro-inflammatory cytokines (e.g., IL1β, TNF-α, IL6 and Ccl2, or combination thereof); to a patient in need thereof.

1.9. Any foregoing method comprising administering an effective amount of a PDE1 inhibitor of the current invention (e.g., a PDE1 inhibitor of Formula I, II, III, IV, V, VI, VII, VIII, IX, X, XI, and/or XII as herein described) to a patient in need thereof, in an amount effective to anti-inflammatory cytokines (e.g., IL-10).

1.10. Any foregoing method comprising administering an effective amount of a PDE1 inhibitor of the current invention (e.g., a PDE1 inhibitor of Formula I, II, III, IV, V, VI, VII, VIII, IX, X, XI, and/or XII as herein described) to a patient in need thereof, in an amount effective to reduce levels of microglial M1 phenotype and/or enhance levels of microglial M2 phenotype.

1.11. Any foregoing method wherein the PDE1 inhibitor is a Compound of Formula Ia, Ib, IIa, IIb, III, IV, V, VI, VII, VIII, IX, X, XI, XII.

1.12. Any foregoing method wherein the neuroinflammation is associated with increased expression and/or activation of microglial cells (e.g., M1 microglial cells) in the brain.

1.13. Any foregoing method wherein the PDE1 inhibitor blunts or inhibits the expression and/or activity of pro-inflammatory cytokines in the brain, e.g., selected from the group consisting of: IL1B, IL-6, TNF-α, Ccl2, Nitric Oxide (NO), and Reactive Oxygen Species (ROS).

1.14. Any foregoing method wherein the PDE1 inhibitor in administered in combination with a PDE4 inhibitor (e.g., rolipram).

1.15. Any foregoing method wherein the patient exhibits increased levels of pro-inflammatory cytokines (e.g., IL1B, IL6, TNF-alpha, Ccl2).

1.16. Any foregoing method wherein "PDE1 inhibitor" describes a compound(s) which selectively inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay.

1.17. Any foregoing method wherein the PDE1 inhibitor inhibits the activity of PDE1 (e.g., bovine PDE1 in the assay described in Example 1) with an $IC_{50}$ of less than 10 nM, e.g., wherein the PDE1 inhibitor does not inhibit the activity of PDE types other than PDE1, e.g., has an $IC_{50}$ at least 1000 times greater for PDE types other than PDE1.

1.18. Any foregoing method, wherein the PDE1 inhibitor is selected from any of the following:

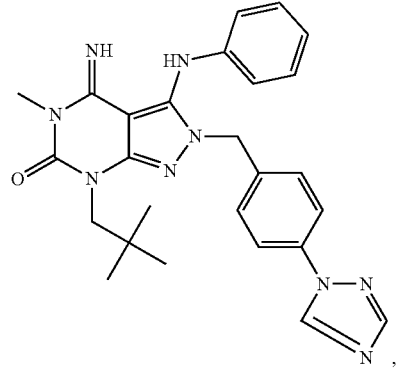

,

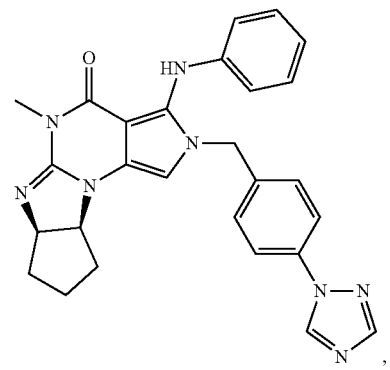

,

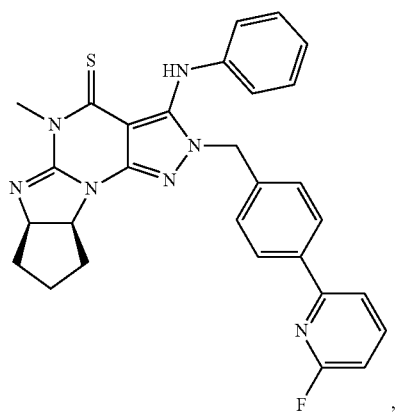
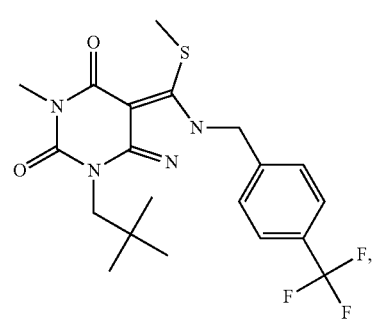
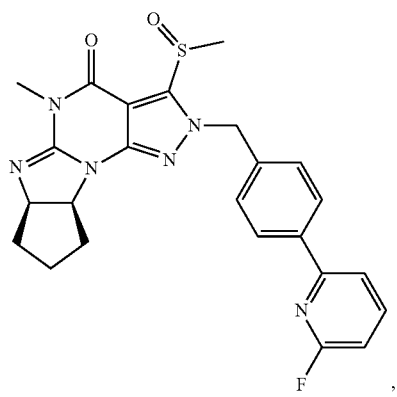
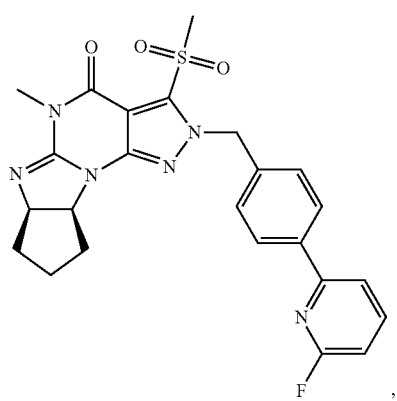
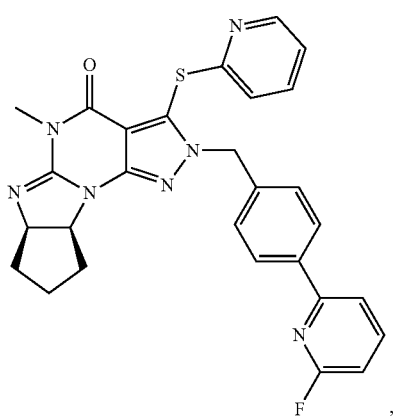
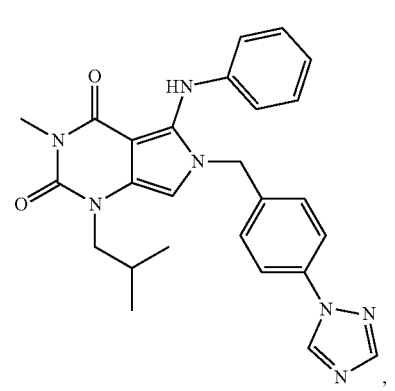
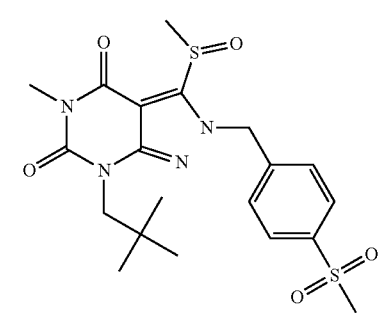
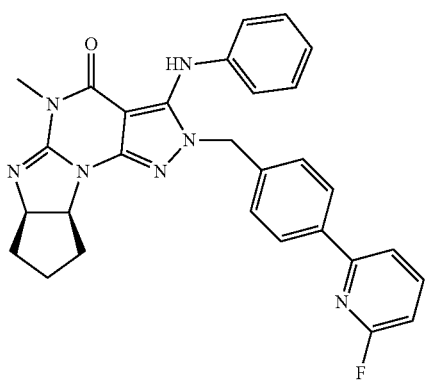

-continued

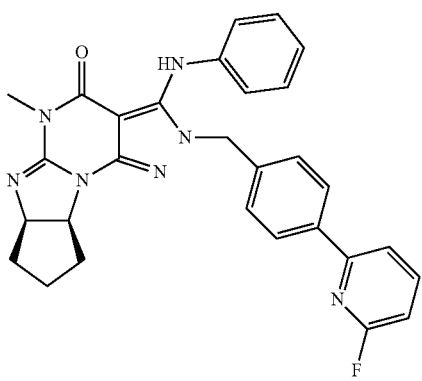

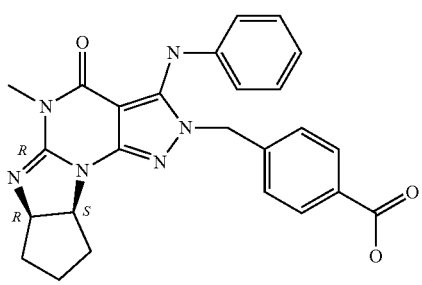

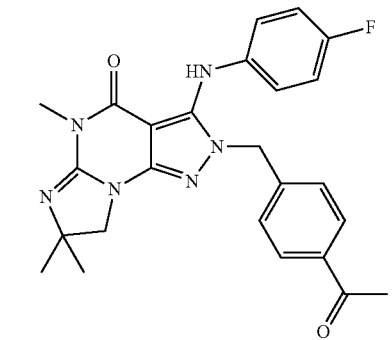

1.19. Any foregoing method, wherein the PDE1 inhibitor is the following:

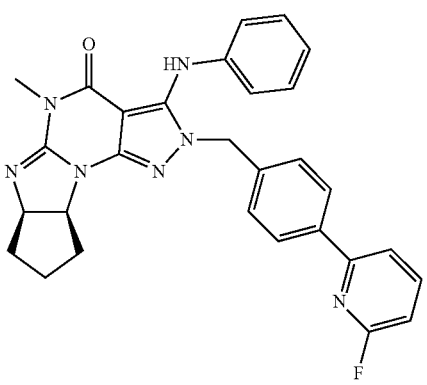 [SMILES: CN1C(=O)c2c(nn(Cc3ccc(-c4cccc(F)n4)cc3)c2Nc2ccccc2)N2C1=N[C@@H]1CCC[C@@H]12]

1.20. Any foregoing method, wherein the PDE1 inhibitor is the following:

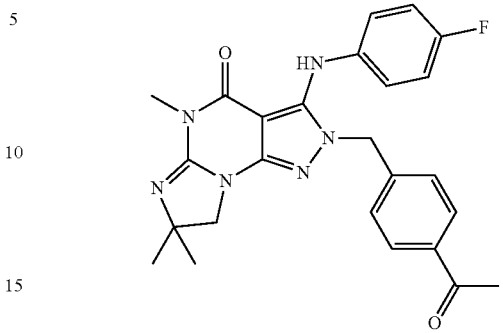

1.21. Any foregoing method, wherein the PDE1 inhibitor is administered in combination (e.g. administered sequentially or simultaneously or within a 24 hour period) with an effective amount of one or more antidepressant agents, e.g., with one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from
(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
d) Atypical antipsychotics, e.g., Aripiprazole (Abilify), Asenapine (Saphris), Brexpiprazole (Rexulti), Clozapine (Clozaril), Lumateperone, Lurasidone (Latuda), Olanzapine (Zyprexa), Paliperidone (Invega), Quetiapine (Seroquel), Risperidone (Risperdal), Sertindole (Serdolect, Serlect) Ziprasidone (Geodon)

1.22. Method 1.21 wherein the antidepressant agent is an atypical antipsychotic agent, e.g., Lumateperone, in free or pharmaceutically acceptable salt form.

1.23. Method 1.21 wherein the antidepressant agent is an SSRI, e.g., Fluoxetine or Escitalopram, in free or pharmaceutically acceptable salt form.

1.24. Any of the foregoing method wherein the patient has elevated levels of one or more pro-inflammatory cytokines (e.g., selected from IL1β, TNFα, Ccl2, IL-6, and combinations thereof).

1.25. Any of the foregoing method wherein the patient has reduced levels of one or more anti-inflammatory cytokines (e.g., IL-10).

1.26. Any of the foregoing method wherein the patient has elevated levels of microglial M1 phenotype compared to microglial M2 phenotype.

1.27. Any of the foregoing methods, wherein the patient has abnormal levels (e.g., abnormal levels relative to a reference standard) of one or more of the cytokines described in FIG. 10 or FIG. 11.

1.28. Any of the foregoing methods, wherein the PDE1 inhibitor is administered to treat or prevent chronic neuroinflammation or a disease associated with chronic neuroinflammation.

1.29. Any of the foregoing methods, wherein the PDE1 inhibitor is administered to a patient with an optic nerve injury.

1.30. The method of 1.29, wherein the PDE1 inhibitor increases expression of PDE1 in retinal ganglion.

1.31. The method of 1.29 or 1.30, wherein the administration of the PDE1 inhibitor increases the survival of retinal ganglion cells (e.g., increased as compared to a reference standard or control).

The invention further provides the use of a PDE1 inhibitor, e.g., any of a Compound of Formula I, Formula II, Formula III, Formula IV, Formula V, Formula VI, Formula VII, Formula VIII, Formula IX, Formula X, Formula XI, or Formula XII in the manufacture of a medicament for use in any of Methods 1, et seq.

The invention further provides a PDE1 inhibitor, e.g., any of a Compound of Formula I, Formula II, Formula III, Formula IV, Formula V, Formula VI, Formula VII, Formula VIII, Formula IX, Formula X, Formula XI, or Formula XII for use in any of Methods 1, et seq.

The invention further provides a pharmaceutical composition comprising a PDE1 inhibitor, e.g., any of a Compound of Formula I, Formula II, Formula III, Formula IV, Formula V, Formula VI, Formula VII, Formula VIII, Formula IX, Formula X, Formula XI, or Formula XII for use in any of Methods 1 et seq.

The phrase "Compounds of the Invention" or "PDE 1 inhibitors of the Invention", or like terms, encompasses any and all of the compounds disclosed herewith, e.g., a Compound of Formula I, Formula II, Formula III, Formula IV, Formula V, Formula VI, Formula VII, Formula VIII, Formula IX, Formula X, Formula XI, or Formula XII.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat or mitigate a specific disease or disorder, and/or a symptom thereof, and/or to reduce inflammatory cytokines, e.g., as produced by microglia, and/or to reduce M1 microglia activation, and/or to increase anti-inflammatory cytokines, e.g., as produced by microglia, and/or to enhance M2 microglia activation.

The term "patient" includes a human or non-human (i.e., animal) patient. In a particular embodiment, the invention encompasses both humans and nonhuman animals. In another embodiment, the invention encompasses nonhuman animals. In other embodiments, the term encompasses humans.

The term "comprising" as used in this disclosure is intended to be open-ended and does not exclude additional, unrecited elements or method steps.

Compounds of the Invention, e.g., Formula I, II, III, IV, V, VI, VII, VIII, IX, X, XI, and XII as hereinbefore described, in free or pharmaceutically acceptable salt form, may be used as a sole therapeutic agent, but may also be used in combination or for co-administration with other active agents.

For example, in certain embodiments, the Compounds of the Invention, e.g., Formula I, II, III, IV, V, VI, VII, VIII, IX, X, XI, and XII as hereinbefore described, in free or pharmaceutically acceptable salt form, may be administered in combination (e.g. administered sequentially or simultaneously or within a 24 hour period) with other active agents, e.g., with one or more antidepressant agents, e.g., with one or more compounds in free or pharmaceutically acceptable salt form, selected from selective serotonin reuptake inhibitors (SSRIs),) serotonin-norepinephrine reuptake inhibitors (SNRIs), c) tricyclic antidepressants (TCAs), and atypical antipsychotics.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg (depending on the drug to be administered and the condition to be treated, for example in the case of Compound 214, 0.5 to 25 mg, e.g., 1 to 10 mg, per diem, e.g., in monophosphate salt form, for treatment of neuroinflammatory conditions), conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg (e.g., 1, 2.5, 5, 10, or 20 mg) of a Compound of the Invention, e.g., together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

Example 1

Measurement of PDEIB Inhibition In Vitro Using IMAP Phosphodiesterase Assay Kit

Phosphodiesterase I B (PDEIB) is a calcium/calmodulin dependent phosphodiesterase enzyme that converts cyclic guanosine monophosphate (cGMP) to 5'-guanosine monophosphate (5'-GMP). PDEIB can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Amp). Inhibition of phosphodiesterase, therefore, is detected as a decrease in Amp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: The following phosphodiesterase enzymes may be used: 3',5'-cyclic-nucleotide-specific bovine brain phosphodiesterase (Sigma, St. Louis, Mo.) (predominantly PDE1B) and recombinant full length human PDE1 A and PDE1B (r-hPDE1 A and r-hPDE1B respectively) which may be produced e.g., in HEK or SF9 cells by one skilled in the art. The PDE1 enzyme is reconstituted with 50% glycerol to 2.5 U/ml. One unit of enzyme will hydrolyze 1.0 μm of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μL of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Amp).

A decrease in GMP concentration, measured as decreased Amp, is indicative of inhibition of PDE activity. IC50 values are determined by measuring enzyme activity in the presence of 8 to 16 concentrations of compound ranging from 0.0037 nM to 80,000 nM and then plotting drug concentration versus AmP, which allows IC50 values to be estimated using nonlinear regression software (XLFit; IDBS, Cambridge, Mass.).

The Compounds of the Invention are tested in an assay as described or similarly described herein for PDE1 inhibitory activity. For example, Compound 214, is identified as a specific PDE1 inhibitor of formula:

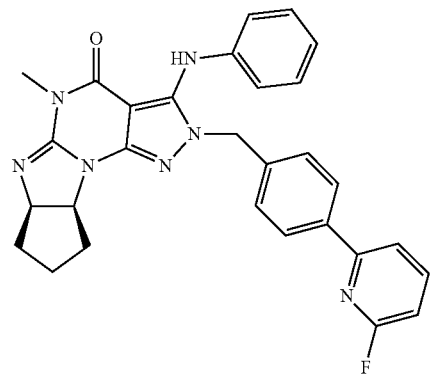 [SMILES: CN1C(=O)c2c(nn(Cc3ccc(-c4cccc(F)n4)cc3)c2Nc2ccccc2)N2C1=N[C@@H]1CCC[C@@H]12]

This compound has efficacy at sub-nanomolar levels vs PDE1 ($IC_{50}$ of 0.058 nM for bovine brain PDE1 in the assay described above) and high selectivity over other PDE families, as depicted on the following table:

| PDE Target | IC50 (nM) | ratio PDEx/PDE1 |
| --- | --- | --- |
| bovine brain PDE1 | 0.058 | 1 |
| hPDE2A | 3661 | 63121 |
| hPDE3B | 3120 | 53793 |
| hPDE4A | 158 | 2724 |
| r-bovine PDE5A | 632 | 10897 |
| bovine retina PDE6 | 324 | 5586 |
| hPDE7B | 355 | 6121 |
| hPDE8A | 3001 | 51741 |
| hPDE9A | 16569 | 285672 |
| hPDE10A | 1824 | 31448 |
| hPDE11A | 1313 | 22638 |

The compound is also highly selective versus a panel of 63 receptors, enzymes, and ion channels. These data, and data for other PDE1 inhibitors described herein, are described in Li et al., J. Med. Chem. 2016: 59, 1149-1164, the contents of which are incorporated herein by reference.

Example 2

Inhibition of Monocyte to Activated Macrophage Transition and Interaction with ANP PDE1 is induced in the inflammatory monocyte-to-activated-macrophage transition mediated by GM-CSF, and this transition can be inhibited by PDE1 knockdown. Bender and Beavo, 2006 PNAS 103, 460-5. Atrial natriuretic peptide (ANP) elevates cGMP levels, by activating the ANP catalytic receptor, which stimulates intracellular guanylyl cyclase activity to convert GTP to cGMP. ANP has an anti-inflammatory effect on macrophages, reducing the secretion of inflammatory mediators in macrophages. Kiemer, et al., Ann Rheum Dis. 2001 November; 60 (Suppl 3): iii68-iii70. Specifically, ANP inhibits the lipopolysaccharide (LPS)-induced expression of inducible nitric oxide synthase (iNOS) in macrophages, reduces the activation of NF-κB, inhibits the macrophage release of TNFα and interleukin 1β (IL1β), but not secretion of the anti-inflammatory cytokines IL10 and IL1 receptor antagonist (ILlra).

We have shown that there is a synergistic effect between ANP and PDE1 inhibition. An immortalized human promyeloid cell line (HL60 from ATCC) is grown, differentiated and harvested as described in Bender, A T, and Beavo, J A, 2006, PNAS 103, 460-465. The cells are grown in HEPES buffered RPMI 1640 medium with penicillin, streptomycin, and 10% fetal bovine serum. Phorbol-12-myristate-13-acetate (PMA), at 100 nM for 3 days, is used to differentiate the HL60 cells into macrophage-like cells. Following differentiation, the cells are incubated with a PDE1 inhibitor or vehicle (DMSO) beginning at time 0. At 40 minutes, 5 µM ionomycin (a calcium ionophore) is added. At 50 minutes, 100 nM ANP was added. At 60 minutes, the cells are harvested. Total cGMP levels are measured using a competitive ELISA (Bender and Beavo, 2006).

A representative PDE1 inhibitor, (6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one, disclosed as Example 20 of U.S. Pat. No. 8,273,750, having the following structure:

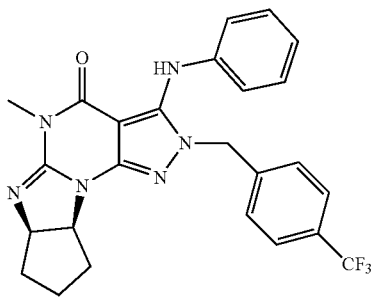 [SMILES: CN1C(=O)c2c(nn(Cc3ccc(C(F)(F)F)cc3)c2Nc2ccccc2)N2C1=N[C@@H]1CCC[C@@H]12]

is tested for its effect on cGMP levels in this system Like Compound 214, this compound is a potent and selective inhibitor of PDE1 (Ki=0.68 nM bovine brain PDE1 assay described above). The cGMP level induced in the HL60 cells by treatment with 100 nM ANP in combination with 100 nM of the PDE1 inhibitor is greater than that induced by either the ANP alone or the PDE1 inhibitor alone. In addition, the cGMP level attained by co-treatment with ANP and the PDE1 inhibitor is much greater than that obtained by co-treatment with ANP and a mixed PDE1/PDE5 inhibitor, SCH 51866 (used at 5 µM). In this experiment, the calcium ionophore ionomycin (used at 5 µM) is used to raise the intracellular calcium level and to counteract the cGMP rise induced by ANP. The decreasing cGMP signal caused by the activation of PDE1 by ionomycin is synergistically prevented by the combination of a PDE1 inhibitor and suboptimal levels of ANP. Addition of ionomycin has only a weak cGMP lowering effect when combined with ANP and the PDE1 inhibitor.

Example 3

Effect of PDE1 Inhibitors on Microglia-Derived Cells

Neuroinflammatory processes are regulated largely by microglia. Microglia have activation states somewhat similar to macrophages and in response to IFN-γ or lipopolysaccharide (LPS), they will be activated to release pro-inflammatory cytokines such as TNF-, IL-1β, and reactive oxygen species/reactive nitrogen species (ROS/NOS). Under other circumstances, they can be activated to release anti-inflammatory cytokines, such as IL-10, and to participate in tissue repair. The immortalized murine microglial cell line BV-2 is used as a model for microglia signaling. Stansley et al. Journal of Neuroinflammation 2012, 9:115.

BV2 cells are treated with lipopolysaccharide (LPS) and the level of expression of PDE expression is measured using RNAseq analysis. The data are presented in FIG. 1. "FPKM" represents the "Fragment Reads per kilobase of exon per million reads mapped". After treatment with LPS, an endotoxin associated with the inflammatory response, levels of PDE1B, show relatively large increases in RNA expression when compared to other members of the PDE family of enzymes. PDE1B is among the phosphodiesterase subfamilies to show large increases in RNA expression upon LPS administration.

BV2 cells are further assessed by RNAseq analysis with LPS stimulation in the presence or absence of rolipram (a specific PDE4 inhibitor), and in the presence or absence of Compound 214, which is a specific PDE1 inhibitor of formula:

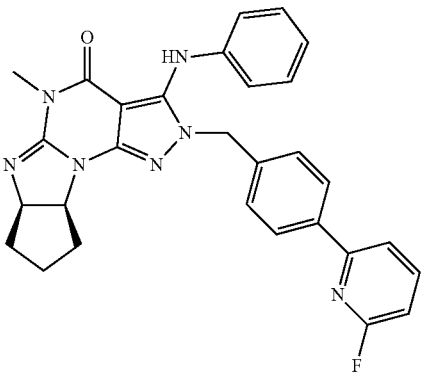 [SMILES: CN1C(=O)c2c(nn(Cc3ccc(-c4cccc(F)n4)cc3)c2Nc2ccccc2)N2C1=N[C@@H]1CCC[C@@H]12]

209 mRNA transcripts are decreased in the presence of LPS+rolipram vs. LPS alone; 138 transcripts are decreased in the presence of Compound 214+LPS vs. LPS alone. The overlap between the two sets is 48 transcripts. Similarly 156 transcripts are elevated in the presence of LPS+rolipram vs. LPS alone; 149 transcripts are elevated in the presence of Compound 214+LPS vs. LPS alone. The overlap between the two sets is 45 transcripts.

A further RNASeq analysis of expression in LPS-stimulated BV2 cells in the presence and absence of Compound 214 and Rolipram (see Example 7) shows 293 genes significantly affected by Compound 214 but not Rolipram, 251 significantly affected by Rolipram but not Compound 214, and only 114 affected by both, an overlap of only about 17%.

In still a further experiment, an analysis of expression in in LPS-stimulated BV2 cells in the presence and absence of Compound 214 and Rolipram, shows that the differentially expressed genes for each pair ((LPS vs LPS+rolipram, LPS vs LPS+ITI-214) share about half of the most highly significant genes. For example, the assay demonstrates 1240 genes significantly affected by Compound 214 but not Rolipram, 1463 significantly affected by Rolipram but not Compound 214, and only 683 affected by both, an overlap of only about half.

The relatively small overlaps indicate that the effects of PDE1 inhibitors on these cells in response to LPS stimulation are very different from the effects of PDE4 inhibitors. While PDE4 inhibitors are often considered to be anti-inflammatory, the two types of inhibitors in this case are, for the most part, affecting expression of completely different genes.

Moreover, the expression levels of PDEs in BV2 cells to that of mouse brain microglia as determined by RNAseq quantitation of gene transcripts are compared. As detailed in Table A, PDE1B is the second most abundant PDE transcript in freshly isolated mouse microglia, and the most abundant PDE transcript in BV2 cells. PDE4B, PDE4A, PDE7A, and PDE8a expression is also substantial (≥0.7 FPKM/RPKM) in both cell types. Among the several PDEs enzymes detected by RNA-Seq in the BV2 cells, PDE1 is the only one with the ability to hydrolyze both cAMP and cGMP. The relative abundance of PDE1B and PDE4 isoenzymes in BV2 cells potentially indicate to that these are an adequate model for inhibitor studies (Table A):

TABLE A

| | Pde1b | Pde4b | Pde4a | Pde7a | Pde8a |
|---|---|---|---|---|---|
| Expression retained | | | | | |
| Microglia | 9.9 | 8.1 | 2.3 | 1.8 | 0.4 |
| BV2 cells | 4.2 | 1.5 | 2.8 | 0.7 | 0.4 |
| Abundant, expression lost | | | | | |
| | Pde3b | Pde2a | Pde8b | Pde9a | |
| Microglia | 33.6 | 9.6 | 2 | 0.5 | |
| BV2 cells | X | 0.2 | X | X | |
| Other, expression lost | | | | | |
| | Pde4d | Pde1a | Pde10a | Pde7b | |
| Microglia | 0.4 | 0.3 | 0.3 | 0.3 | |
| BV2 cells | X | X | X | X | |
| Not in microglia | | | | | |
| | Pde1c | Pde4c | Pde11a | | |
| Microglia | X | X | X | | |
| BV2 cells | X | 1.2 | X | | |

Example 4

Effect on IL1β Expression in Microglia-Derived Cells

Figure 2:
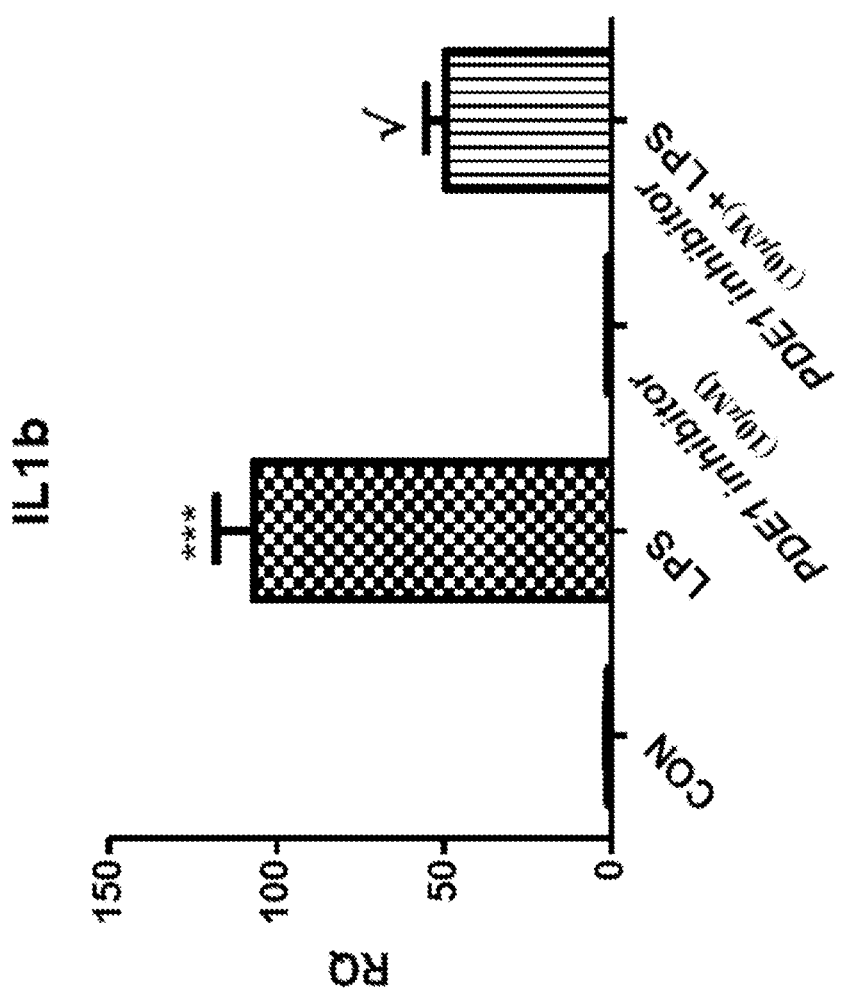
FIG. 2 depicts that a PDE1 inhibitor (Compound 214) suppresses LPS-induced IL1β in BV2 cells

BV2 cells are incubated with (i) LPS (10 microgram/ml), (ii) Compound 214 (10 microgram/ml), or (iii) LPS and Compound 214. Levels of IL1β are measured using quantitative PCR of IL1β mRNA. IL1β is considered a marker of inflammation. Results are depicted in FIG. 2 (RQ: relative quantification of changes in gene expression in treated versus control samples; ***p<0.01 vs control, √p<0.01 vs LPS alone; ANOVA with Newman-Keuls post-hoc test). Administration of a PDE1 inhibitor of the present invention thus significantly blunts the LPS-induced increase in expression of IL1β in microglia-derived cells.

Example 5

Effect on IL1β Expression in Hippocampus In Vivo

Figure 3:
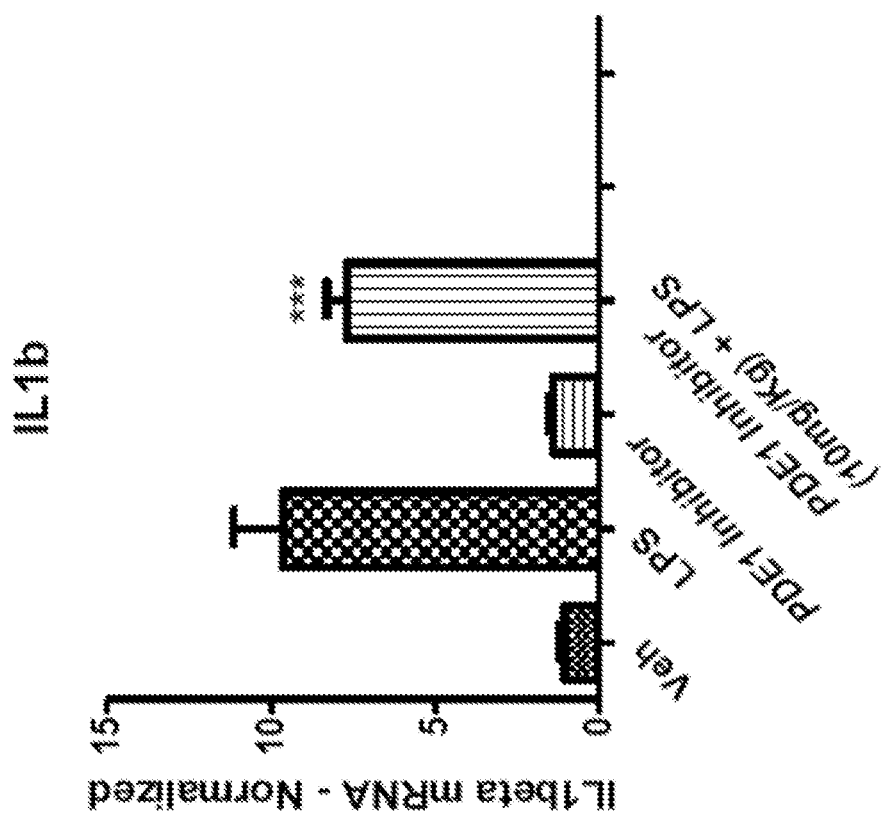
FIG. 3 depicts that a PDE1 inhibitor (Compound 214) suppresses LPS-induced IL1β in mouse hippocampus, in vivo.

Mice are injected with (i) LPS (2 mg/kg, s.c.), (ii) Compound 214 (10 mg/kg, i.p.), or (iii) LPS and Compound 214. At six hours post injection, levels of IL1β in the hippocampus are measured via quantitative PCR of IL1β mRNA. IL1β is considered a marker of inflammation. Data are presented in FIG. 3 (***p<0.01 vs LPS alone, ANOVA with Newman-Keuls post-hoc test). The effect in vivo is similar to that seen in the BV2 cells: administration of a PDE1 inhibitor of the present invention significantly blunts the LPS-induced increase in expression of IL1β in the brain.

Example 6

Effect on Neuroinflammatory Gene Expression in BV2 Cells

Figure 4A:
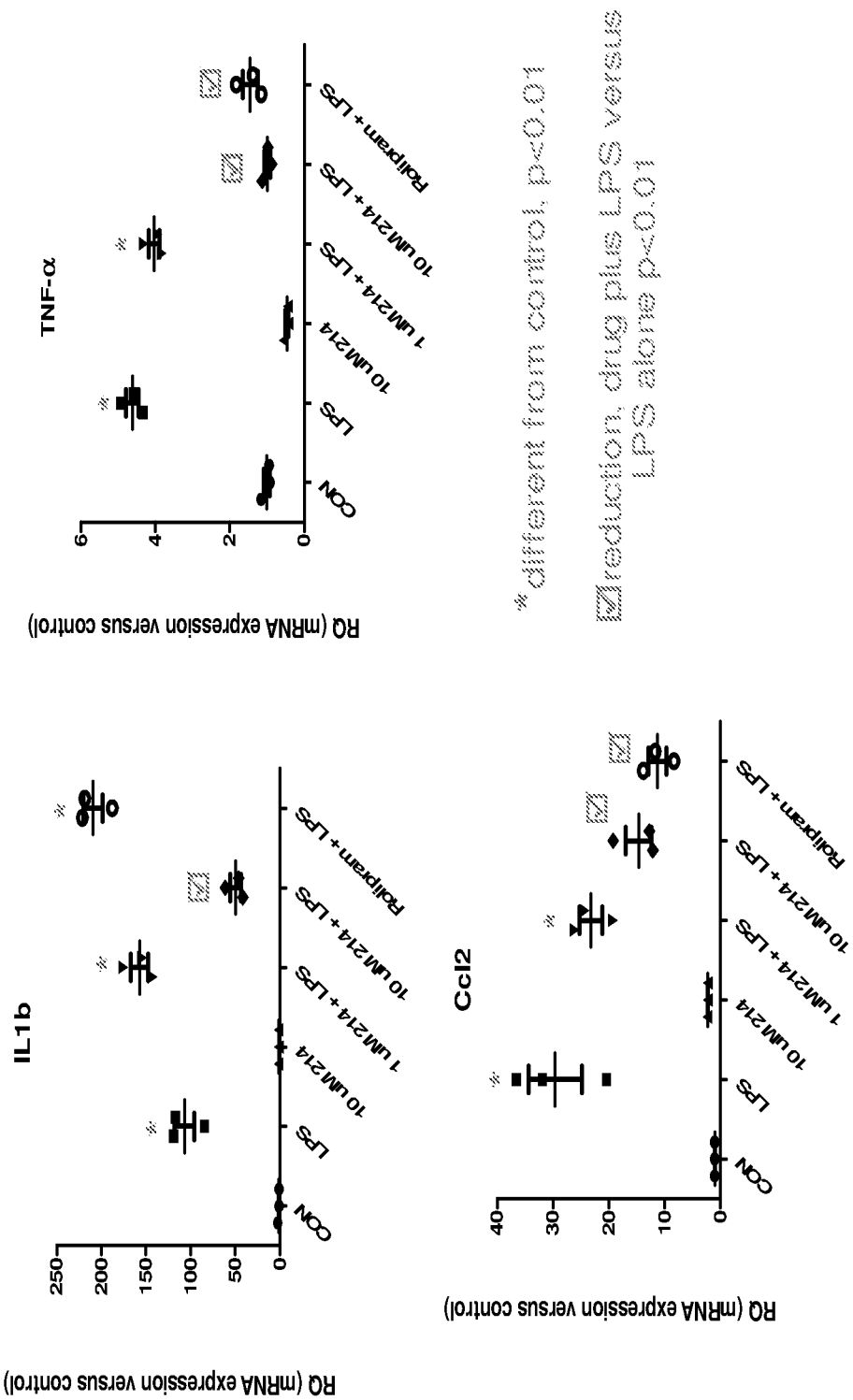
FIG. 4a depicts that a PDE1 inhibitor (Compound 214) significantly reduces the LPS-induced increase in expression of the inflammatory cytokines IL1β, TNF-α, and Ccl2 in BV2 cells, as measured by quantitative PCR, while a PDE4 inhibitor, rolipram, displays a different profile. In a separate experiment, FIG. 4b demonstrates that administration of a PDE1 inhibitor of the present invention (Compound 214) greatly reduces or blunts LPS-induced changes in proinflammatory markers in BV2 cells (FIG. 4b).

Administration of a PDE1 inhibitor of the present invention (Compound 214) at 10 μM significantly reduces the LPS-induced increase in expression of the inflammatory cytokines IL1β, TNFα, and Ccl2 in BV2 cells, as measured by quantitative PCR, as described in Example 4 with respect to IL1β. The PDE4 inhibitor, rolipram, displays a different profile, increasing IL1β expression, while reducing expression of TNF-α and Ccl2. Data are presented in FIG. 4a.

Figure 4B:
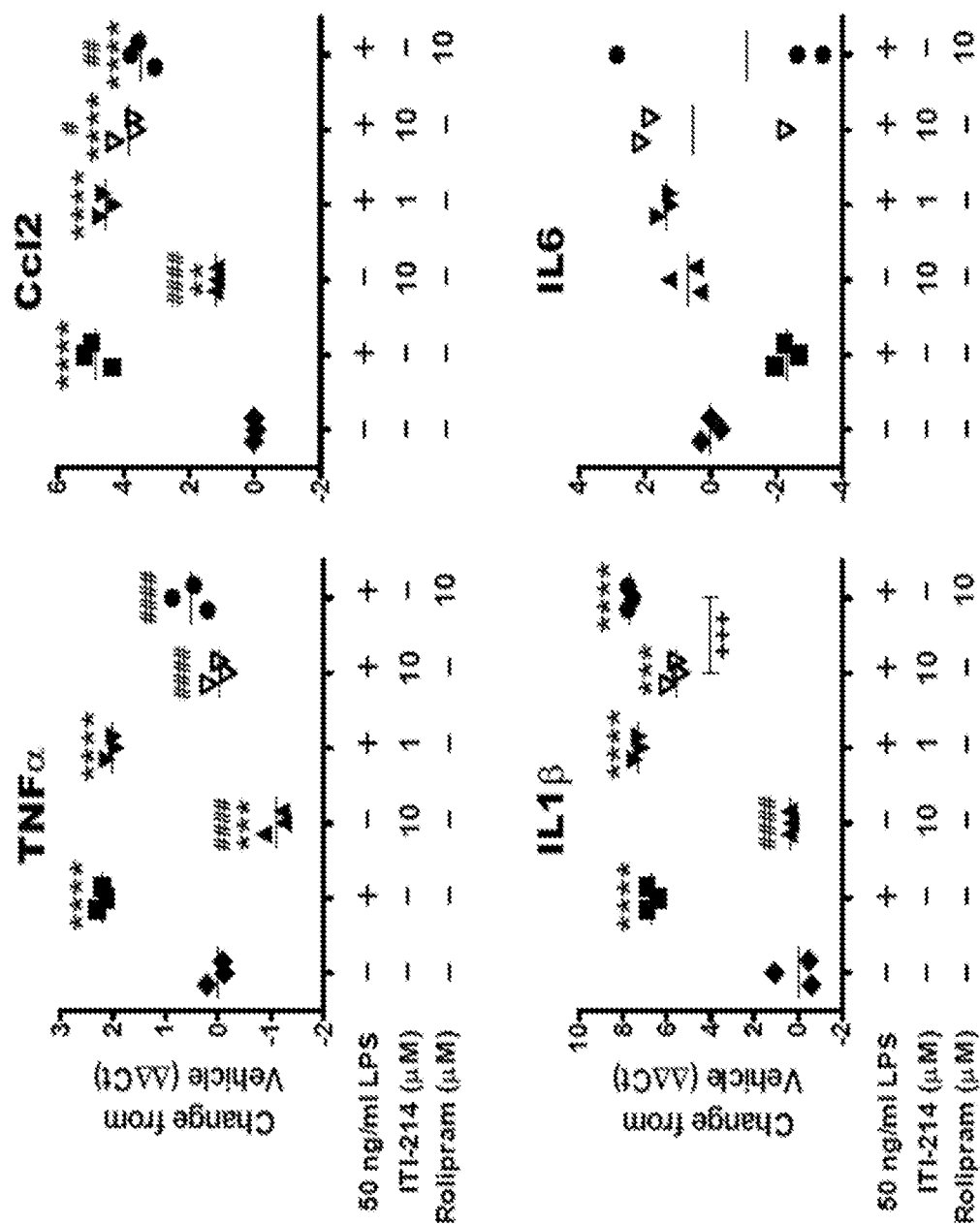

In a separate experiment, administration of a PDE1 inhibitor of the present invention (Compound 214) greatly reduces or blunts LPS-induced changes in proinflammatory markers in BV2 cells (FIG. 4b). BV2 cells are pretreated with compound, ITI-214 or rolipram, a PDE4 inhibitor, then stimulated with 50 ng/ml LPS for 4 hours. Expression levels of TNF, IL1β, Ccl2, and IL6 are measured. Normalized mRNA levels are shown as change from vehicle (ΔΔCt) and compared using a one-way ANOVA. Lines denote the mean. * Significantly different from vehicle, #Significantly different from LPS. * p<0.05, p<0.01, *p<0.001, ****p<0.0001. The mRNA transcripts for TNF, IL1β, and Ccl2—three of the four cytokines studied in vivo—were elevated in BV2 cells treated with 50 ng/ml LPS. The mRNA signals for TNF and Ccl2 were significantly decreased by treatment with ITI-214 (10 μM), and IL1β mRNA signal trended downward.

Example 7

Inhibition of LPS-Induced TNFα Release from BV2 Cells

PDE1 inhibition reduces LPS-induced TNFα gene expression and release from BV2 cells.

Figure 5:
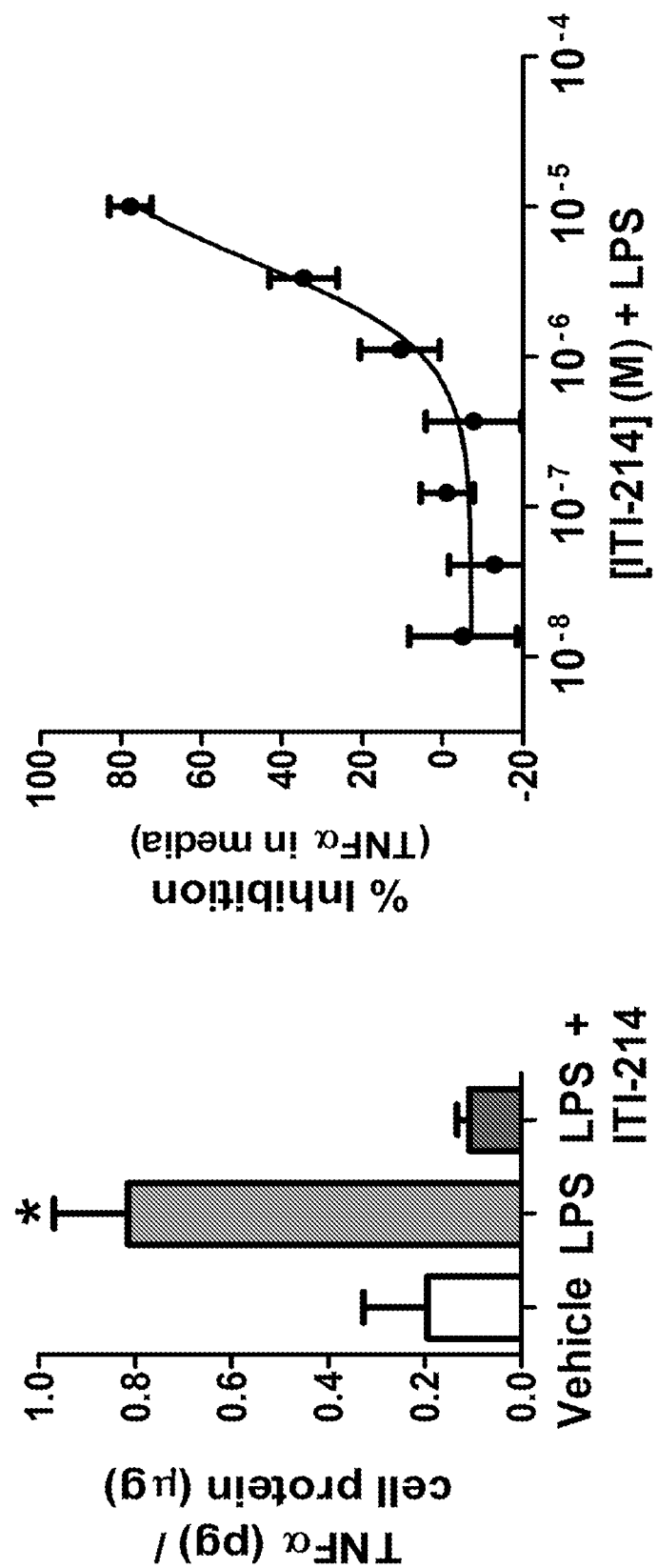
FIG. 5 depicts inhibition of LPS-induced TNFα release from BV2 cells.

TNFα release: TNFα levels are measured in BV2 conditioned media and normalized to cell protein levels. Inhibition of LPS-induced TNFα release from BV2 cells is depicted in FIG. 5. The left panel shows BV2 cells treated with 10 μM Compound 214 and 50 ng/ml LPS (one-way ANOVA, *p<0.05, Vehicle n=16, LPS n=31, LPS+214 n=14). The right panel shows a dose-dependent inhibition of LPS-induced TNFα release (50 ng/ml LPS stimulation) in response to Compound 214 (measured as % inhibition of total LPS response per experiment).

Figure 6:
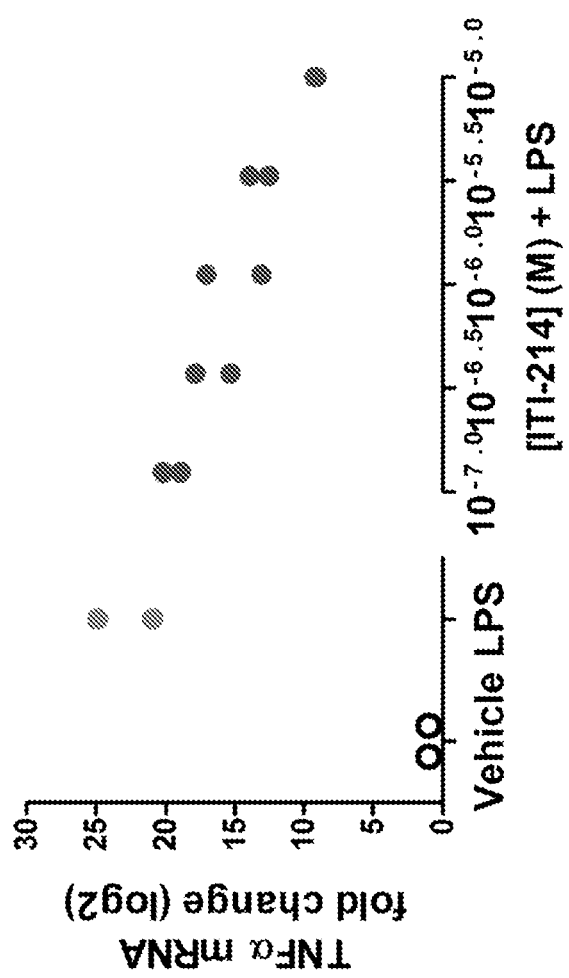
FIG. 6 depicts dose dependent reduction by a PDE1 inhibitor of LPS-stimulated TNFα mRNA expression.

TNFα gene expression: FIG. 6 shows that this dose dependent reduction of TNFα release as measured in the media corresponds to a reduction in TNFα mRNA expression.

Example 8

Effect on Neuroinflammatory Gene Expression in BV2 Cells and to In Vivo Mouse Striatum The effects of a selective PDE1 inhibitor (Compound 214) are tested in LPS stimulated BV2 cells by measuring changes in cytokine release using ELISA and in gene expression using RT-qPCR and RNA-Seq. (Experiment A (n=4): (1) Vehicle; (2) 10 μM Compound 214; (3) 50 ng/ml LPS; (4) 50 ng/ml LPS+10 μM Compound 214; Experiment B (n=2): (1) 50 ng/ml LPS; (2) 50 ng/ml LPS+10 μM Compound 214; (3) 50 ng/ml LPS+10 μM Rolipram (a known potent PDE4 inhibitor)). The test compound is added first, the LPS is added one hour later, and the cells and/or media are harvested at five hours from commencement of the experiment.

PDE1 inhibition prevents LPS-induced increases in TNFα release in BV2 cells. Similarly, LPS-induced increases in TNFα, IL-1β, and Ccl2 mRNA expression are reduced by >50% both in BV2 cells and in mice (p<0.01) upon PDE1 inhibition. To better understand the actions of PDE1 inhibition on resting and LPS-activated microglia, we examine transcriptional regulation using RNA-Seq. A subset of genes whose transcript expression is significantly changed with PDE1 inhibition is identified. Using gene ontology software (AmiGO 2), it is seen that these genes are significantly (p<0.05) enriched in cell migration and extravasation pathways as well as inflammatory pathways. Of the genes induced by LPS, a subset is attenuated by PDE1 inhibition, all of which are significantly associated with inflammatory pathways (p<0.05). PDE4 inhibition attenuates a different subset of LPS-induced genes, demonstrating the unique properties of our target (about 17% overlap with PDE1 inhibition).

Cells: BV2 mouse microglial cell line (ICLC, Italy) grown in 2% or 10% heat-inactivated FBS.

TNFαELISA: Thermo Fisher mouse TNFα colorimetric, sandwich ELISA kit. Interpolatee values from standard curve. Dose response is fit to a 4-parameter logistic curve.

RTqPCR: RNA from BV2 cells purified using RNeasyKit (Qiagen) and from mouse tissue using TRIzol (Ambion). TaqMan primer-probe assays from Thermo Fisher. mRNA levels for all conditions are normalized to GAPDH and to vehicle control (ΔΔCt). Data are analyzed statistically using one-way ANOVA with the Bonferroni post-test for multiple comparisons.

Our results indicate that inhibition of PDE1 regulates activity in microglia, reducing expression of inflammatory genes, providing a rationale to use PDE1 inhibitors to treat toxic neuroinflammation.

RNASeq: Flashfreeze BV2cells, isolate RNA, prepare a library using polyA selection, and conduct 1×50 bp single read sequencing on the Illumina HiSeq 2500 in High Output mode (using V4 chemistry). Genes are mapped to reference genome (GRCm38) using CLC Genomics Server. Number of reads per sample average ~17 million. Differential gene expression analysis is performed using DESeq2software (Bioconductor.org). Differentially expressed genes (p<0.01, Waldtest) are reported as log 2(fold change).

The following table demonstrates a summary of initial results of neuroinflammatory biomarker expression in both BV2 cells and mouse striatum subject to LPS administration in the presence or absence of a PDE1 inhibitor (Compound 214) or a PDE4 inhibitor (rolipram). The results are based upon an evaluation of samples using Q-PCR.

Figure 7:
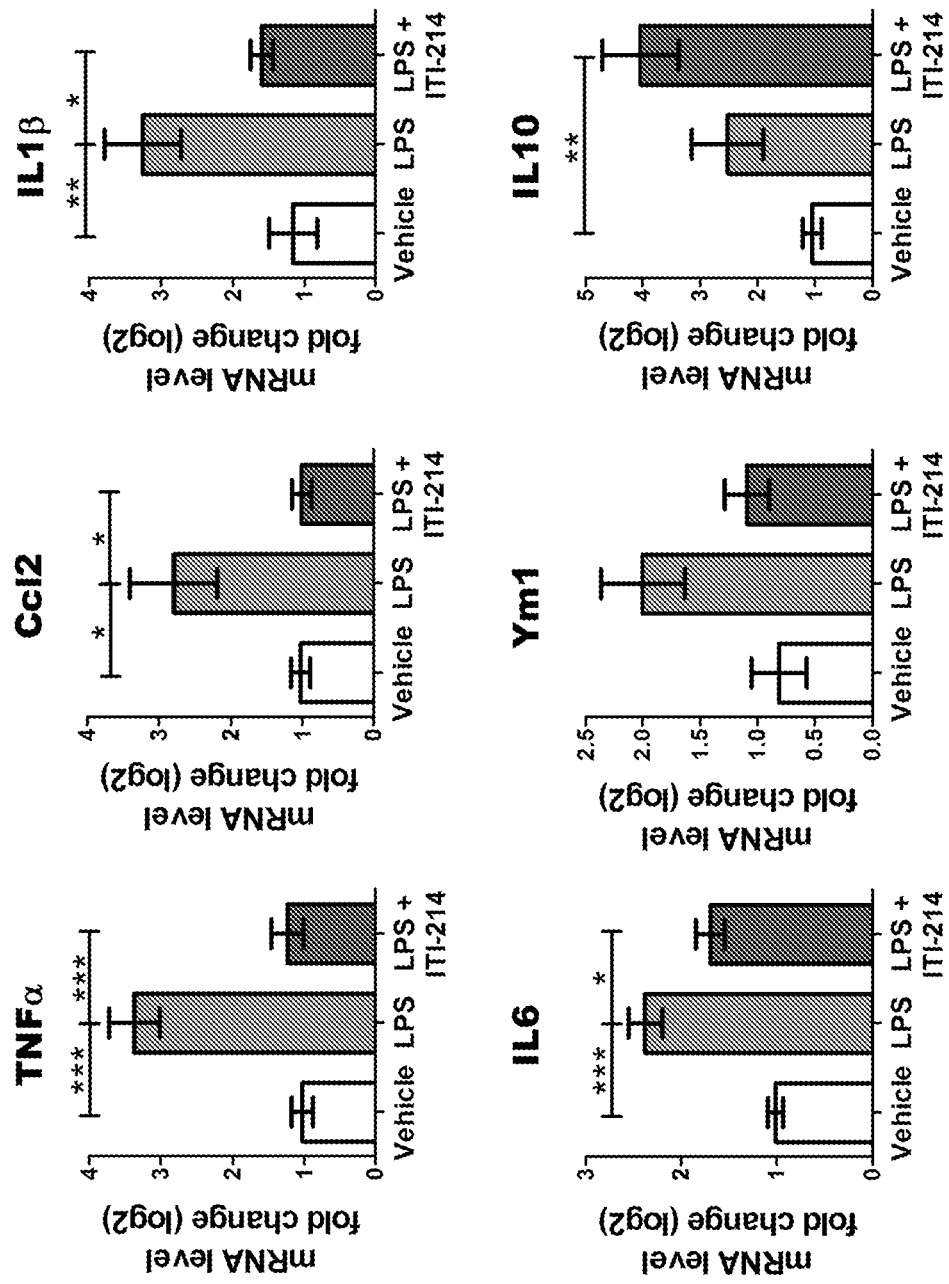
FIG. 7 depicts inhibition by a PDE1 inhibitor of LPS-induction of pro-inflammatory cytokine expression and an enhancement of expression of an anti-inflammatory cytokine (IL-10).

Data from a further experiment measuring the effect of PDE1 inhibition on inflammatory gene expression in mouse striatum is depicted in FIG. 7. Adult mice (at least 2 month old, male C57BL/6) are treated with both Compound 214 (10 mg/kg i.p.) and LPS (500 µg/kg s.c.), and sacrificed after two hours. Striatal tissue is isolated and flash frozen, and RNA is extracted. Measurements from RT-qPCR are shown as log 2 fold change (2ΔΔCt). n=4 *p<0.05, p<0.01, *p<0.001, ****p<0.0001.

In addition to confirming that the PDE1 inhibitor inhibits LPS stimulation of the pro-inflammatory cytokines TNFα, Ccl2, IL-1β, and IL-6, the PDE1 inhibitor is seen to significantly enhance expression of the anti-inflammatory cytokine IL-10.

Figure 8:
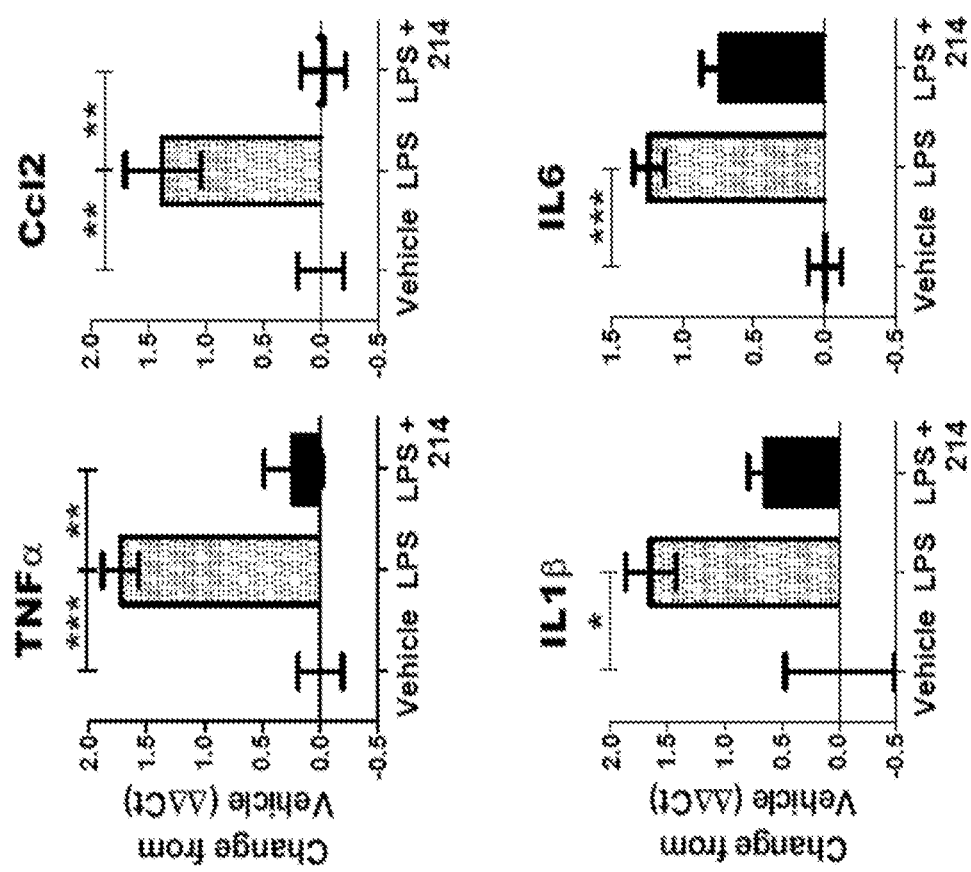
FIG. 8 depicts a PDE1 inhibitor (Compound 214) prevents LPS-induced inflammatory gene expression changes in mice. Adult mice are treated with vehicle (white bars), 500 mg/kg LPS s.c. (gray bars), or 10 mg/kg ITI-214 i.p. and 500 μg/kg LPS s.c. (black bars) for 2 hours (n=4). Striatal tissue is analyzed for mRNA levels of TNF, IL1β, Ccl2, and IL6. Expression levels are shown as change in Q-PCR signal from vehicle (ΔΔCt) and compared using an ANOVA. * $p<0.05$,  $p<0.01$, * $p<0.001$.

Further Effects on Neuroinflammatory Gene Expression in BV2 Cells and to In Vivo Mouse Striatum Data from yet another experiment measuring the effect of PDE1 inhibition on inflammatory gene expression in mouse striatum is depicted in FIG. 8. Adult mice are treated with vehicle (white bars), 500 mg/kg LPS s.c. (gray bars), or 10 mg/kg (Compound 214) i.p. and 500 µg/kg LPS s.c. (black bars) for 2 hours (n=4). Striatal tissue is analyzed for mRNA levels of TNF, IL1β, Ccl2, and IL6. Expression levels are shown as change in Q-PCR signal from vehicle (ΔΔCt) and compared using an ANOVA. * p<0.05, p<0.01, *p<0.001.

The Applicants measure mRNA levels of four common inflammatory markers (TNF, IL1β, Ccl2, and IL6) using quantitative PCR (FIG. 8). In adult mice treated with 500 µg/kg LPS s.c. for 2 hours, mRNA expression levels of all four markers increases significantly as measured in isolated tissue samples from the striatum (FIG. 8). A dose of 10 mg/kg (Compound 214) which is delivered i.p. attenuates the expression of TNF and Ccl2. In this experiment, levels of IL1-beta and IL6 trended to lower levels as well, but do not reach significance.

Biological Processes Associated with PDE1 Inhibition in BV2 Cells

Experiment 1

The following table (Table 1) highlights biological processes associated with PDE1 inhibition in BV2 cells, by analyzing differentially expressed genes in Compound 214 comparisons from Experiment A and Rolipram comparisons from Experiment B, against a database of gene functions. Gene ontology analysis is generated using the AmiGO2

| Biomarker | BV2 + LPS | PDE1 Inhibitor | rolipram | Striatum Mouse + LPS | PDE1 Inhibitor | rolipram |
|---|---|---|---|---|---|---|
| Tumor necrosis factor | UP | Down | Down | UP | NC | Down |
| Interleukin 1 beta | Up | Down | UP UP | UP | NC | UP-UP |
| Interleukin 6 | NC | NC | NC | NC | NC | UP-UP |
| Chemokine (C-C) motif Ligand 2 | UP | Down | Down | UP | Down | Down |
| Leukemia inhibitory factor | NC | NC | UP | NC | NC | NC |
| Oncostatin M | NC | UP | UP | UP | Down | Down |

Administering a PDE1 inhibitor of the present invention correlates with either a decrease or no change in the expression of biomarkers: IL1β, TNF-α, and Ccl2 compared to samples treated only with LPS. Interestingly, the anti-inflammatory profile of the PDE1 inhibitor is quite different from that of the PDE4 inhibitor.

software version: 2.4.24 running PANTHER.PANTHER Overrepresentation Test (release20160715). GO Ontology database Released 2016-10-27. Reference List=*Mus musculus* (all genes in database). Bonferroni Correction. Biological processes shown are Headers in Hierarchy View (p<0.05).

TABLE 1

| Biological Process | Pathway ID | P-Value |
|---|---|---|
| Increase with Compound 214 vs Vehicle | | |
| positive regulation of inflammatory response | GO:0050729 | 3.83E−05 |
| leukocyte migration | GO:0050900 | 3.15E−04 |
| leukocyte migration involved in inflammatory response | GO:0002523 | 1.09E−03 |
| positive regulation of interleukin-8 production | GO:0032757 | 3.00E−03 |
| regulation of cellular extravasation | GO:0002691 | 5.90E−03 |
| leukocyte chemotaxis | GO:0030595 | 8.30E−03 |
| positive regulation of cellular extravasation | GO:0002693 | 3.89E−02 |
| Decrease with Compound 214 vs Vehicle | | |
| cellular response to lipopolysaccharide | GO:0071222 | 2.15E−02 |
| regulation of lymphocyte activation | GO:0051249 | 3.29E−02 |
| leukocyte differentiation | GO:0002521 | 3.45E−02 |
| regulation of adaptive immune response based on somatic recombination of immune receptors built from immunoglobulin superfamily domains | GO:0002822 | 3.58E−02 |
| Increase with Compound 214 vs Vehicle -Subset of genes highly expressed in microglia (FPKM > 10, Brain RNA-Seq database) | | |
| positive regulation of inflammatory response | GO:0050729 | 7.50E−04 |
| leukocyte chemotaxis | GO:0030595 | 2.63E−02 |
| positive regulation of cell-cell adhesion | GO:0022409 | 2.88E−02 |
| inflammatory response | GO:0006954 | 1.36E−02 |
| cellular metal ion homeostasis | GO:0006875 | 2.42E−02 |
| positive regulation of apoptotic process | GO:0043065 | 1.29E−02 |
| Increase with LPS vs Vehicle, Decrease with LPS + ITI-214 vs LPS | | |
| positive regulation of immune system process | GO:0002684 | 3.98E−08 |
| cellular response to lipopolysaccharide | GO:0071222 | 4.69E−05 |
| inflammatory response | GO:0006954 | 4.87E−05 |
| response to cytokine | GO:0034097 | 3.68E−03 |
| positive regulation of inflammatory response | GO:0050729 | 1.08E−02 |
| positive regulation of cytokine biosynthetic process | GO:0042108 | 1.59E−02 |
| positive regulation of cell death | GO:0010942 | 1.94E−02 |
| positive regulation of tumor necrosis factor production | GO:0032760 | 2.45E−02 |
| Increase with LPS vs Vehicle, Decrease with LPS + Rolipram vs LPS | | |
| cellular response to cytokine stimulus | GO:0071345 | 4.31E−03 |
| macrophage chemotaxis | GO:0048246 | 6.39E−03 |
| leukocyte migration | GO:0050900 | 2.18E−02 |
| positive regulation of GTPase activity | GO:0043547 | 3.92E−02 |
| Increase with LPS vs Vehicle, Increase with LPS + Rolipram vs LPS | | |
| negative regulation of secretion by cell | GO:1903531 | 2.73E−02 |

Experiment 2

In a still further experiment, using AmiGO, the following table (Table 2) analyzes regulatory pathways impacted by LPS and ITI-214 in RNAseq experiments in BV2 cells. Overall, the primary process type changes by LPS, and can be attenuated with inclusion of ITI-214, are believed to relate to inflammation, cytokine expression and cellular responses to LPS (Table 2). Generally, differentially expressed genes associated with ITI-214 treatment relative to vehicle are believed to associate with processes related to chemotaxis and migration. The genes that respond only to the combination of LPS and ITI-214 are believed to demonstrate enrichment for biological processes related to DNA replication, mitotic cycle, and DNA repair.

TABLE 2

| Biological Process | Pathway ID | Fold Enrichment | p-value |
|---|---|---|---|
| Vehicle vs Compound 214 | | | |
| positive regulation of tumor necrosis factor biosynthetic process | GO:0042535 | 15.17 | 3.15E−02 |
| toll-like receptor signaling pathway | GO:0002224 | 7.53 | 3.40E−03 |
| DNA-dependent DNA replication | GO:0006261 | 5.94 | 8.05E−05 |
| neutrophil chemotaxis | GO:0030593 | 5.83 | 3.88E−02 |
| cellular response to lipopolysaccharide | GO:0071222 | 5.82 | 3.14E−07 |
| regulation of bone mineralization | GO:0030500 | 5.48 | 2.71E−02 |
| positive regulation of inflammatory response | GO:0050729 | 5.43 | 2.97E−04 |
| positive regulation of leukocyte migration | GO:0002687 | 4.27 | 8.12E−03 |
| double-strand break repair | GO:0006302 | 3.78 | 4.03E−02 |
| regulation of reactive oxygen species metabolic process | GO:2000377 | 3.76 | 6.50E−03 |
| inflammatory response | GO:0006954 | 3.5 | 1.69E−08 |
| positive regulation of leukocyte cell-cell adhesion | GO:1903039 | 3.45 | 4.07E−02 |
| response to metal ion | GO:0010038 | 3.2 | 2.46E−02 |
| leukocyte differentiation | GO:0002521 | 3.04 | 4.63E−04 |
| regulation of MAP kinase activity | GO:0043405 | 2.91 | 2.71E−02 |

TABLE 2-continued

| Biological Process | Pathway ID | Fold Enrichment | p-value |
|---|---|---|---|
| cellular response to organonitrogen compound | GO:0071417 | 2.82 | 5.72E−03 |
| regulation of hemopoiesis | GO:1903706 | 2.79 | 6.79E−03 |
| lymphocyte activation | GO:0046649 | 2.79 | 2.00E−03 |
| negative regulation of immune system process | GO:0002683 | 2.71 | 3.69E−03 |
| negative regulation of cell cycle | GO:0045786 | 2.64 | 2.13E−02 |
| positive regulation of cell activation | GO:0050867 | 2.5 | 2.84E−02 |
| positive regulation of apoptotic process | GO:0043065 | 2.48 | 5.73E−04 |
| carboxylic acid metabolic process | GO:0019752 | 2.41 | 4.72E−05 |
| apoptotic process | GO:0006915 | 2.34 | 5.79E−05 |
| organophosphate metabolic process | GO:0019637 | 2.2 | 4.38E−03 |
| response to abiotic stimulus | GO:0009628 | 2.08 | 4.63E−03 |
| positive regulation of cell proliferation | GO:0008284 | 2.06 | 4.99E−03 |
| cellular lipid metabolic process | GO:0044255 | 2.04 | 4.09E−02 |
| phosphate-containing compound metabolic process | GO:0006796 | 2.04 | 9.60E−08 |
| positive regulation of catalytic activity | GO:0043085 | 2 | 3.14E−03 |
| immune response | GO:0006955 | 2 | 1.07E−03 |
| LPS vs. LPS + Compound 214 | | | |
| T cell costimulation | GO:0031295 | 10.39 | 1.28E−02 |
| toll-like receptor signaling pathway | GO:0002224 | 9.52 | 2.99E−07 |
| leukocyte mediated cytotoxicity | GO:0001909 | 7.93 | 7.24E−03 |
| positive regulation of cytokine biosynthetic process | GO:0042108 | 6.91 | 8.67E−05 |
| regulation of interleukin-2 production | GO:0032663 | 6.47 | 5.06E−03 |
| cellular response to lipopolysaccharide | GO:0071222 | 5.49 | 1.53E−07 |
| positive regulation of inflammatory response | GO:0050729 | 5.27 | 7.64E−05 |
| positive regulation of tumor necrosis factor production | GO:0032760 | 5.26 | 6.81E−03 |
| granulocyte migration | GO:0097530 | 4.95 | 3.20E−02 |
| leukocyte chemotaxis | GO:0030595 | 4.68 | 4.81E−04 |
| regulation of myeloid leukocyte differentiation | GO:0002761 | 4.6 | 6.24E−04 |
| response to calcium ion | GO:0051592 | 4.28 | 3.35E−02 |
| positive regulation of leukocyte migration | GO:0002687 | 4.14 | 2.99E−03 |
| positive regulation of lymphocyte proliferation | GO:0050671 | 3.87 | 1.58E−02 |
| B cell activation | GO:0042113 | 3.82 | 2.71E−03 |
| regulation of T cell proliferation | GO:0042129 | 3.75 | 3.66E−03 |
| regulation of adaptive immune response based on somatic recombination of immune receptors built from immunoglobulin superfamily domains | GO:0002822 | 3.7 | 2.88E−02 |
| inflammatory response | GO:0006954 | 3.67 | 1.65E−11 |
| glycerolipid metabolic process | GO:0046486 | 3.3 | 3.75E−04 |
| regulation of I-kappaB kinase/NF-kappaB signaling | GO:0043122 | 3.28 | 9.84E−03 |
| response to virus | GO:0009615 | 3.24 | 2.08E−02 |
| regulation of peptidyl-tyrosine phosphorylation | GO:0050730 | 3.01 | 1.57E−02 |
| regulation of angiogenesis | GO:0045765 | 2.94 | 3.71E−02 |
| cytokine-mediated signaling pathway | GO:0019221 | 2.91 | 1.80E−02 |
| negative regulation of cell adhesion | GO:0007162 | 2.89 | 3.19E−02 |
| phospholipid metabolic process | GO:0006644 | 2.79 | 3.78E−02 |
| regulation of MAP kinase activity | GO:0043405 | 2.73 | 3.61E−02 |
| positive regulation of apoptotic process | GO:0043065 | 2.69 | 7.61E−07 |
| negative regulation of immune system process | GO:0002683 | 2.64 | 1.47E−03 |

TABLE 2-continued

| Biological Process | Pathway ID | Fold Enrichment | p-value |
|---|---|---|---|
| leukocyte differentiation | GO:0002521 | 2.56 | 2.74E−02 |
| immune effector process | GO:0002252 | 2.55 | 9.04E−05 |
| negative regulation of protein phosphorylation | GO:0001933 | 2.42 | 3.00E−02 |
| innate immune response | GO:0045087 | 2.36 | 3.26E−04 |
| negative regulation of intracellular signal transduction | GO:1902532 | 2.31 | 1.29E−02 |
| defense response to other organism | GO:0098542 | 2.21 | 2.19E−02 |
| vasculature development | GO:0001944 | 2.19 | 4.69E−02 |
| positive regulation of transferase activity | GO:0051347 | 2.18 | 4.90E−02 |
| regulation of catabolic process | GO:0009894 | 2.07 | 9.69E−03 |
| intracellular signal transduction | GO:0035556 | 2.06 | 8.20E−07 |
| apoptotic process | GO:0006915 | 2.04 | 5.92E−03 |
| Vehicle v. LPS + Compound 214 (excluding differentially expressed genes also found in Vehicle vs LPS or Vehicle vs. Compound 214) | | | |
| pseudouridine synthesis | GO:0001522 | 10.45 | 1.23E−02 |
| pyrimidine nucleotide metabolic process | GO:0006220 | 7.3 | 4.98E−02 |
| DNA-dependent DNA replication | GO:0006261 | 5 | 7.52E−05 |
| mitotic sister chromatid segregation | GO:0000070 | 4.05 | 3.36E−02 |
| tRNA metabolic process | GO:0006399 | 3.57 | 1.38E−03 |
| DNA repair | GO:0006281 | 2.52 | 5.78E−04 |
| organophosphate biosynthetic process | GO:0090407 | 2.51 | 1.05E−02 |
| regulation of chromosome organization | GO:0033044 | 2.45 | 4.74E−02 |
| regulation of cell cycle process | GO:0010564 | 2.35 | 3.32E−04 |
| regulation of mitotic cell cycle | GO:0007346 | 2.33 | 1.00E−03 |
| cell division | GO:0051301 | 2.23 | 1.01E−02 |

Response of Selected Genes to ITI-214

In a further experiment a group of genes is selected for further analysis by RT-qPCR. For comparison, genes are analyzed which have been implicated in the scientific literature in microglial and astrocyte activation, including genes in the complement pathway.

Figure 9:
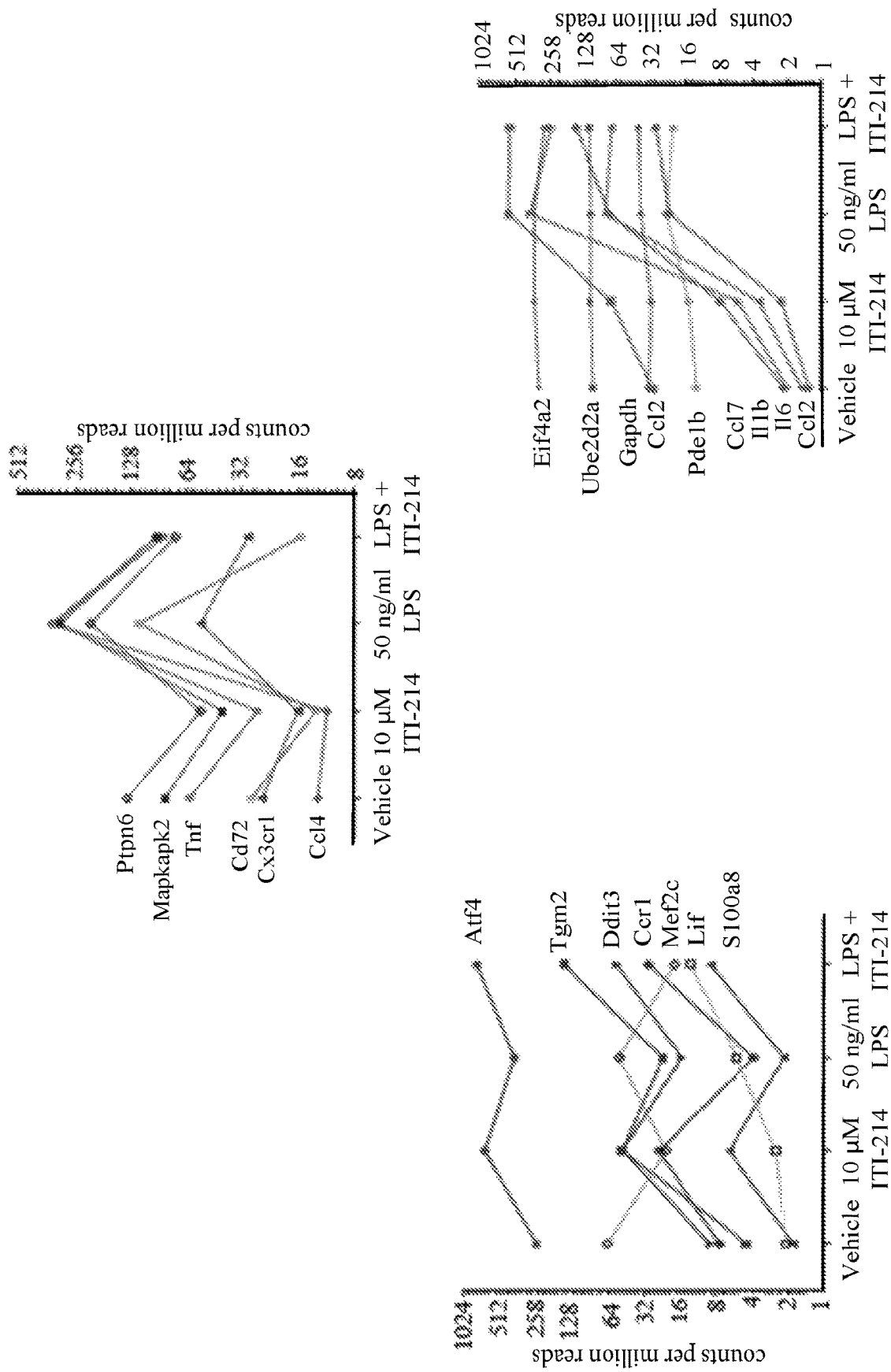
FIG. 9 demonstrates expression levels (FPKM) of selected genes with shared patterns of response to LPS and ITI-214. BV2 cells are treated with LPS, ITI-214, or LPS+ ITI-214.

In this select panel which can be derived from transcriptional response experiments, generally speaking, most of the genes fall into three general categories: those strongly induced by LPS and attenuated or reversed upon inhibition of PDE1, those predominantly responsive to Compound 214, and those strongly induced by LPS and weakly responsive to Compound 214. These patterns are displayed on parallel coordinates graphs in FIG. 9.

Figure 10A:
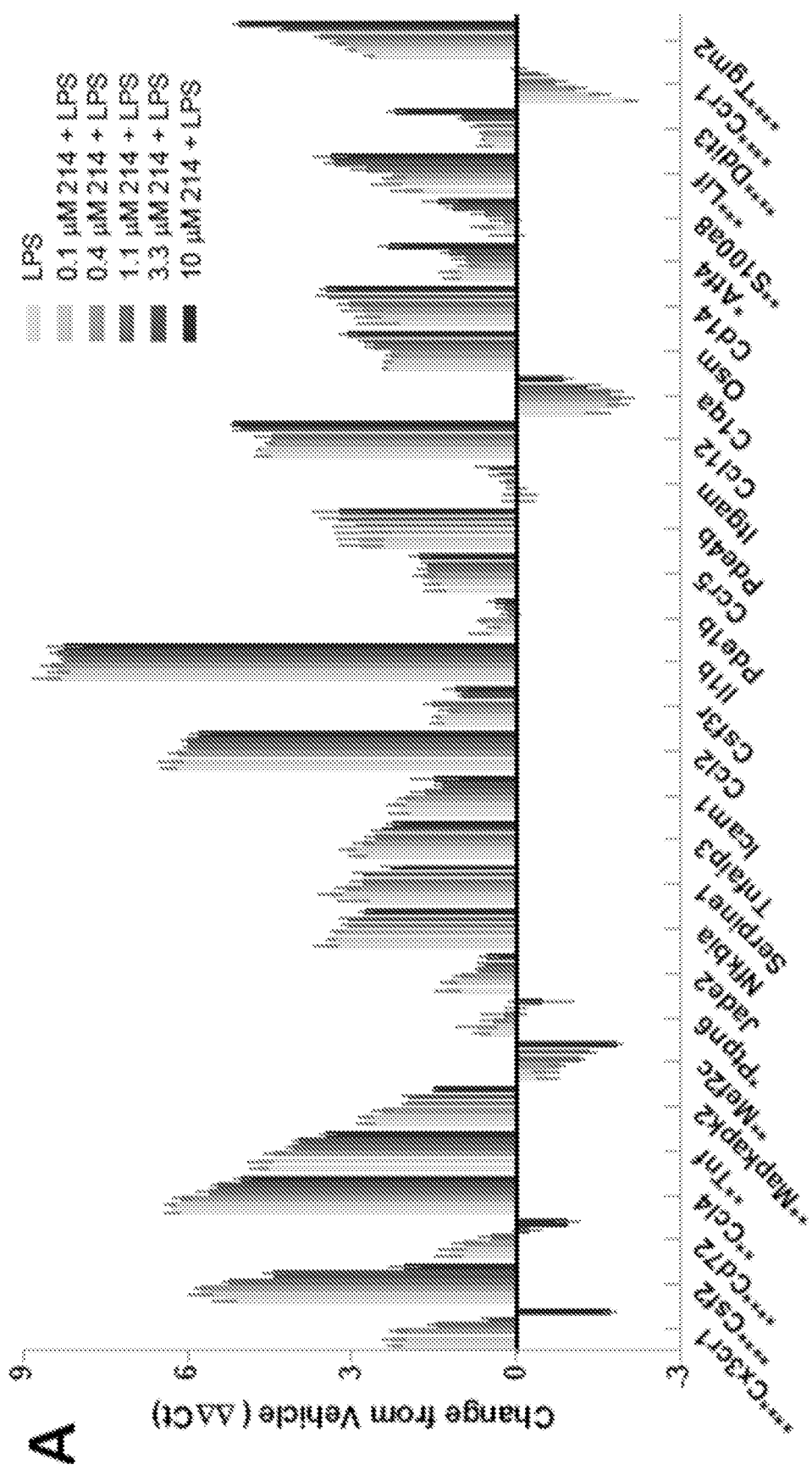
FIG. 10a shows the change in expression levels of each gene in BV2 cells with 50 ng/ml LPS and the indicated dose of ITI-214 (abbreviated 214).
Figure 10B:
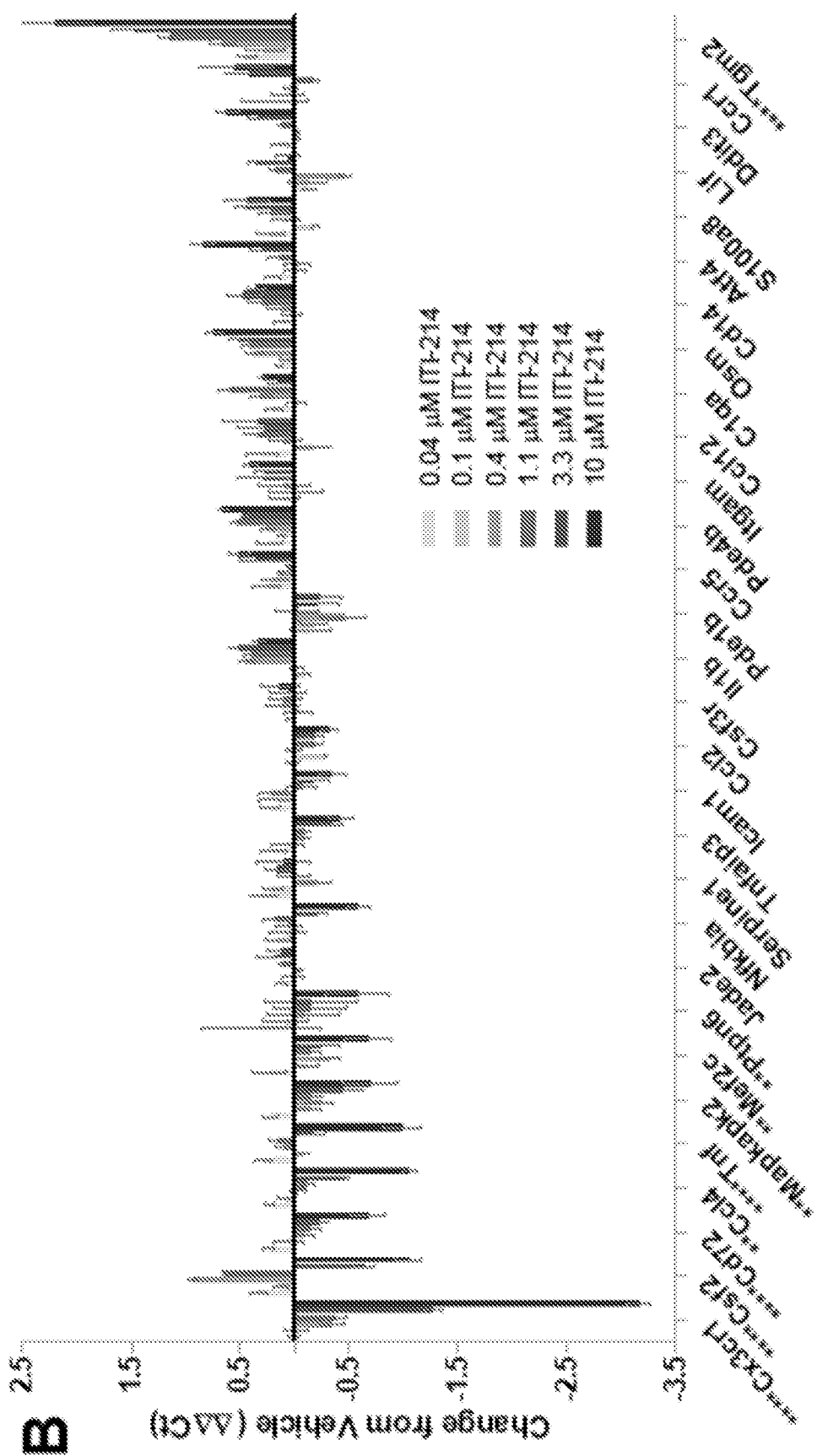
FIG. 10b demonstrates the dose dependent effects of ITI-214 in the absence of LPS stimulation. From left to right, for FIG. 10a, the bars indicate samples treated with: LPS, 0.1 μM 214+LPS, 0.4 μM 214+LPS, 1.1 μM 214+LPS, 3.3 μM 214+LPS, 10 μM 214+LPS, for each particular gene shown on the X-axis. From left to right, for FIG. 10b, the bars indicate samples treated with: 0.04 μM 214, 0.1 μM 214, 0.4 μM 214, 1.1 μM 214, 3.3 μM 214, 10 μM 214, for each particular gene shown on the X-axis.
Figure 11A:
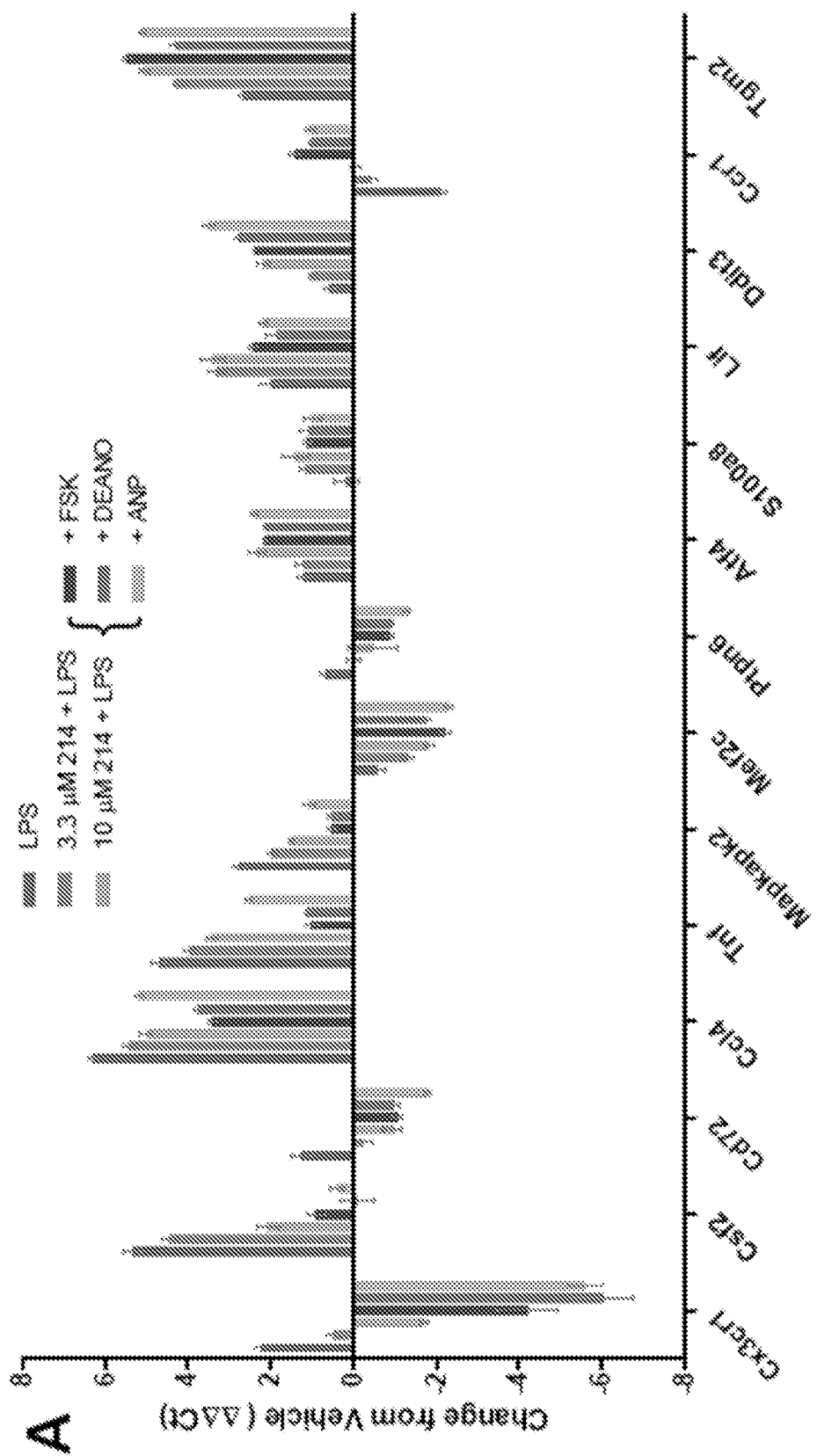
FIG. 11a cGMP-dependent activity of the PDE1 inhibitor of the present invention (Compound 214), particulate guanylyl cyclase activity with atrial natriuretic peptide (ANP) or soluble guanylyl cyclase activity with nitric oxide donor DEANO can be stimulated. For each gene, from left to right, the bars indicate treatment with: LPS, 3.3 µM 214, 10 µM 214, forskolin, and DEANO.

In one experiment, FIG. 10 demonstrates quantitated changes in target gene expression after treating BV2 cells with varying doses of ITI-214. A notable observation is that modulation of transcriptional responses to LPS by ITI-214 is dose dependent (FIG. 10a). FIG. 10a shows the change in expression levels of each gene in BV2 cells with 50 ng/ml LPS and the indicated dose of ITI-214. Dose dependent effects of ITI-214 in the absence of LPS stimulation are shown in FIG. 10b. All sample values are normalized to an average of 3 reference genes and to vehicle control (ΔΔCt). The error bars represent the mean+/−SEM (n=4). From left to right, for each cytokine grouping, the bars indicate samples treated with: LPS, 0.1 µM 214+LPS, 0.4 µM 214+LPS, 1.1 µM 214+LPS, 3.3 µM 214+LPS, 10 µM 214+LPS, for each particular gene shown on the X-axis. Significant changes between LPS and 10 µM ITI-214+LPS (A) and Vehicle and 10 µM ITI-214 (B) are marked on the X-axis gene names and are calculated using a one-way ANOVA. * p<0.05, p<0.01, *p<0.001, ****p<0.0001.

Effect of cAMP and cGMP on ITI-214 Dependent Inhibition of LPS; Activators

To investigate cGMP-dependent activity of the PDE1 inhibitor of the present invention (Compound 214), particulate guanylyl cyclase activity with atrial natriuretic peptide (ANP) or soluble guanylyl cyclase activity, with nitric oxide donor DEANO, can be stimulated. In one particular experiment, BV2 cells are treated with 10 µM forskolin (FSK) to activate adenylyl cyclases, 5 µM DEANO to activate soluble guanylyl cyclase, or 100 nM atrial natriuretic peptide (ANP) to activate particulate guanylyl cyclase. Alone, these activators are believed to have little or no effect on LPS induction of the selected genes. Upon combining forskolin with ITI-214 some of the effects of ITI-214 inhibition can be increased. For example, the following ITI-214 responsive transcripts are further down- or up-modulated by concomitant forskolin: chemokine receptor Cx3cr1, cytokines Csf2 and TNF, chemokine Ccl4, kinase MAPKAPK2, phosphatase PtpN6, chemokine receptor Ccr1. Cytokine LIF, demonstrates increased expression with LPS, and is further increased with ITI-214. However, LIF reverts to LPS-level expression when forskolin is added. Data is demonstrated in FIG. 11a.

Responses to DEANO treatment together with ITI-214 closely matches the responses seen with forskolin and ITI-214, and indicates that ITI-214 enhancement of either cGMP or cAMP signaling can reverse LPS-induction. There is not believed to be equivalent responses upon ANP and ITI-214 treatment. This possibly indicates that distinct pools of cGMP (cytosolic versus membrane associated) govern certain of the transcriptional responses to inhibition of PDE 1. There are believed to be equivalent responses upon addition of DEANO, FSK, or ANP to ITI-214 for the following cytokines: Cx3cr1, Csf2, PtpN6, and Ccr1 and LIF. Cc14, TNF, and MAPKAPK2, show weak or no response to the addition of ANP to the PDE1 inhibitor. Finally, mRNA responses to ITI-214 for C-type lectin CD72 and transcription factor Ddit3 are enhanced selectively by ANP. Data is demonstrated in FIG. 11a.

Two transcripts in the panel, Cx3cr1 and Tgm2, have the most dramatic change upon ITI-214 treatment. Induction of Cx3cr1 by LPS was significantly reduced by ITI-214 treatment, as was basal expression of this marker in the absence of LPS.

Effect of cAMP and cGMP on ITI-214 Dependent Inhibition of LPS; Inhibitors

Figure 11B:
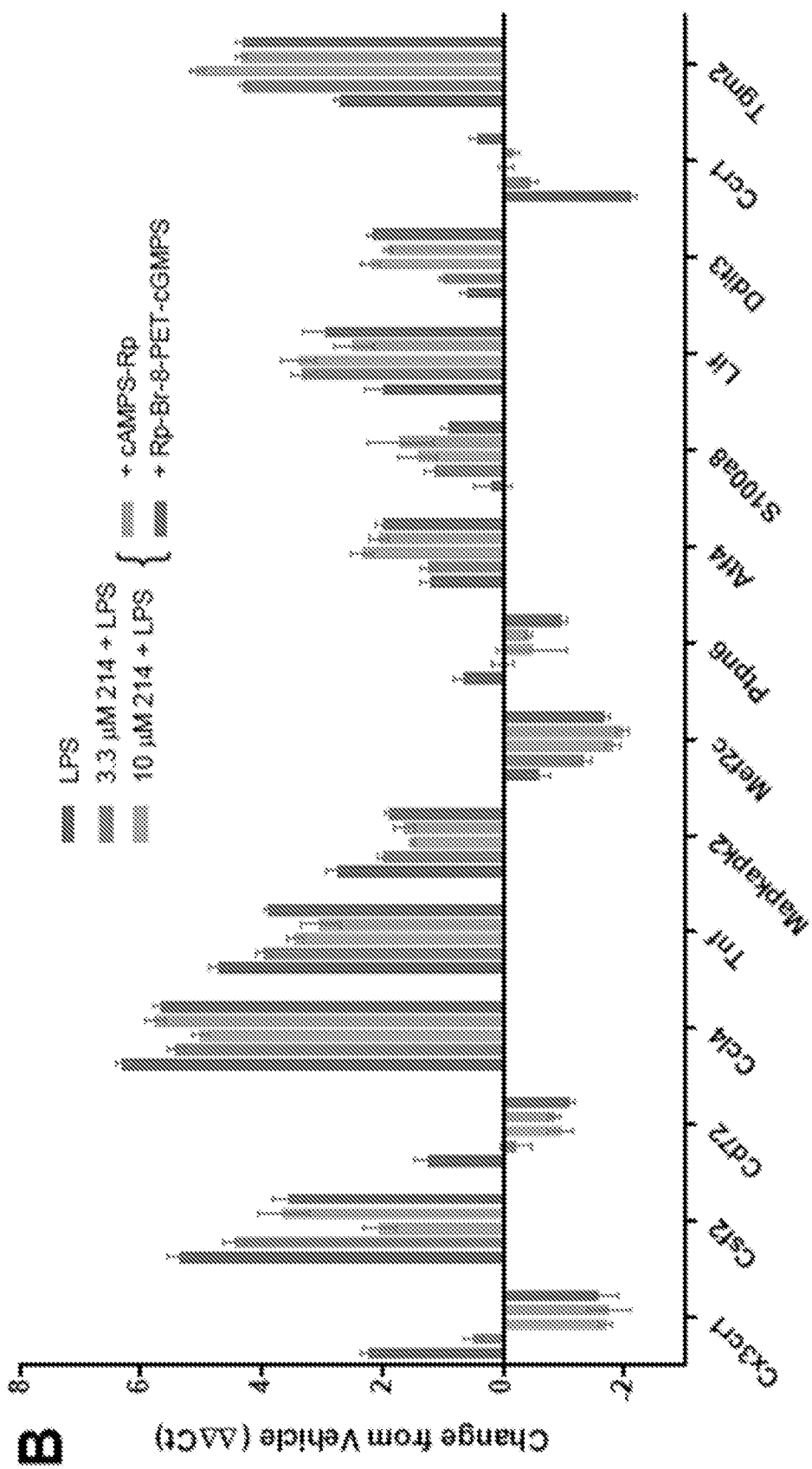
FIG. 11b demonstrates the influence of each cyclic nucleotide (cAMP or cGMP) on the ITI-214 response by combining LPS stimulation, ITI-214 inhibition of PDE1, and either PKA inhibitor (cAMPS-Rp) (100 µM) or PKG inhibitor (-8-Br-PET-cGMPS) (100 µM). From left to right, for FIG. 11b, the bars indicate samples treated with: LPS, 3.3 µM 214, 10 µM 214, cAMPS-Rp, and RP-8-Br-PET-cGMPS.

The influence of each cyclic nucleotide (cAMP or cGMP) on the ITI-214 response by combining LPS stimulation, ITI-214 inhibition of PDE1, and either PKA inhibitor cAMPS-Rp (100 µM) or PKG inhibitor-8-Br-PET-cGMPS (100 µM). Binding to cyclic nucleotide-dependent signaling molecules, these analogs do not provide activation, and prevent activation by authentic cyclic nucleotides. Moderate reduction of the impact of ITI-214 is the norm for these inhibitors (FIG. 11b). Note that gene expression levels upon addition of PKA or PKG inhibitor to 10 µM ITI-214 are on the order of those relative to LPS treatment alone were reduced to levels equivalent to 3.3 µM ITI-214. Data is demonstrated in FIG. 11b.

Example 9

Effect on Stress-Induced Inflammation

This experiment compares the impact of chronic stress on the brain cytokine/chemokine profile in wild type mice vs PDE1B conditional knockout mice. Assessing the effect of a PDE1 inhibitor of the present invention (Compound 214) on stress-induced cytokines changes in this model in the wild type and PDE1B knockout mice allows us to confirm that the effect of the PDE1 inhibitor is specific for PDE1B.

PDE1B conditional knockout mice are described in Siuciak J A, et al. "*Behavioral and neurochemical characterization of mice deficient in the phosphodiesterase-1B (PDE1B) enzyme.*" Neuropharmacology. 2007 July; 53(1): 113-24. Protocols for CUS and other models of chronic stress are described in Monteiro, et al., "*An Efficient Chronic Unpredictable Stress Protocol to Induce Stress-Related Responses in C57BL/6 Mice,*" Front Psychiatry. 2015; 6: 6 and in Mann et al., "*Chronic social defeat, but not restrain stress, alters bladder function in mice*" Physiol. Behav. 2015; Oct. 15; 150: 83-92.

Generally, wild type (control) mice and PDE1B conditional knockout mice, as appropriate, are exposed to the chronic stress using restraint stress in shallow water model (RSSW) as described by Mann et al (2015), above. For RSSW (21 days) mice are treated daily with either vehicle or Compound 214 (10 mg/kg, i.p. or p.o.) then put in a perforated conical tube with feet immersed in water for 4 h, then returned to single housing cages. Control mice for these experiments are also maintained in single housing cages. In accordance the stress protocol, the mice are monitored for the depression-like behavior profile. Mice are then sacrificed and tissue samples are collected. Brain are rapidly dissected (under conditions to preserve mRNA) and frozen at −80° C. for shipment to ITI. Blood is collected at sacrifice, prepared for serum. Brain tissue and serum is analyzed for a panel of markers, including pro-inflammatory and anti-inflammatory cytokines and chemokines.

A) Effect of the CUS Protocol on Neuroinflammatory Markers:

C57Bl/6 mice are subjected to the CUS protocol (14d, as described) or sham treatment, evaluated for depression-like behaviors at a specified time points, and sacrificed for collection of blood (serum preparation) and brain collection. Serum is analyzed for corticosterone (CORT) levels and other inflammatory markers. The brain is analyzed for a panel of inflammatory markers by qPCR (mRNA) and MSD (protein). The CUS protocol significantly elevates CNS and serum levels of proinflammatory cytokines/chemokines in parallel with induction of depression-like behaviors in normal mice.

B) Effect of a PDE1 Inhibitor on Stress-Induced Brain and Serum Inflammatory Markers:

Cohorts of $C_{57}Bl/6$ mice (WT for the PDE1B KO) are subjected to the CUS protocol (14d, as described) or sham treatment will receive either daily dosing with Compound 214 (10 mg/kg, i.p.) or vehicle. Mice are evaluated for depression-like behaviors at a specified time point to test the impact of the CUS protocol and of the PDE1 inhibitor treatment on the depression-like phenotype. Mice are immediately sacrificed for collection of blood (serum preparation) and brain collection. Serum is analyzed for CORT levels and other inflammatory markers. Brain samples are analyzed for a panel for a panel of inflammatory markers by qPCR (mRNA) and MSD (protein). The PDE1 inhibitor significantly suppresses CUS-induced CNS and serum markers (proinflammatory) and expression of depression-like behaviors in normal mice.

C) Effect of PDE1B KO on Stress-Induced Brain and Serum Markers:

Cohorts of WT and PDE1B KO mice are treated and subjected to either CUS protocol or sham treatment, with either daily dosing with Compound 214 (10 mg/kg, i.p.) or vehicle. Mice are evaluated for depression-like behaviors at a specified time point to test the impact of the CUS protocol and the treatment of the PDE1 inhibitor on the depression-like phenotype. Mice are immediately killed for collection of blood (serum preparation) and brain collection. Serum is analyzed for CORT levels and other inflammatory markers, and brain samples are also analyzed for a panel of inflammatory markers by qPCR (mRNA) and MSD (protein). PDE1B KO mice exhibit significantly suppressed CUS-induced CNS and serum markers (proinflammatory). Moreover, expression of depression-like behaviors which are seen in normal mice (i.e., having been subject to CUS protocol) are reduced in the KO. The PDE1 inhibitor on these tissue and serum markers and behaviors has no significant effect in the PDE1B KO mice.

Example 10

Effects in the Optic Nerve Injury Model

A PDE1 inhibitory compound is tested in an optic nerve injury model (i.e., the "optic crush" model). The studies described below are carried out using the selective PDE1 inhibitor IC200041, which has the following structure:

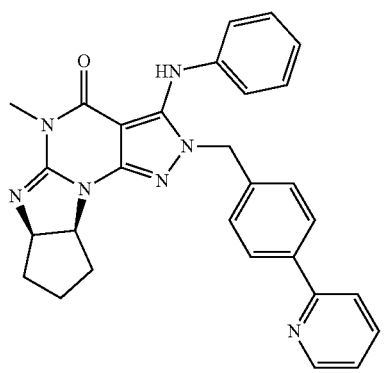 [SMILES: CN1C(=O)c2c(nn(Cc3ccc(-c4ccccn4)cc3)c2Nc2ccccc2)N2C1=N[C@@H]1CCC[C@@H]12]

In this model, optic nerve surgeries are carried out on male mice 8 wk of age (average body weight, 20-26 g) under general anesthesia, as described previously (Yin Y, et al., Oncomodulin links inflammation to optic nerve regeneration. Proc Natl Acad Sci USA. 2009; 106:19587-19592). Following nerve injury, 3 µl of fluid is removed from the eye and a solution containing the PDE1 inhibitory compound is injected intraocularly.

A total of 4 mouse retinas are treated with the PDE1 inhibitor, and phosphate buffered saline (PBS) is administered to a total of 10 mouse retinas as a control. Mice are typically euthanized with an overdose of anesthesia 14 days after optic nerve injury and are perfused with saline and 4% paraformaldehyde (PFA). These mice are 10 weeks old when killed. Optic nerves and eyes are dissected and post-fixed in PFA. Nerves are impregnated with 10% and then 30% sucrose, embedded in OCT Tissue Tek Medium (Sakura Finetek), frozen, cut in the longitudinal plane at a thickness of 14 µm, and mounted on coated slides. Regenerating axons are visualized by staining with a sheep antibody to GAP-43 followed by a fluorescently labeled secondary antibody. Axons are counted manually in at least 8 longitudinal sections per case at pre-specified distances from the injury site, and these numbers were converted into the number of regenerating axons at various distances.

After retinal insult, quantitative analysis shows that PDE expression in retinal ganglion cells is greatly increased. Messenger RNA (mRNA) for PDE1B in particular is upregulated about fourfold after injury. RNA is extracted from tissue using standard methods, and mRNA was quantitated using quantitative RNAseq sequencing methods. Standard mRNA for beta actin, and four glutamate receptors, namely NMDA R1 and AMPAK R1, R2 and R3, are evaluated in parallel and show no significant changes.

Figure 12:
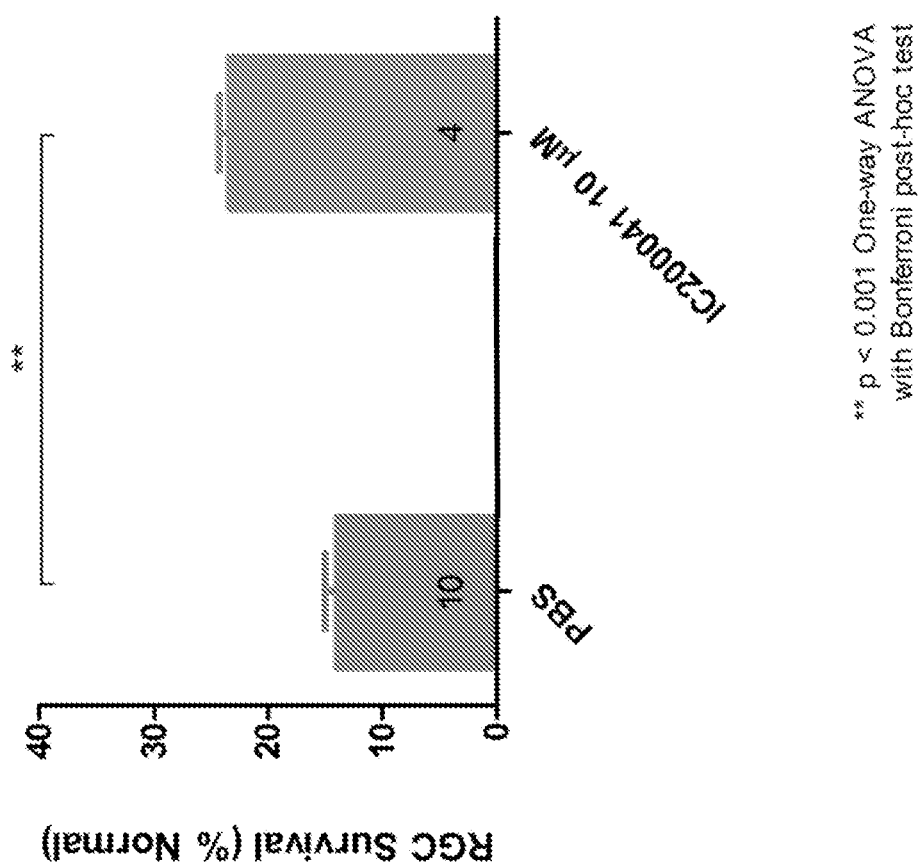
FIG. 12 demonstrates that the tested PDE1 inhibitor is highly effective in increasing the survival of retinal ganglion cells when compared with the PBS control in the optic injury model described in Example 10.

IC200041 is highly effective in increasing the survival of retinal ganglion cells when compared with the PBS control. Further, the difference in control retinal ganglion cells and those treated with IC200041 is statistically significant. Data is demonstrated within FIG. 12.

We claim:

1. A method of treatment or prophylaxis of inflammation and/or an inflammatory disease or disorder comprising administration of a PDE1 inhibitor to a patient in need thereof, wherein the PDE1 inhibitor is of Formula VII:

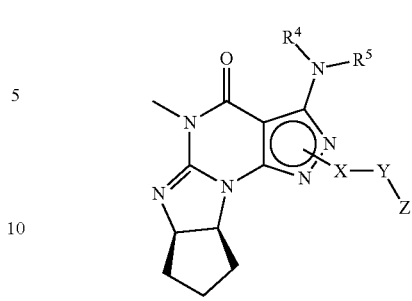

Formula VII wherein:
(i) X is $C_{1-6}$alkylene;
(ii) Y is a single bond, alkynylene, arylene or heteroarylene;
(iii) Z is H, aryl, heteroaryl, halo, halo$C_{1-6}$alkyl, —C(O)—$R^1$, —N($R^2$)($R^3$), or $C_{3-7}$cycloalkyl optionally containing at least one atom selected from a group consisting of N or O;
(iv) $R^1$ is $C_{1-6}$alkyl, halo$C_{1-6}$alkyl, —OH or —O$C_{1-6}$alkyl;
(v) $R^2$ and $R^3$ are independently H or $C_{1-6}$alkyl;
(vi) $R^4$ and $R^5$ are independently H, $C_{1-6}$alkyl or aryl optionally substituted with one or more halo, hydroxy or $C_{1-6}$alkoxy; and
(vii) wherein X, Y and Z are independently and optionally substituted with one or more halo, $C_{1-6}$alkyl, or halo $C_{1-6}$alkyl, in free base or pharmaceutically acceptable salt form.

2. A method according to claim 1 wherein the PDE1 inhibitor inhibits the activity of PDE1 with an $IC_{50}$ of less than 10 nM.

3. A method according to claim 1 for treatment or prophylaxis of neuroinflammation and/or diseases or disorders associated with neuroinflammation and/or microglial function, selected from:
  a. neurodegenerative conditions selected from Alzheimer's disease (AD), Parkinson's disease (PD), amyotrophic lateral sclerosis (ALS), and demyelinating conditions;
  b. stroke, cardiac arrest, hypoxia, intracerebral hemorrhage or traumatic brain injury;
  c. conditions characterized by abnormal neurotransmitter production and/or response, selected from depression, schizophrenia, post-traumatic stress disorder, anxiety, attention deficit disorder, and bipolar disease; and
  d. chronic CNS infections; and
  e. neuroinflammation consequent to chemotherapy.

4. The method of claim 1 wherein the patient has
  a. elevated levels of one or more pro-inflammatory cytokines; or
  b. reduced levels of one or more anti-inflammatory cytokines; or
  c. elevated levels of microglial M1 phenotype compared to microglial M2 phenotype.

5. The method of claim 1, wherein the PDE1 inhibitor is selected from any of the following:

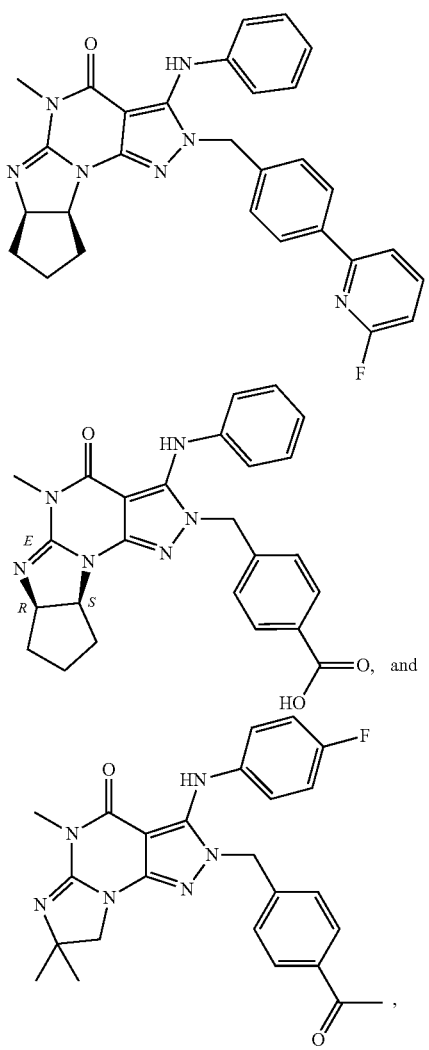

in free or pharmaceutically acceptable salt form.

6. The method of claim 5, wherein the PDE1 inhibitor is the following:

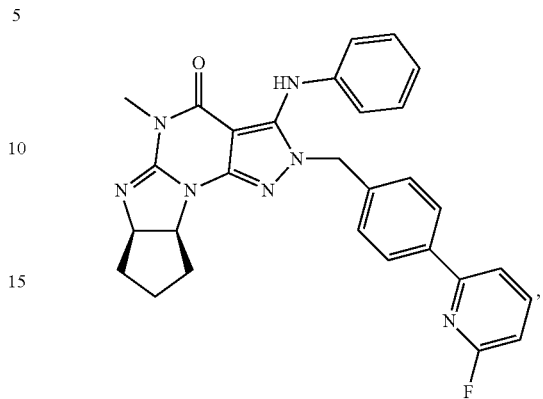

in free or pharmaceutically acceptable salt form.

7. The method of claim 1, wherein the PDE1 inhibitor is administered in combination with a PDE4 inhibitor.

8. The method of claim 1, wherein the PDE1 inhibitor is administered in combination with one or more antidepressant agents, in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotic agents.

9. The method of claim 1, wherein said treatment or prophylaxis of inflammation and/or an inflammatory disease or disorder is characterized by survival of retinal ganglion cells.

10. The method of claim 1, wherein said treatment or prophylaxis of inflammation and/or an inflammatory disease or disorder comprises the prevention, reduction, and/or reversal of neuroinflammation.

11. The method of claim 10, wherein said neuroinflammation is associated with increased expression and/or activation of microglial cells in the brain.

* * * * *